United States Patent
Ward et al.

(10) Patent No.: US 10,988,734 B2
(45) Date of Patent: *Apr. 27, 2021

(54) METHODS FOR PREPARING THERAPEUTICALLY ACTIVE CELLS USING MICROFLUIDICS

(71) Applicants: GPB SCIENTIFIC, INC., Richmond, VA (US); UNIVERSITY OF MARYLAND, BALTIMORE, Baltimore, MD (US); THE TRUSTEES OF PRINCETON UNIVERSITY, Princeton, NJ (US)

(72) Inventors: Anthony Ward, Rancho Santa Fe, CA (US); Roberto Campos-Gonzalez, Carlsbad, CA (US); Alison Skelley, Riverside, CA (US); Khushroo Gandhi, Palo Alto, CA (US); Curt Civin, Baltimore, MD (US); James C. Sturm, Princeton, NJ (US); Michael Grisham, Richmond, VA (US)

(73) Assignees: GPB Scientific, Inc., Richmond, VA (US); The Trustees of Princeton University, Princeton, NJ (US); University of Maryland, Baltimore, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/662,033

(22) Filed: Oct. 24, 2019

(65) Prior Publication Data
US 2020/0056153 A1 Feb. 20, 2020

Related U.S. Application Data

(63) Continuation of application No. 16/108,365, filed on Aug. 22, 2018, now Pat. No. 10,844,353, which is a
(Continued)

(51) Int. Cl.
*C12N 5/0783* (2010.01)
*A61P 35/02* (2006.01)
(Continued)

(52) U.S. Cl.
CPC ............ *C12N 5/0636* (2013.01); *A61K 35/17* (2013.01); *A61P 35/02* (2018.01);
(Continued)

(58) Field of Classification Search
None
See application file for complete search history.

(56) References Cited

U.S. PATENT DOCUMENTS 4,675,286 A 6/1987 Calenoff
5,427,663 A 6/1995 Austin et al.
(Continued)

FOREIGN PATENT DOCUMENTS

EP 1425294 B1 9/2004
EP 1462800 A1 9/2004
(Continued)

OTHER PUBLICATIONS

De Dreuzy et al, Biomedical Journal, Apr. 2016, 39: 24-38. (Year: 2016).*
(Continued)

*Primary Examiner* — Allison M Fox
(74) *Attorney, Agent, or Firm* — Law Office of: Michael A. Sanzo, LLC

(57) ABSTRACT

The present invention is directed to the use of microfluidics in the preparation of cells and compositions for therapeutic uses.

27 Claims, 32 Drawing Sheets

Related U.S. Application Data continuation-in-part of application No. PCT/US2017/057876, filed on Oct. 23, 2017.

(60) Provisional application No. 62/553,723, filed on Sep. 1, 2017, provisional application No. 62/567,553, filed on Oct. 3, 2017, provisional application No. 62/635,304, filed on Feb. 26, 2018, provisional application No. 62/656,939, filed on Apr. 12, 2018.

(51) Int. Cl.
  *A61K 35/17* (2015.01)
  *B01L 3/00* (2006.01)
  *C12N 5/00* (2006.01)

(52) U.S. Cl.
  CPC ... *B01L 3/502753* (2013.01); *B01L 3/502761* (2013.01); *C12N 5/0087* (2013.01); *B01L 2200/0652* (2013.01); *B01L 2300/0816* (2013.01); *B01L 2300/0864* (2013.01); *B01L 2400/086* (2013.01); *C12N 2531/00* (2013.01); *C12N 2533/54* (2013.01); *C12N 2533/74* (2013.01)

(56) References Cited

U.S. PATENT DOCUMENTS

| | | | |
|---|---|---|---|
| 5,676,849 A | 10/1997 | Sammons et al. | |
| 5,707,799 A | 1/1998 | Hansmann et al. | |
| 5,837,115 A | 11/1998 | Austin et al. | |
| 5,948,278 A | 9/1999 | Sammons et al. | |
| 5,968,820 A | 10/1999 | Zborowski et al. | |
| 6,241,894 B1 | 6/2001 | Briggs et al. | |
| 6,268,222 B1 | 7/2001 | Chandler et al. | |
| 6,685,841 B2 | 2/2004 | Lopez et al. | |
| 6,881,315 B2 | 4/2005 | Iida et al. | |
| 6,881,317 B2 | 4/2005 | Huang et al. | |
| 6,913,697 B2 | 7/2005 | Lopez et al. | |
| 6,949,355 B2 | 9/2005 | Yamanishi et al. | |
| 7,150,812 B2 | 12/2006 | Huang et al. | |
| 7,276,170 B2 | 10/2007 | Oakey et al. | |
| 7,318,902 B2 | 1/2008 | Oakey et al. | |
| 7,472,794 B2 | 1/2009 | Oakey et al. | |
| 7,682,838 B2 | 3/2010 | Wang et al. | |
| 7,735,652 B2 | 6/2010 | Inglis et al. | |
| 7,837,944 B2 | 11/2010 | Auner et al. | |
| 7,863,012 B2 | 1/2011 | Rao et al. | |
| 7,977,095 B2 | 7/2011 | Bonyhadi et al. | |
| 7,988,840 B2 | 8/2011 | Huang et al. | |
| 8,021,614 B2 | 9/2011 | Huang et al. | |
| 8,186,913 B2 | 5/2012 | Toner et al. | |
| 8,263,023 B2 | 9/2012 | Le Vot et al. | |
| 8,263,404 B2 | 9/2012 | Olken et al. | |
| 8,282,799 B2 | 10/2012 | Huang et al. | |
| 8,304,230 B2 | 11/2012 | Toner et al. | |
| 8,354,075 B1 | 1/2013 | Tai et al. | |
| 8,372,579 B2 | 2/2013 | Toner et al. | |
| 8,579,117 B2 | 11/2013 | Loutherback et al. | |
| 8,585,971 B2 | 11/2013 | Huang et al. | |
| 8,783,467 B2 | 7/2014 | Loutherback et al. | |
| 8,895,298 B2 | 11/2014 | Toner et al. | |
| 8,906,682 B2 | 12/2014 | June et al. | |
| 8,921,102 B2 | 12/2014 | Fuchs et al. | |
| 8,986,966 B2 | 3/2015 | Toner et al. | |
| 9,034,658 B2 | 5/2015 | Barber et al. | |
| 9,328,156 B2 | 5/2016 | June et al. | |
| 9,427,688 B2 | 8/2016 | Reichenbach | |
| 9,610,582 B2 | 4/2017 | Kapur et al. | |
| 9,629,877 B2 | 4/2017 | Cooper et al. | |
| 9,895,694 B2 | 2/2018 | Kapur et al. | |
| 9,956,562 B2 | 5/2018 | Huang et al. | |
| 10,324,011 B2 | 6/2019 | DiSilva et al. | |
| 10,844,353 B2 | 11/2020 | Ward et al. | |
| 2001/0036624 A1 | 11/2001 | Sumita et al. | |
| 2003/0049563 A1 | 3/2003 | Iida et al. | |
| 2003/0119077 A1 | 6/2003 | Tso et al. | |
| 2003/0159999 A1 | 8/2003 | Oakey et al. | |
| 2003/0180762 A1 | 9/2003 | Tuma et al. | |
| 2004/0019300 A1 | 1/2004 | Leonard | |
| 2004/0033515 A1 | 2/2004 | Cao | |
| 2004/0043506 A1 | 3/2004 | Haussecker et al. | |
| 2004/0224402 A1 | 11/2004 | Bonyhadi et al. | |
| 2005/0266433 A1 | 12/2005 | Kapur et al. | |
| 2005/0282293 A1 | 12/2005 | Cosman et al. | |
| 2006/0121624 A1 | 6/2006 | Huang et al. | |
| 2006/0134599 A1 | 6/2006 | Toner et al. | |
| 2006/0223178 A1 | 10/2006 | Barber et al. | |
| 2007/0026381 A1 | 2/2007 | Huang et al. | |
| 2007/0026413 A1 | 2/2007 | Toner et al. | |
| 2007/0026414 A1 | 2/2007 | Fuchs et al. | |
| 2007/0026415 A1 | 2/2007 | Fuchs et al. | |
| 2007/0026416 A1 | 2/2007 | Fuchs et al. | |
| 2007/0026417 A1 | 2/2007 | Fuchs et al. | |
| 2007/0026418 A1 | 2/2007 | Fuchs et al. | |
| 2007/0059680 A1 | 3/2007 | Kapur et al. | |
| 2007/0059716 A1 | 3/2007 | Balis et al. | |
| 2007/0059718 A1 | 3/2007 | Kapur et al. | |
| 2007/0059719 A1 | 3/2007 | Kapur et al. | |
| 2007/0059774 A1 | 3/2007 | Kapur et al. | |
| 2007/0059781 A1 | 3/2007 | Kapur et al. | |
| 2007/0099207 A1 | 5/2007 | Fuchs et al. | |
| 2007/0160503 A1 | 7/2007 | Sethu et al. | |
| 2007/0187250 A1 | 8/2007 | Huang et al. | |
| 2007/0196820 A1 | 8/2007 | Kapur et al. | |
| 2007/0231851 A1 | 10/2007 | Toner et al. | |
| 2007/0264675 A1 | 11/2007 | Toner et al. | |
| 2008/0090239 A1 | 4/2008 | Shoemaker et al. | |
| 2008/0113358 A1 | 5/2008 | Kapur et al. | |
| 2008/0124721 A1 | 5/2008 | Fuchs et al. | |
| 2008/0248499 A1 | 10/2008 | Chiu et al. | |
| 2010/0006479 A1 | 1/2010 | Reichenbach | |
| 2010/0059414 A1 | 3/2010 | Sturm et al. | |
| 2010/0297733 A1 | 11/2010 | Lin et al. | |
| 2010/0301171 A1 | 12/2010 | Wood | |
| 2010/0326916 A1 | 12/2010 | Wrazel et al. | |
| 2011/0212440 A1 | 9/2011 | Viovy et al. | |
| 2011/0213288 A1 | 9/2011 | Choi | |
| 2012/0006728 A1 | 1/2012 | Huang et al. | |
| 2012/0015835 A1 | 1/2012 | Fuchs et al. | |
| 2012/0037544 A1 | 2/2012 | Lane et al. | |
| 2012/0100560 A1 | 4/2012 | Searson et al. | |
| 2012/0115755 A1 | 5/2012 | Oh et al. | |
| 2012/0196273 A1 | 8/2012 | Huang et al. | |
| 2012/0258459 A1 | 10/2012 | Huang | |
| 2013/0143197 A1 | 6/2013 | Heyneker | |
| 2013/0209988 A1 | 8/2013 | Barber | |
| 2013/0260392 A1 | 10/2013 | Forsyth et al. | |
| 2013/0302796 A1 | 11/2013 | Fuchs et al. | |
| 2013/0324418 A1 | 12/2013 | Fuchs et al. | |
| 2014/0030788 A1 | 1/2014 | Chen et al. | |
| 2014/0154703 A1 | 6/2014 | Skelley et al. | |
| 2014/0227777 A1 | 8/2014 | Choi et al. | |
| 2014/0342375 A1 | 11/2014 | Grisham et al. | |
| 2015/0024482 A1 | 1/2015 | Frigault et al. | |
| 2015/0064153 A1 | 3/2015 | Civin et al. | |
| 2015/0299317 A1 | 10/2015 | Orentas et al. | |
| 2015/0316555 A1 | 11/2015 | Fuchs et al. | |
| 2016/0047735 A1 | 2/2016 | Grisham et al. | |
| 2016/0081314 A1 | 3/2016 | Thurston et al. | |
| 2016/0139012 A1 | 5/2016 | D'Silva et al. | |
| 2016/0168539 A1 | 6/2016 | Civin et al. | |
| 2016/0244714 A1 | 8/2016 | Spuhler | |
| 2016/0339434 A1 | 11/2016 | Toner et al. | |
| 2016/0361360 A1 | 12/2016 | Chang et al. | |
| 2017/0137515 A1 | 5/2017 | Chang et al. | |
| 2017/0166866 A1 | 6/2017 | Lliang et al. | |
| 2017/0209864 A1 | 7/2017 | Grisham et al. | |
| 2017/0224789 A1 | 8/2017 | Sonavaria et al. | |
| 2017/0248508 A1 | 8/2017 | Ward et al. | |
| 2017/0333900 A1 | 11/2017 | Grisham et al. | |
| 2018/0038876 A1* | 2/2018 | Arai | B01J 19/0093 |
| 2018/0282811 A1 | 10/2018 | Kopf-Sill et al. | |
| 2019/0062706 A1 | 2/2019 | Almaasbak et al. | |

(56) References Cited

U.S. PATENT DOCUMENTS

| | | |
|---|---|---|
| 2019/0071639 A1 | 3/2019 | Ward et al. |
| 2019/0137369 A1 | 5/2019 | D'Silva et al. |
| 2019/0366342 A1 | 12/2019 | Ward |
| 2020/0025656 A1 | 1/2020 | D'Silva |
| 2020/0025657 A1 | 1/2020 | D'Silva |
| 2020/0025669 A1 | 1/2020 | Ward |
| 2020/0056153 A1 | 2/2020 | Ward |
| 2020/0399600 A1 | 12/2020 | Ward et al. |

FOREIGN PATENT DOCUMENTS

| | | | |
|---|---|---|---|
| EP | 1585583 B1 | 4/2010 | |
| WO | WO 94/29707 A1 | 12/1994 | |
| WO | WO 2004/029221 A2 | 4/2004 | |
| WO | WO 2004/037374 A2 | 5/2004 | |
| WO | WO 2004/113877 A1 | 12/2004 | |
| WO | WO 2005/047529 A1 | 5/2005 | |
| WO | WO 2006/078470 A2 | 7/2006 | |
| WO | WO 2006/108087 A2 | 10/2006 | |
| WO | WO 2006/108101 A2 | 10/2006 | |
| WO | WO 2007/035498 A2 | 3/2007 | |
| WO | WO 2007/035585 A2 | 3/2007 | |
| WO | WO 2007/147018 A1 | 12/2007 | |
| WO | WO 2009/076560 A2 | 6/2009 | |
| WO | WO 2010/011934 | 1/2010 | |
| WO | WO 2010/129441 A2 | 11/2010 | |
| WO | WO 2011/119962 A2 | 9/2011 | |
| WO | WO 2012/024194 A2 | 2/2012 | |
| WO | WO 2014/004577 | 1/2014 | |
| WO | WO 2012/094642 | 7/2014 | |
| WO | WO 2014/116183 A1 | 7/2014 | |
| WO | WO 2014/145075 | 9/2014 | |
| WO | WO 2014/145152 | 9/2014 | |
| WO | WO 2015/084257 | 6/2015 | |
| WO | WO 2015/162211 | 10/2015 | |
| WO | WO 2015/164745 | 10/2015 | |
| WO | WO 2016/019393 A1 | 2/2016 | |
| WO | WO 2016/073481 | 5/2016 | |
| WO | WO 16/136273 | * 9/2016 | ............ C12M 1/00 |
| WO | WO 2017/035262 A1 | 3/2017 | |
| WO | WO 2018/080997 | 5/2018 | |
| WO | PCT/US2018/047426 | 8/2018 | |
| WO | WO 2019/046052 | 3/2019 | |
| WO | WO 2019/222049 | 11/2019 | |
| WO | WO 2020/014538 | 1/2020 | |

OTHER PUBLICATIONS

Tunnaini et al, Cytotherapy, 2013, 15:1406-1415. (Year: 2013).*
International Search Report for PCT/US2017/057876 filed Oct. 23, 2017.
Written Opinion of the International Searching Authority for PCT/US2017/057876 filed Oct. 23, 2017.
International Search Report for PCT/US2018/047426 filed Aug. 22, 2018.
Written Opinion of the International Searching Authority for PCT/US2018/047426 filed Aug. 22, 2018.
Agrawal, et al., "PDGF upregulates CLEC-2 to induce T regulatory cells," *Oncotarget* 6(30):28621-28632 (Sep. 2015).
Al-Fundi, et al., "New design for the separation of microorganisms using microfluidic deterministic lateral displacement," *Robotics and Computer Integrated Manufacturing* 27(2):237-244 (2011).
Beech, et al., "Sorting cells by size, shape and deformability," *Lab Chip* 12(6):1048-1051 (Mar. 2012).
Bowman, et al., "Inertia and scaling in deterministic lateral displacement," *Biomicrofluidics* 7(6) 64111:1-9 (Dec. 2013).
Böyum, "Isolation of mononuclear cells and granulocytes from human blood,", *Scand. J. Clin. Lab. Invest. Suppl.* 97:77-89 (1968).
Böyum, "Separation of White Blood Cells," *Nature* 204:793-794 (Nov. 1964).
Campos-Gonzalez, et al., "Deterministic Lateral Displacement: The Next Generation Car T-Cell Processing?" *SLAS* 23(4):338-351 (Jan. 2018).
Chen, et al., "Microfluidic chemical processing with on-chip washing by deterministic lateral displacement arrays with separator walls," *Biomicrofluidics* 9(5):054105 (Sep. 2015).
Chen, et al., "Rare cell isolation and analysis in microfluidics," *Lab Chip* 14(4):626-645 (Feb. 2014).
Chiche-Lapierre, et al., "Comparative analysis of Sepax S-100, COBE 2991, and Manual DMSO Removal Techniques From Cryopreserved Hematopoietic Stem Cell Apheresis Product," *Cytotherapy* 18(6):S47 (2016).
Chou, et al., "Sorting by diffusion: an asymmetric obstacle course for continuous molecular separation," *PNAS USA* 96(24):13762-5 (Nov. 1999).
Civin, et al., "Automated Leukocyte Processing by Microfluidic Deterministic Lateral Displacement," *Cytometry A* 89:1073-1083 (2016).
Colase, et al., "Microfluidics and coagulation biology," *Annu. Rev. Biomed. Eng.* 15:283-303 (May 2013).
Collins, et al., "Particle separation using virtual deterministic lateral displacement (vDLD)," *Lab Chip* 14(9):1595-1603 (May 2014).
Couzin-Frankel, et al., "Supply of Promising T-Cell Therapy is Strained," *Science* 356:1112 (Jun. 2017).
Davis, et al., "Deterministic hydrodynamics: taking blood apart," *PNAS USA* 103(40):14779-84 (Oct. 2006).
DiSilva, J., "Throughout Microfluidic Capture of Rare Cells from Large Volumes of Blood," A Dissertation Presented to the Faculty of Princeton University in Candidacy for the Degree of Doctor of Philosophy, (May 2016).
D'Silva, et al., "Inhibition of Clot Formation in Deterministic Lateral Displacement Arrays for Processing Large Volumes of Blood for Rare Cell Capture," *Lab Chip* 15(10):2240-2247 (May 2015).
D'Silva, "Post Geometry Design for High-Throughput Harvesting of Nucleated Cells from Blood with Minimal Erythrocyte Contamination Using DLD Arrays," Chapter 4: 53-113, Ph.D. Dissertation, Princeton University ((May 2016).
Feng, et al., "Maximizing particle concentration in deterministic lateral displacement arrays," *Biomicrofluidics* 11:024121 (published online Apr. 2017).
Fiorini, et al., "Disposable microfluidic devices: fabrication, function and application," *BioTechniques* 38(3):429-446 (Mar. 2005).
Fousek, et al., "The Evolution of T-cell Therapies for Solid Malignancies," *Clinical Cancer Research* 21(5):3384-3392 (Aug. 2015).
Gervais, Capillary Microfluidic Chips for Point-of-Care Testing: from Research Tools to Decentralized Medical Diagnostics. Lausanne: EPFL, 2011.
Han, et al., "Separation of long DNA molecules in a microfabricated entropic trap array," *Science* 288(5468):1026-1029 (May 2000).
Hokland, et al., "The Isopaque-Ficoll Method Re-evaluated: Selective Loss of Autologous Rosette-forming Lymphocytes During Isolation of Mononuclear Cells from Human Peripheral Blood," *Scand. J. Immunol.* 11(3):353-356 (Mar. 1980).
Holmes, et al., "Separation of blood cells with differing deformability using deterministic lateral displacement," *Interface Focus* 4(6):20140011 (Dec. 2014).
Huang, et al., "A Microfluidics approach for the isolation of nucleated red blood cells (NRBCs) from the peripheral blood of a pregnant women," *Prenat. Diagn.* 28(10):892-899 (Oct. 2008).
Huang, et al., "A DNA prism for high-speed continuous fractionation of large DNA molecules," *Nat. Biotechnol.* 20(10):1048-1051 (Oct. 2002).
Huang, et al., "Role of molecular size in ratchet fractionation," *Phys Rev Lett* 89(17)178301 (Oct. 2002).
Huang, et al., "Continuous particle separation through deterministic lateral displacement," *Science* 304(5673):987-990 (May 2004).
Inglis, et al., "Critical particle size for fractionation by deterministic lateral displacement," *Lab Chip* 6(5):655-658 (May 2006).
Inglis, et al., "Determining blood cell size using microfluidic hydrodynamics," *J. Immunol. Methods* 329(1-2):151-156 ((Jan. 2008).
Inglis, et al., "Scaling deterministic lateral displacement arrays for high throughput and dilution-free enrichment of leukocytes," *J. Micromech. Microeng.* 21:054024 (2011).

(56) References Cited

OTHER PUBLICATIONS

Jiang, et al., "Fractionation by shape in deterministic lateral displacement microfluidic devices," *Microfluidics and Nanofluidics* 19(2):427-434 (Aug. 2015).
Johnson, et al., "Driving Gene-engineered T-cell Immunotherapy of Cancer," *Cell Res.* 27:38-58 (2017).
Koesdjojo, et al., "DLD Microfluidic Purification and Characterization of Intact and Viable Circulating Tumor Cells in Peripheral Blood," *AACR Annual Meeting* Abstract #3956 (2016).
Kurihara, et al., "Imaging Brain Tumors by Targeting Peptide Radiopharmaceuticals through the Blood-Brain Barrier," *Cancer Research* 59(24):6159-6163 (Dec. 1999).
Levine, et al., "Global Manufacturing of CAR T-cell Therapy," *Mol. Therapy: Meth. Clin. Dev.* 4:92-101 (2017).
Li, et al., "Comparison of anti-CD3 and anti-CD28-eoated beads with soluble anti-CD3 for expanding Human T-cells: Differing impact on CD8 T-cell phenotype and responsiveness to restimulation," *J. Transl. Med.* 8:104-118 (2010).
Liu, et al., "Rapid isolation of cancer cells using microfluidic deterministic lateral displacement structure," *Biomicrofluidics* 7(1):11801 (Jan. 2013).
Liu, et al., "High throughput capture of circulating tumor cells using an integrated microfluidic system," *Biosensors and Bioelectronics* 47:113-119 (2013).
Loutherback, et al., "Deterministic Microfluidic Ratchet," *Physical Review Letters* 102(4):045301 (Jan. 2009).
Loutherback, et al., "Deterministic separation of cancer cells from blood at 10mL/min," *API Advances* 2(4):42107 (Dec. 2012).
Loutherback, et al., "Improved performance of deterministic lateral displacement arrays with triangular posts," *Microfluidics Nanofluidics* 9:1143-1149 (2010).
Loutherback, et al., "Critical size, dynamic range and throughput improvements in sorting by deterministic lateral displacement enabled by triangular posts," Presented at the Symposium of the Materials Research Society, San Francisco, CA (Apr. 2009).
Loutherback, K., "Microfluidic Devices for High Throughput Cell Sorting and Chemical Treatment," A Dissertation Presented to the Faculty of Princeton University, (2011).
Mahnke, et al., "The who's who of T-eell differentiation: Human memory T-cell subsets," *Eur. J. Immunol.* 43:2797-2809 (2013).
Marktkamcham, et al., "The Effects of Anti-CD3/CD28 Coated Beads and IL-2 on Expanded T Cell for Immunotherapy," *Adv. Clin. Exp. Med.* 25:821-828 (2016).
McGrath, et al., "Deterministic lateral displacement for particle separation: a review," *Lab Chip* 14(21):4139-4158 (Sep. 2014).
Morton, et al., "Crossing microfluidic streamlines to lyse, label and wash cells," *Lab Chip* 8(9):1448-1453 (Sep. 2008).
National Cell Manufacturing Consortium. Achieving Large-Scale, Cost-Effective, Reproducible Manufacturing of High Quality Cells. A Technology Roadmap to 20205. (Feb. 2016).
Oakey, et al., "Laminar Flow-Based Separations at the Microscale," *Biotechnology Progress* 1439-1442 (2002)
Powell, et al., "Efficient clinical-scale enrichment of lymphocytes for use in adoptive immunotherapy using a modified counterflow centrifugal elutriation program," *Cytotherapy* 11(7):923-935 (2009).
Radisic, et al., "Micro- and nanotechnology in cell separation," *International Journal of Nanomedicine* 1(1):3-14 (2006).
Ranjan, et al., "DLD pillar shape design for efficient separation of spherical and non-spherical bioparticles," *Lab Chip* 14(21):4250-4262 (Sep. 2014).
Reddy, et al., "Isolation of Stem Cells from Human Umbilical Cord Blood," in Vemuri (eds) Stem Cell Assays. Methods in Molecular Biology vol. 407, Human Press, pp. 149-163 (2007).
Sadelain, et al., "Therapeutic T cell engineering," *Nature* 545:423-431 (May 2017).
Sommanson, et al., "Deterministic lateral separation of cells," Lund University. Master's Thesis, (2006).
Stroncek, et al., "Counter-flow elutriation of clinical peripheral blood mononuclear cell concentrates for the production of dendritic and T cell therapies," *J. Transl. Med.*12:241 (2014).
Terumobct. Elutra® Cell Separation System, Enrichment of Lymphocytes from Apheresis Residues.
Toner, et al., "Blood-on-a-Chip," *Annu. Rev. Biomed. Eng.* 7:77-103, C1-C3 (2005).
Trickett, et al., "T-cell Stimulation and Expansion Using Anti-CD3/CD28 Beads," *J/ Immunol. Meth.* 275:251-255 (Apr. 2003).
Turner, et al., "Confinement-induced entropic recoil of single DNA molecules in a nanofluidic structure," *Phys Rev Lett* 88(12):128103 (Mar. 2002).
Vonderheide, et al., "Engineering T cells for cancer: our synthetic future," *Immunol. Rev.* 257:7-13 (2014).
Wang, et al., "Clinical manufacturing of CAR T cells: a foundation of a promising therapy," *Mol. Ther. Oncolytics* 3:16015 (2016).
Yang, et al., "Microfluidic device fabrication by thermoplastic hot-embossing," *Methods Mol. Biol.* 949:115-123 (2013).
Yi, et al., "Microfluidics technology for manipulation and analysis of biological cells," *Analytica Chimica Acta* 560:1-23 (2006).
Yu, et al., "A Microfluidic Approach for Whole Blood Leucocytes Isolation for Leucocytes Immunophenotyping by Flow Cytometry," Congress Center Leipzig, Lepzig, Germany, Poster B228, (Jun. 2012).
Zeming, et al., "Asymmetrical Deterministic Lateral Displacement Gaps for dual Functions of Enhanced Separation and Throughput of Red Blood Cells," *Sci. Rep.* 6:22934 (Mar. 2016).
Zeming, et al., "Rotational separation of non-spherical bioparticles using l-shaped pillar arrays in a microfluidic device," *Nat. Commun.* 4:1625 (2013).
Zhang, et al., "Applications of Microfluidics in Stem Cell Biology," *Bionanoscience* 2(4):277-286 (Dec. 2012).
Zhang, et al., "Behavior of rigid and deformable particles in deterministic lateral displacement devices with different post shapes," *J. Chem. Phys.* 143(24):243145 (Dec. 2015).
Zhang, et al., "Optimized DNA electroporation for primary human T cell engineering," *BMC Biotechnology* 18:4 (2018).
Zheng, et al., "Deterministic lateral displacement MEMS device for continuous blood cell separation," Micro Electro Mechanical Systems, 2005. 18th IEEE International Conference.
Zhu, et al., "Platelets Provoke Distinct Dynamics of Immune Response by Differentially Regulating CD4$^+$ T-cell Proliferation," *J. Throm. Haem.* 12:1156-1165 (2014).
U.S. Appl. No. 14/774,260, filed Sep. 10, 2015, 2016/0139012 A1, May 19, 2016, D'Silva, et al.
U.S. Appl. No. 14/774,268, filed Sep. 10, 2015, 2016/0047735 A1, Feb. 18, 2016, Grisham, et al.
U.S. Appl. No. 14/941,957, filed Nov. 16, 2015, 2016/0168539 A1, Jun. 16, 2016, Civin, et al.
U.S. Appl. No. 15/329,753, filed Jan. 27, 2017, 2017/0209864 A1, Jul. 27, 2017, Grisham, et al.
U.S. Appl. No. 15/478,405, filed Apr. 4, 2017, 2017/0333900 A1, Nov. 23, 2017, Grisham, et al.
U.S. Appl. No. 15/595,548, filed May 15, 2017, 2017/0248508 A1, Aug. 31, 2017, Ward, et al.
U.S. Appl. No. 16/108,365, filed Aug. 23, 2018, 2019/0071639 A1, Mar. 7, 2019, Ward, et al.
U.S. Appl. No. 16/123,056, filed Sep. 6, 2018, 2019/0137369 A1, May 9, 2019, D'Silva, et al.
U.S. Appl. No. 16/343,754, filed Apr. 20, 2019, Not yet published, NA, Ward, et al.
U.S. Appl. No. 16/587,022, filed Sep. 29, 2019, Not yet published, NA, D'Silva, et al.
U.S. Appl. No. 16/587,057, filed Sep. 30, 2019, Not yet published, NA, Ward, et al.
U.S. Appl. No. 16/588,137, filed Sep. 30, 2019, Not yet published, NA, D'Silva, et al.
International Preliminary Report on Patentability for PCT/US2018/047426 filed Aug. 22, 2018, corresponding to the present application and U.S. Appl. No. 16/108,365.
Gattinoni, et al., "Moving T memory stem cells to the clinic," *Blood* 121(4):567-569 (Jan. 2013).
Kanwar, et al., "Microfluidic device (ExpoChip) for on-chip isolation, quantification and characterization of circulating exosomes," *Lab on a Chip* 14:1891-1900 (Mar. 2014).

(56) References Cited

OTHER PUBLICATIONS

Ward, et al., "Efficient Production of T-Central Memor Cells from Apheresis Product Using Microfluidic Chips," poster #290 for Annual Meeting of the International Society for Cellular Therapy, published in *Cytotherapy* 20(5) *Suppl.* p. S98 (May 2018).
International Preliminary Report on Patentability for PCT/US2017/057876 filed Oct. 23, 2017, corresponding to copending U.S. Appl. No. 16/343,754.
Office Action for copending U.S. Appl. No. 16/108,365, dated Dec. 3, 2019.
Amendment & Response filed Jun. 1, 2020 for copending U.S. Appl. No. 16/108,365.
Notice of Allowance dated Jul. 13, 2020 for copending U.S. Appl. No. 16/108,365.
European Search Report and Opinion for EP 17865812.6 (counterpart of related U.S. Appl. No. 16/343,754) dated Mar. 12, 2020.
Claims in EP 17865812.6 as of Mar. 12, 2020.
Inglis, et al., "Microfluidic device for label-free measurement of platelet activation," *Lab on a Chip* 8(6):925-931 (Jan. 2008).
Li, et al., "On-Chip Continuous Blood Cell Subtype Separation by Deterministic Lateral Displacement," Proceedings of the 2nd IEEE International Conference on Nano/Micro Engineered and Molecular Systems; (Jan. 16-19, 2007).
Preliminary Amendment for related copending U.S. Appl. No. 17/009,797, filed Sep. 2, 2020.
Response to the European Search Opinion of Mar. 2, 2020, for related European application EP 17865812.6 filed on Sep. 10, 2020.
Response to Rule 161 and 162 of the EPO for related European application EP 18851908.6, filed on Sep. 28, 2020.
U.S. Appl. No. 17/009,797, filed Sep. 2, 2020, NA, NA, Ward.
Non Final Office Action for copending U.S. Appl. No. 17/009,797 dated Jan. 21, 2020.
U.S. Appl. No. 17/192,691, filed Mar. 4, 2021, Ward.

* cited by examiner

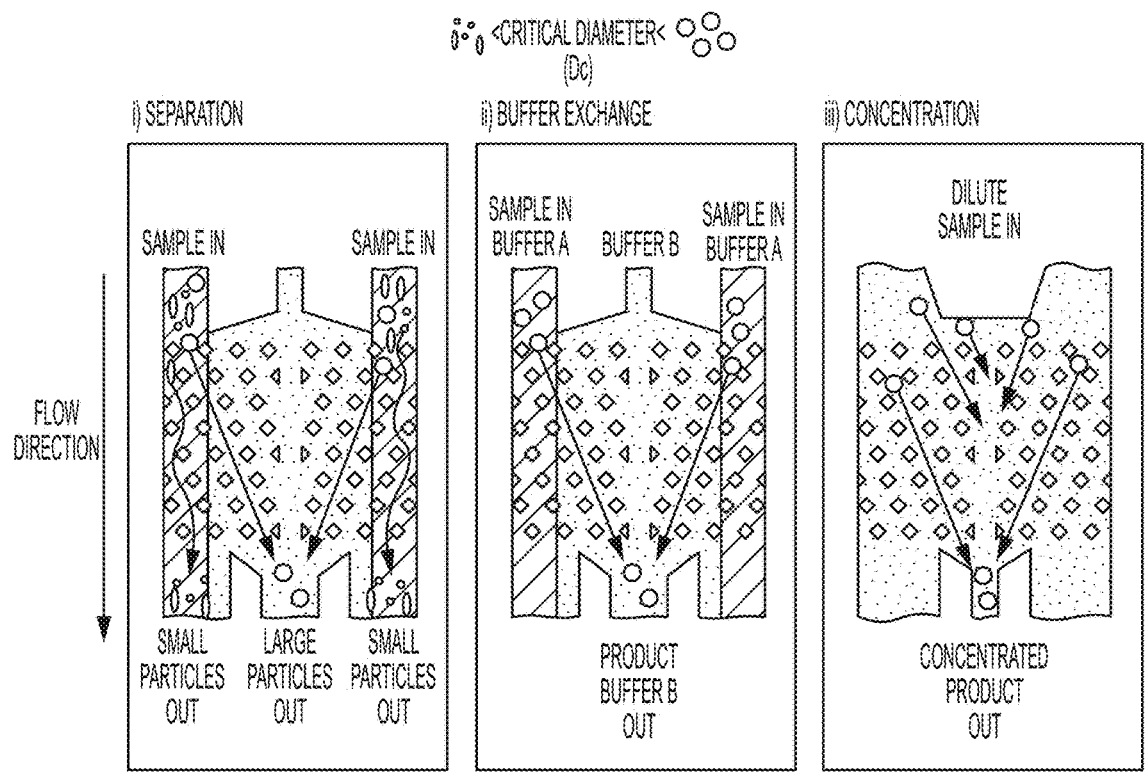
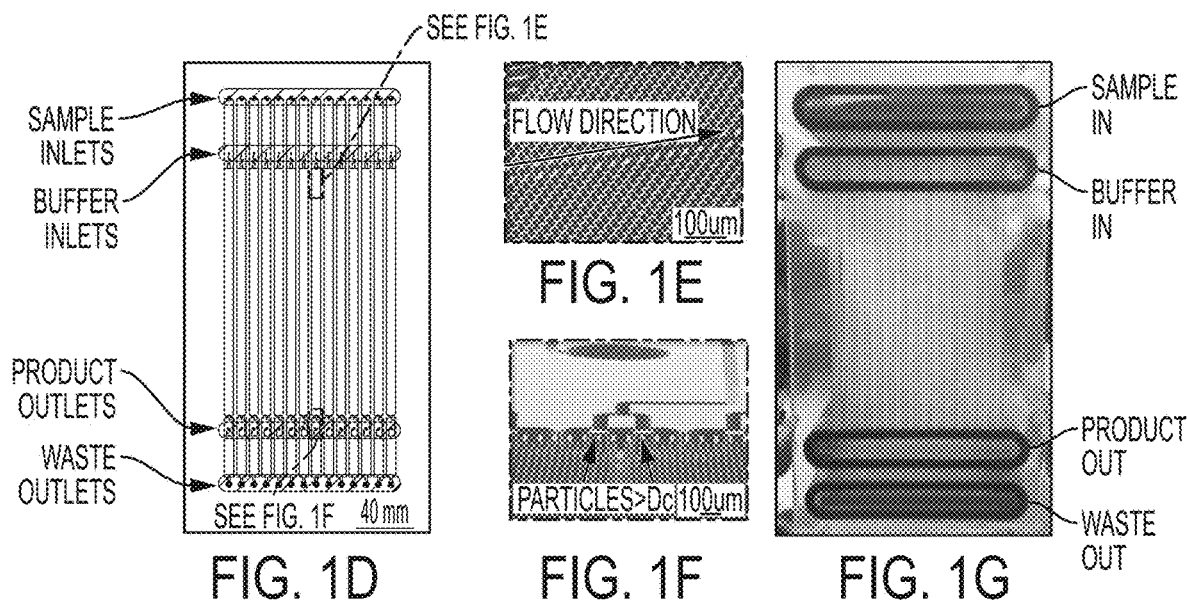

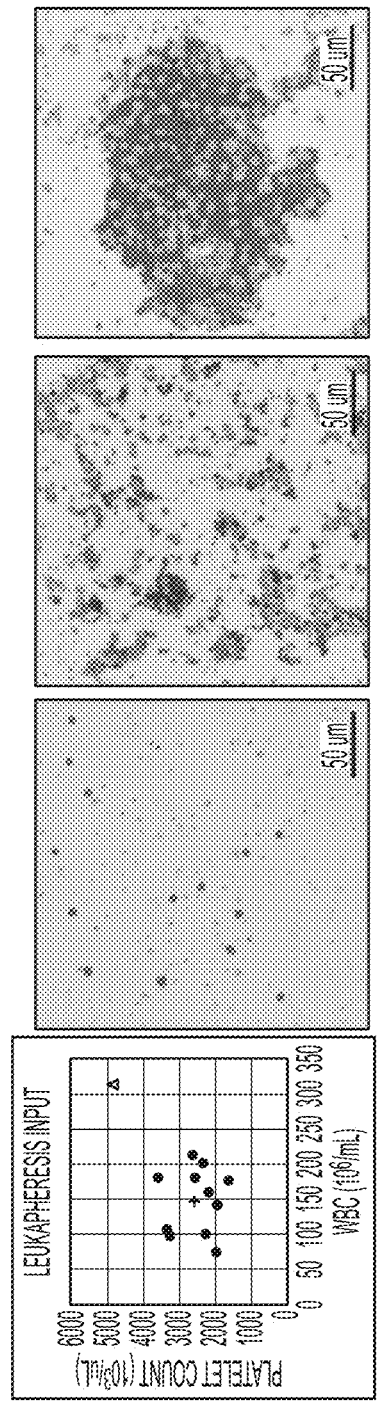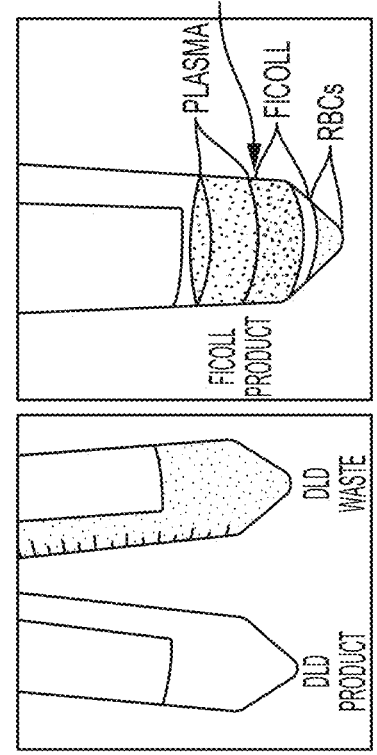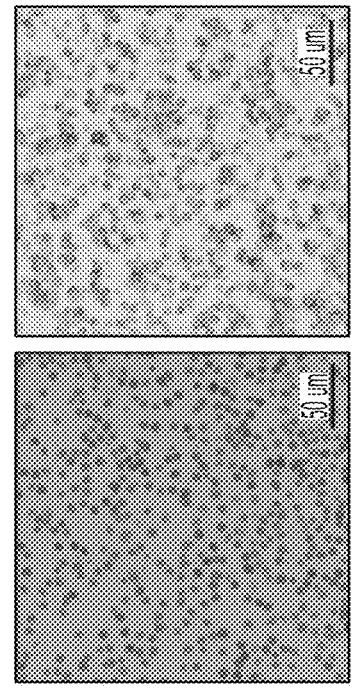

METHODS FOR PREPARING THERAPEUTICALLY ACTIVE CELLS USING MICROFLUIDICS

CROSS REFERENCE TO RELATED APPLICATIONS

This application is a continuation of U.S. Ser. No. 16/108,365, filed on Aug. 22, 2018, which issued as U.S. Pat. No. 10,844,353 on Nov. 24, 2020, and which claims the benefit of U.S. Provisional Patent Application No. 62/553,723, filed on Sep. 1, 2017; the benefit of U.S. Provisional Patent Application No. 62/567,553, filed on Oct. 3, 2017; the benefit of Provisional Patent Application No. 62/635,304, filed on Feb. 26, 2018; and the benefit of Provisional Patent Application No. 62/656,939, filed on Apr. 12, 2018; and which, in addition, is a continuation-in-part of PCT/US2017/057876, filed on Oct. 23, 2017. These prior applications are all incorporated by reference herein in their entireties.

STATEMENT AS TO FEDERALLY SPONSORED RESEARCH

This invention was made with government support under Grant No. CA174121 and No. HL110574 awarded by the National Institutes of Health. The government has certain rights in the invention.

FIELD OF THE INVENTION

The present invention is directed primarily to methods of preparing cells and compositions for therapeutic uses. The methods employ microfluidic devices that separate cells based on size.

BACKGROUND OF THE INVENTION

Cell therapy, and especially CAR-T cell therapy, has demonstrated extraordinary efficacy in treating B-cell diseases such as B-acute lymphoid leukemia (B-ALL) and B-Cell Lymphomas. As a result, the demand for autologous therapies has increased dramatically and development efforts have broadened to focus on cancers characterized by solid tumors, such as glioblastomas (Vonderheide, et al., *Immunol. Rev.* 257:7-13 (2014); Fousek, et al., *Clin. Cancer Res.* 21:3384-3392 (2015); Wang, et al., *Mol. Ther. Oncolytics* 3:16015 (2016); Sadelain, et al., *Nature* 545:423-431 (2017)). Targeted gene editing with CRISPR/Cas-9 in focused populations of autologous cells, such as stem cells, may further fuel demand (Johnson, et al., *Cancer Cell Res.* 27:38-58 (2017)).

The preparation of cells for personalized therapy is usually a labor-intensive process that relies on procedures adapted from blood banking or protein bioprocessing procedures which are poorly suited for therapeutic applications. Cell losses associated with processing steps are typically substantial (Hokland, et al., *Scand. J. Immunol.* 11:353-356 (1980); Stroncek, et al., *J. Transl. Med.* 12:241 (2014)), in part because of processes that use preparations that achieve cell specific separations (Powell, et al., *Cytotherapy* 11:923-935 (2009); TerumoBCT. ELUTRA Cell Separation System. Manufacturer recommendations for the Enrichment of Lymphocytes from Apheresis Residues) but do so at the expense of cell viability and yield (Chiche-Lapierre, Cytotherapy 18(6):547 (2016)). Thus, there is a need for more efficient processes.

SUMMARY OF THE INVENTION

The present invention is directed, inter alia, to methods of collecting and rapidly processing cells, particularly cells that have therapeutic uses. Many of the methods rely on Deterministic Lateral Displacement (DLD), a process that involves flowing a sample through a microfluidic device containing a specifically designed array of microposts that are tilted at a small angle from the direction of fluid flow (Davis, et al., *Proc. Natl. Acad. Sci. USA* 103:14779-14784 (2006); Inglis, et al., *Lab Chip* 6:655-658 (2006); Chen, et al., *Biomicrofluidics.* 9(5):054105 (2015)). Cells larger than the target size of the micropost array may be gently deflected ("bumped") by the microposts into a stream of clean buffer, effectively separating them from smaller, non-deflected cells and particles, while simultaneously washing the cells in a process that is non-injurious. Advantageous characteristics of DLD with respect to cell processing are described in Table 1:

TABLE 1

| Intrinsic Properties of DLD and Their Implications for Cell Processing | | |
|---|---|---|
| DLD Feature | Enablement | Implications |
| Uniform feature and gap size | Fractionate complex mixtures based on size with ability to discriminate particles to within ~0.5 μm. | Uniform and gentle de-bulking of platelet and RBC from blood products without centrifugation up to 99.99% efficiency Eliminates open solutions such as Ficoll, and avoids need for harsh hypertonic solutions (Elutriation). |
| | Ability to mix different Dc within the same device | Use of sequential cut-offs to manage highly heterogeneous fractionations |
| | Cell Washing & Buffer Exchange | Cell Washing >99.9% removal in single pass Potential to improve and remove cell culture while maintaining closed system ensuring viable cells. |
| | Concentration | Concentration of cells in culture to make downstream processing seamless. |
| Closeable fluid path | Simple, sterilizable | Minimize reagent expense without requiring open centrifugation or transfer losses. Ideal for single use, especially patient specific therapeutic device. |
| Low Dead Volume | <50 μl Dead volume per 14 lane chip | Excellent cell recovery |

TABLE 1-continued

Intrinsic Properties of DLD and Their Implications for Cell Processing

| DLD Feature | Enablement | Implications |
| --- | --- | --- |
| Requires only positive pressure | Hands free operation | Potential to automate complex cell handling and liquid addition exchange processes within a closed system |

Methods for Engineering Target Cells

In its first aspect, the invention is directed to a method of genetically engineering a population of target cells. This is done by isolating the target cells from a crude fluid composition by performing Deterministic Lateral Displacement (DLD) on a microfluidic device. The device is characterized by the presence of at least one channel which extends from a sample inlet to one or more fluid outlets, and which is bounded by a first wall and a second wall opposite from the first wall. An array of obstacles is arranged in rows in the channel, with each subsequent row of obstacles being shifted laterally with respect to a previous row. The obstacles are disposed in a manner such that, when the crude fluid composition is applied to an inlet of the device and passed through the channel, target cells flow to one or more collection outlets where an enriched product is collected, and contaminant cells or particles flow to one or more waste outlets that are separate from the collection outlets. Once the target cells have been purified using the device, they are transfected or transduced with nucleic acids designed to impart upon the cells a desired phenotype, e.g., to express a chimeric molecule (preferably a protein that makes the cells of therapeutic value). The population of cells may then be expanded by culturing in vitro. When cultured and expanded, the yield of recombinantly engineered target cells exhibiting the desired phenotype is preferably at least 10% greater than identical cells not subjected to DLD (and particularly cells that have been exposed to Ficoll centrifugation but not DLD), and more preferably at least 20, 30, 40, or 50% greater.

In a preferred embodiment, the crude fluid composition is blood or, more preferably, a preparation of leukocytes that has been obtained by performing apheresis or leukapheresis on the blood of a patient. Preferred target cells include T cells, B-cells, NK-cells, monocytes and progenitor cells, with T cells (especially natural killer T cells) being the most preferred. Apart from leukocytes, other types of cells, e.g., dendritic cells or stem cells, may also serve as target cells.

In general, crude fluid compositions containing target cells will be processed without freezing (at least up until the time that they are genetically engineered), and at the site of collection. The crude fluid composition will preferably be the blood of a patient, and more preferably be a composition containing leukocytes obtained as the result of performing apheresis or leukapheresis on such blood. However, the term "crude fluid composition" also includes bodily fluids such as lymph or synovial fluid as well as fluid compositions prepared from bone marrow or other tissues. The crude fluid composition may also be derived from tumors or other abnormal tissue.

Although it is not essential that target cells be bound to a carrier before being genetically engineered, it is preferred that, either before or after DLD is first performed (preferably before) they be bound to one or more carriers. The exact means by which this occurs is not critical to the invention but binding should be done "in a way that promotes DLD separation." This term, as used in the present context, means that the method must ultimately result in binding that exhibits specificity for a particular target cell type, that provides for an increase in size of the complex relative to the unbound cell of at least 2 μm (and alternatively at least 20, 50, 100, 200, 500 or 1000% when expressed as a percentage) and, in cases where therapeutic or other uses require free target cells, that allow the target cell to be released from complexes by chemical or enzymatic cleavage, chemical dissolution, digestion, due to competition with other binders, by physical shearing, e.g., using a pipette to create shear stress, or by other means.

In a preferred embodiment, the carriers have on their surface an affinity agent (e.g., an antibody, activator, hapten, aptamer, nucleic acid sequence, or other compound) that allows the carriers to bind directly to the target cells with specificity. Alternatively, there may be an intermediary protein, cell, or other agent that binds to both the target cell and carrier with specificity. For example, antibodies may be used that recognize surface antigens on target cells and that also bind with specificity to carriers (e.g., due to that presence of a second antibody on the carrier surface, avidin/biotin binding or some other similar interaction). In addition, target cells may sometimes interact with specificity with other cells to form a complex and in so doing, the other cells may serve as a biological carrier, i.e., they may increase the effective size of the target cell and thereby facilitate its separation from uncomplexed cells. For example, human T cells may interact with sheep erythrocytes or autologous human erythrocytes to form a rosette of cells that can then be purified as a complex. Alternatively, other carriers may bind with specificity to cells in such a rosette to further promote a size based separation.

As used in this context, the word "specificity" means that at least 100 (and preferably at least 1000) target cells will be bound by carrier in the crude fluid composition relative to each non-target cell bound. In cases where the carrier binds after DLD, the binding may occur either before the target cells are genetically engineered or after.

Binding of the carriers may help to stabilize cells, activate them (e.g., to divide) or help to facilitate the isolation of one type of cell from another. As suggested above, the binding of carriers to cells can take place at various times in the method, including during the time that cells are being obtained. In order to improve separation, carriers may be chosen such that the binding of a single carrier to a cell results in a carrier-cell complex that is substantially larger than the size of the cell alone. Alternatively carriers may be used that are smaller that the target cell. In this case, it is preferred that several carriers bind with specificity to a cell, thereby forming a complex having one cell and multiple carriers. During DLD, complexed target cells may separate from uncomplexed cells having a similar size and provide a purification that would otherwise not occur.

In order to achieve such separation, the diameter of the complex should preferably be at least 20% larger than the uncomplexed target cells and more preferably at least 50% larger, at least twice as large or at least ten times as large. As stated above this increase in size may be either due to the binding of a single large carrier to target cells or due to the binding of several smaller carriers. This may be accomplished using: a) only carriers with a diameter at least as large (or in other embodiments, at least twice as large or at least ten times as large) as that of the target cells; b) only carriers with a diameter no more than 50% (or in other embodiments, no more than 25% or 15%) as large as that of the target cells; or c) mixtures of large and small carriers with these size characteristics (e.g., there may be one group of carriers with a diameter at least as large (or at least twice or ten times as large) as the target cells and a second group of carriers with a diameter no more than 50% (or no more than 25% or 15%) as large as that of the target cells. Typically, a carrier will have a diameter of 1-1000 μm (and often in the range of 5-600 or 5-400 μm). Ideally, the complexes will be separated from other cells or contaminants by DLD on a microfluidic device having an array of obstacles with a critical size lower than the size of the complexes but higher than the size of uncomplexed non-target cells or contaminants.

In addition carriers may act in a way that "complements DLD separation" rather than directly promoting separation by this technique. For example, a carrier (e.g., as Janus or Strawberry-like particles) may comprise two or more discrete chemical properties that support and confer actionable differential non-size related secondary properties, such as chemical, electrochemical, or magnetic properties, on the cells that they bind with and these properties may be used in downstream processes. Thus, the particles may be used to facilitate magnetic separation, electroporation, or gene transfer. They may also confer advantageous changes in cellular properties relating to, for example, metabolism or reproduction.

In a particularly important embodiment, the binding of carriers may be used as a means of separating a specific leukocyte, especially T cells, including natural killer T cells, from other leukocytes, e.g., granulocytes and monocytes, and/or from other cells. This may be done, for example, in a two step process in which DLD is performed on target cells that are not bound to a carrier using an array of obstacles with a critical size smaller than the cells and also performed on complexes comprising target cells and carriers using an array of obstacles with a critical size smaller than the complexes but larger than the uncomplexed cells. The DLD steps can be performed in either order, i.e., DLD may be performed on the complexes before or after being performed on uncomplexed target cells.

No more than four hours (and preferably no more than three, two or one hour(s)) should elapse from the time that the obtaining of crude fluid composition is completed until the target cells are first bound to carriers. In addition, no more that five hours (and preferably no more than four, three or two hours) should elapse from the time that the obtaining of crude fluid composition is completed until the first time that target cells are transfected or transduced.

In a particularly preferred embodiment, the target cells in the methods described above are T cells (especially natural killer T cells and memory T cells) and these are engineered to express chimeric antigen receptors on their surface. The procedures for making these CAR T cells are described more specifically below.

Methods for Making CAR T Cells

The invention includes a method of producing CAR T cells by obtaining a crude fluid composition comprising T cells (especially natural killer T cells and memory T cells) and performing DLD on the composition using a microfluidic device. Generally, the crude fluid composition comprising T cells will be an apheresis or leukapheresis product derived from the blood of a patient and containing leukocytes.

The microfluidic device must have at least one channel extending from a sample inlet to one or more fluid outlets, wherein the channel is bounded by a first wall and a second wall opposite from the first wall. An array of obstacles is arranged in rows in the channel, each subsequent row of obstacles being shifted laterally with respect to a previous row. These obstacles are disposed in a manner such that, when the crude fluid composition comprising T cells is applied to an inlet of the device and fluidically passed through the channel, the T cells flow to one or more collection outlets where an enriched product is collected and other cells (e.g., red blood cells, and platelets) or other particles of a different (generally smaller) size than the T cells flow to one or more waste outlets that are separate from the collection outlets. Once obtained, the T cells are genetically engineered to produce chimeric antigen receptors (CARs) on their surface using procedures well established in the art. These receptors should generally bind antigens that are on the surface of a cell associated with a disease or abnormal condition. For example, the receptors may bind antigens that are unique to, or overexpressed on, the surface of cancer cells. In this regard, CD19 may sometimes be such an antigen.

The genetic engineering of CAR-expressing T cells will generally comprise transfecting or transducing T cells with nucleic acids and, once produced, the CAR T cells may be expanded in number by growing the cells in vitro. Activators or other factors may be added during this process to promote growth, with IL-2 and IL-15 being among the agents that may be used. The yield of T cells expressing chimeric receptors on their surface after DLD, recombinant engineering and expansion, should, in some embodiments be at least 10% greater than T cells prepared in the same manner but not subjected to DLD and preferably at least 20, 30, 40 or 50% greater. Similarly, in some embodiments, the yield of T cells expressing the chimeric receptors on their surface should be at least 10% greater than T cells isolated by Ficoll centrifugation and not subjected to DLD and preferably at least 20, 30, 40 or 50% greater.

Chimeric receptors will typically have a) an extracellular region with an antigen binding domain; b) a transmembrane region and c) an intracellular region. The cells may also be recombinantly engineered with sequences that provide the cells with a molecular switch that, when triggered, reduce CAR T cell number or activity. In a preferred embodiment, the antigen binding domain is a single chain variable fragment (scFv) from the antigen binding regions of both heavy and light chains of a monoclonal antibody. There is also preferably a hinge region of 2-20 amino acids connecting the extracellular region and the transmembrane region. The transmembrane region may have CD3 zeta, CD4, CD8, or CD28 protein sequences and the intracellular region should have a signaling domain, typically derived from CD3-zeta, CD137 or a CD28. Other signaling sequences may also be included that serve to regulate or stimulate activity.

After obtaining the crude fluid composition comprising T cells, or during the time that they are being collected, the T cells may, for the reasons discussed above, be bound to one or more carriers in a way that promotes DLD separation. This will preferably take place before performing DLD. However, it may also occur after performing DLD and either before or after cells are transfected or transduced for the first time. In a preferred embodiment, the carriers should comprise on their surface an affinity agent (e.g., an antibody, activator, hapten or aptamer) that binds with specificity to T cells, preferably natural killer T cells. The term "specificity" as used in this context means that the carriers bind preferentially to the desired T cells as compared to any other cells in the composition. For example, the carriers may bind to 100 or 1000 CD8+ T cells for each instance in which it binds a different type of cell.

Carriers may, in some embodiments, have a spherical shape and be made of either biological or synthetic material, including collagen, polysaccharides including polystyrene, acrylamide, alginate and magnetic material. In addition, carriers may act in a way that complements DLD separation.

In order to aid in achieving a separation, the diameter of the complex formed between T cells and carriers should preferably be at least 20% larger than the uncomplexed T cells and preferably at least 50% larger, at least twice as large or at least ten times as large. This increase in size may be either due to the binding of a single large carrier to the cells or due to the binding of several smaller carriers. Binding may involve using: a) only carriers with a diameter at least as large (or in other embodiments, at least twice as large or at least ten times as large) as that of the T cells; b) only carriers with a diameter no more than 50% (or in other embodiments, no more than 25% or 15%) as large as that of the T cells; or c) mixtures of large and small carriers with these size characteristics (e.g., there may be one group of carriers with a diameter at least as large (or at least twice or ten times as large) as the T cells and a second group of carriers with a diameter no more than 50% (or no more than 25% or 15%) as large as that of the T cells. Typically a carrier will have a diameter of 1-1000 µm (and often in the range of 5-600 or 5-400 µm). Ideally, the complexes will be separated from uncomplexed cells or contaminants by DLD on a microfluidic device having an array of obstacles with a critical size lower than the size of the complexes but higher than the size of uncomplexed non-target cells or contaminants.

As discussed above in connection with target cells, the purification of T cells may involve a two step process. For example, DLD may be performed on T cells that are not bound to carriers using an array of obstacles with a critical size smaller than the T cells. A composition containing the separated T cells together with other cells or particles may then be recovered and bound to one or more carriers in a way that promotes DLD separation and in which T cells are bound with specificity. The complexes thereby formed may then be separated on an array of obstacles with a critical size smaller than the complexes but larger than uncomplexed cells. In principle, the DLD steps could be performed in either order, i.e., it might be performed on the complexes first or on the uncomplexed T cells first.

Preferably, no more than four hours (and, more preferably, no more than three, two or one hour(s)) should elapse from the time that the obtaining of the crude fluid composition comprising T cells is completed (e.g., from the time that apheresis or leukapheresis is completed) until the T cells are bound to a carrier. In addition, no more than five hours (and preferably no more than four hours, three or two hours) should elapse from the time that the obtaining of T cells is completed until the first time that T cells are transfected or transduced. Ideally, all steps in producing the CAR T cells are performed at the same facility where the crude fluid composition comprising T cells is obtained and all steps are completed in no more than four (and preferably no more than three) hours and without the cells being frozen.

Treating Cancer, Autoimmune Disease or Infectious Disease Using CAR T Cells

In another aspect, the invention is directed to a method of treating a patient for cancer, an autoimmune disease or an infectious disease by administering CAR T cells engineered to express chimeric antigen receptors recognizing cancer cell antigens, or antigens on cells responsible for, or contributing to, autoimmune or infectious disease. The CAR T cells may be made using the methods discussed in the section above, i.e., by obtaining a crude fluid composition comprising T cells (preferably a leukocyte-containing apheresis or leukapheresis product derived from the patient) and then performing DLD on the composition using a microfluidic device. The CAR T cells (preferably natural killer T cells, and memory T cells) recovered in this manner are then expanded by growing the cells in vitro. Finally, the cells are administered to a patient, which should generally be the same patient that gave the blood from which the T cells were isolated.

Preferably, the yield of T cells expressing chimeric receptors on their surface after DLD, recombinant engineering and expansion is at least 10% greater than T cells prepared in the same manner but not subjected to DLD and more preferably at least 20, 30, 40 or 50% greater. For example, the yield of T cells expressing the chimeric receptors on their surface may be at least 10% greater than T cells isolated by Ficoll centrifugation and not subjected to DLD and preferably at least 20, 30, 40 or 50% greater.

Chimeric receptors will typically have at least: a) an extracellular region with an antigen binding domain; b) a transmembrane region and c) an intracellular region. The cells may also be recombinantly engineered with sequences that provide the cells with a molecular switch that, when triggered, reduce CAR T cell number or activity. In a preferred embodiment, the antigen binding domain is a single chain variable fragment (scFv) from the antigen binding regions of both heavy and light chains of a monoclonal antibody. There is also preferably a hinge region of 2-20 amino acids connecting the extracellular region and the transmembrane region. The transmembrane region itself may have CD3 zeta, CD4, CD8, or CD28 protein sequences and the intracellular region will have a signaling domain, typically derived from CD3-zeta and/or a CD28 intracellular domain. Other signaling sequences may also be included that serve to regulate or stimulate activity.

After obtaining the crude fluid composition or during the time the crude fluid composition is being collected, T cells present in the composition may be bound to one or more carriers in a way that promotes or complements DLD separation. This will preferably take place before performing DLD. However, it may also occur after performing DLD and either before or after the cells are genetically engineered. Preferably the binding will promote DLD separation and the carriers will comprise on their surface an antibody, activator or other agent that binds with specificity to T cells, especially natural killer T cells. The term "specificity" as used in this context means that the carrier will be bound preferentially to the desired T cells as compared to any other cells in the composition. For example, the carrier may bind to 100 or 1000 CD8+ T cells for every carrier that binds to other types of cells.

The diameter of the complex formed between T cells and carrier should preferably be at least 20% larger than the uncomplexed T cells and more preferably at least 50% larger, at least twice as large or at least ten times as large.

This increase in size may be either due to the binding of a single large carrier to the cells or due to the binding of several smaller carriers. Binding may involve using: a) only carriers with a diameter at least as large (or in other embodiments, at least twice as large or at least ten times as large) as that of the T cells; b) only carriers with a diameter no more than 50% (or in other embodiments, no more than 25% or 15%) as large as that of the T cells; or c) mixtures of large and small carriers with these size characteristics (e.g., there may be one group of carriers with a diameter at least as large (or at least twice or ten times as large) as the T cells and a second group of carriers with a diameter no more than 50% (or no more than 25% or 15%) as large as that of the T cells. Typically, a carrier will have a diameter of 1-1000 μm (and often in the range of 5-600 or 5-400 μm). Ideally, the complexes will be separated from uncomplexed cells or contaminants by DLD on a microfluidic device having an array of obstacles with a critical size lower than the size of the complexes but higher than the size of uncomplexed non-target cells or contaminants.

The purification of T cells may involve a two step process. For example, DLD may be performed on T cells that are not bound to carriers using an array of obstacles with a critical size smaller than the T cells. A composition containing the separated T cells together with other cells or particles may then be recovered and bound to one or more carriers in a way that promotes DLD separation and in which T cells are bound with specificity. The complexes thereby formed may then be separated on an array of obstacles with a critical size smaller than the complexes but larger than uncomplexed cells. In principle, the DLD steps could be performed in either order, i.e., it might be performed on the complexes first or on the uncomplexed T cells first.

Preferably, no more than four hours (and more preferably no more than three, two or one hour(s)) should elapse from the time that the obtaining of T cells is completed (e.g., until apheresis or leukapheresis is completed) until the T cells are bound to a carrier. In addition, no more than five hours (and preferably no more than four, three or two hours) should elapse from the time that the obtaining of T cells is completed until the first time that T cells are transfected or transduced. Ideally, all steps in producing the CAR T cells are performed at the same facility where the crude fluid composition comprising T cells is obtained and all steps are completed in no more than four (and preferably no more than three) hours.

CAR T cells made in this way may be used in treating patients for leukemia, e.g., acute lymphoblastic leukemia using procedures well established in the art of clinical medicine and, in these cases, the CAR may recognize CD19 or CD20 as a tumor antigen. The method may also be used for solid tumors, in which case antigens recognized may include CD22; RORl; mesothelin; CD33/IL3Ra; c-Met; PSMA; Glycolipid F77; EGFRvIII; GD-2; NY-ESO-1; MAGE A3; and combinations thereof. With respect to autoimmune diseases, CAR T cells may be used to treat rheumatoid arthritis, lupus, multiple sclerosis, ankylosing spondylitis, type 1 diabetes or vasculitis.

In some embodiments, the target cells produced by the methods described above will be available for administration to a patient earlier than if the cells were generated using methods not including a DLD. These cells may be administered 1 or more days earlier, and preferably 2, 3, 4, 5 or more days earlier. The cells may be administered within 8-10 days from the time that obtaining of the crude fluid composition is completed.

Collection and Processing of Cells

The current invention is also directed to protocols for collecting and processing cells from a patient which are designed to process cells quickly, and which can generally be performed at sites where the cells are collected. The protocols may be used as a part of the methods for preparing target cells and CAR T cells described above. Aspects of some of these protocols are illustrated in FIGS. 13 and 14 and may be contrasted with the protocol shown in FIG. 12. In the particular procedures illustrated, a composition obtained by apheresis of whole blood is obtained and T cells in the composition are then selected. The term "selected" in this context means that the T cells are bound by agents that recognize the T cells with specificity (as defined above). DLD is then used to isolate the selected T cells and transfer these cells into a chosen fluid medium.

More generally, the invention concerns a method of collecting target cells by: a) obtaining a crude fluid composition comprising the target cells from a patient; and b) performing Deterministic Lateral Displacement (DLD) on the crude fluid composition to obtain a composition enriched in target cells wherein either before, or after DLD, the target cells are bound to a carrier in a way that promotes DLD separation. For example, a carrier may be used that has on its surface an affinity agent (e.g., an antibody, activator, hapten or aptamer) that binds with specificity (as defined above) to the target cells.

Carrier may, if desired, be bound to target cells during the time that the cells are being collected from the patient and no more than five hours (and preferably no more than four, three, two or one hour(s)) should elapse from the time that the obtaining of the crude fluid composition comprising target cells is completed until the target cells are bound to the carrier.

The diameter of the complex formed between target cells and one or more carriers should preferably be at least 20% larger than the uncomplexed cells and preferably at least 50% larger, at least twice as large or at least ten times as large. This increase in size may be either due to the binding of a single large carrier to the target cells or due to the binding of several smaller carriers. Binding may involve using: i) only carriers with a diameter at least as large (or in other embodiments, at least twice as large or at least ten times as large) as that of the target cells; ii) only carriers with a diameter no more than 50% (or in other embodiments, no more than 25% or 15%) as large as that of the target cells; or iii) mixtures of large and small carriers with these size characteristics (e.g., there may be one group of carriers with a diameter at least as large (or at least twice or ten times as large) as the target cells and a second group of carriers with a diameter no more than 50% (or no more than 25% or 15%) as large as that of the target cells. Typically a carrier will have a diameter of 1-1000 μm (and often in the range of 5-600 or 5-400 μm). Ideally the complexes would be separated from other cells or contaminants by DLD on a microfluidic device having an array of obstacles with a critical size lower than the size of the complexes but higher than the size of uncomplexed cells or contaminants.

In a preferred embodiment, the crude fluid composition comprising target cells is obtained by performing apheresis or leukapheresis on blood from the patient. This composition may include one or more additives that act as anticoagulants or that prevent the activation of platelets. Examples of such additives include ticlopidine, inosine, protocatechuic acid, acetylsalicylic acid, and tirofiban alone or in combination.

The microfluidic devices must have at least one channel extending from a sample inlet to one or more fluid outlets, wherein the channel is bounded by a first wall and a second wall opposite from the first wall. There must also be an array of obstacles arranged in rows in the channel, with each subsequent row of obstacles being shifted laterally with respect to a previous row such that, when said crude fluid composition comprising target cells is applied to an inlet of the device and fluidically passed through the channel, target cells flow to one or more collection outlets where an enriched product is collected and contaminant cells, or particles that are in the crude fluid composition and that are of a different size than the target cells flow to one more waste outlets that are separate from the collection outlets.

In a particularly preferred embodiment, target cells are T cells selected from the group consisting of: Natural Killer T cells; Central Memory T cells; Helper T cells and Regulatory T cells, with Natural Killer T cells being the most preferred. In alternative preferred embodiments, the target cells are stem cells, B cells, macrophages, monocytes, dendritic cells, or progenitor cells.

In addition to steps a) and b), the method of the invention may include: c) genetically engineering cells by transducing them using a viral vector. Alternatively, the cells may be transfected electrically, chemically or by means of nanoparticles and/or expanded cells in number; and/or d) treating the same patient from which the target cells were obtained with the target cells collected. In addition, the collected cells may be cultured and/or cryopreserved. In cases where the target cells are T cells, culturing should generally be carried out in the presence of an activator, preferably an activator that is bound to a carrier. Among the factors that may be included in T cell cultures are IL-2 and IL-15.

In some embodiments, the target cells produced by the methods described above will be available for administration to a patient earlier than if the cells were generated using methods not including DLD. These cells may be administered 1 or more days earlier, and preferably 2, 3, 4, 5 or more days earlier. The cells may be administered within 8-10 days from the time that obtaining of the crude fluid composition is completed.

In addition to the methods discussed above, the invention includes the target cells produced by the methods and treatment methods in which the target cells are administered to a patient.

Altering the Characteristics of Leukocytes Using DLD

Reducing the level of platelets in leukocyte preparations has advantages both with respect to the making of CAR T cells and in preparing leukocytes for other therapeutic uses. In this regard, the present invention is based, in part, on the concept that DLD reduces the total number of platelets in apheresis samples more effectively than commonly used Ficoll separations (see FIGS. 19-21), especially when a buffer is used that does not promote platelet aggregation (see FIGS. 22-23). When used in combination with separation based on magnetic beads that specifically bind to T cells, DLD results in a preparation of cells that can be expanded more rapidly than when such magnetic beads are used either alone or in conjunction with Ficoll centrifugation (see FIG. 24). This effect may be partly due to a reduction in platelet number and partly due to factors that are independent of the number of platelets present (see FIG. 24). In addition, the results obtained using the DLD/magnetic bead procedure are more consistent (see FIG. 25) and the expanded T cells from this procedure have a higher percentage of T cells with a central memory phenotype when compared to populations prepared using a Ficoll/magnetic bead approach (see FIG. 26). The higher initial cell recovery from DLD combined with: a) a more rapid expansion of T cells and b) a higher percentage of central memory cells, means that therapeutically effective levels of T cells can be made available for patients more rapidly.

In one aspect, the invention is directed to a method for decreasing the ratio of platelets to leukocytes in an apheresis sample by performing deterministic lateral displacement on the sample in the absence of centrifugation or elutriation to obtain a product in which the ratio of platelets to leukocytes is at least 20% (and preferably 50% or 70%) lower than the ratio obtained when the same procedure is performed using centrifugation (including gradient centrifugation or counterflow centrifugation) or elutriation instead of DLD. Preferably, this procedure includes no separation steps performed on the apheresis sample prior to DLD and DLD is carried out in a buffer that does not comprise intercalators or other means that alter the size of platelets and that does not promote platelet aggregation. Agents that should be avoided include dextran and other highly charge polymers. In addition to lowering the ratio of platelets to leukocytes, the total number of platelets in the DLD derived product should be at least 70% lower than in the apheresis sample and preferably, at least 90% lower.

In another aspect, the invention is directed to a method for purifying T cells from an apheresis sample by performing DLD on the sample, followed by an affinity separation step and expansion of the T cells by culturing in the presence of activator. This process should result in a number of T cells that is at least twice as high as the number produced by the same procedure performed using Ficoll centrifugation instead of DLD. A preferred affinity method comprises the use of magnetic beads that bind specifically to T cells by an antibody that recognizes at least CD3, and might include CD3 together with CD28 or other costimulatory molecules. The number of T cells obtained after 14 days in culture should be at least two times higher (and preferably at least four or six time higher) than the number produced by the same procedure performed using Ficoll centrifugation instead of DLD. The percentage of memory T cells in the product produced by this method should be at least 10% (and preferably at least 20%) higher than the percentage produced using the same procedure but with Ficoll centrifugation instead of DLD.

The method is especially well suited to the production of T cells for CAR T cell therapy. The time needed to produce a sufficient number of cells to treat a patient is reduced by at least 5% (and preferably at least 10% or at least 20%) using DLD instead of Ficoll centrifugation and the CAR T cells can be prepared without the need for freezing. In a preferred method, cells are collected from a patient, processed by DLD and, optionally, an affinity method at the same site. Genetic transformation may also take place at the site and, preferably, no more than one hour elapses from the time that apheresis is completed until DLD is begun.

The invention also encompasses a method for decreasing the ratio of platelets to leukocytes in an apheresis sample by performing deterministic lateral displacement (DLD) on the sample. DLD is carried out in the absence of centrifugation or elutriation, to obtain a product in which the total number of platelets is at least 70% (and preferably at least 90%) lower than in the apheresis sample. DLD should preferably be carried out in a buffer that does not comprise intercalators and that does not promote platelet aggregation. Preferably, the buffer does not comprise dextran or other highly charge polymers.

The invention is not limited to leukocytes but also includes other therapeutically valuable cells, especially cells that may be present in apheresis preparations, including circulating stem cells. The benefits of DLD, including benefits due to the removal unwanted platelets, should apply to a wide variety of processes.

Methods of Using DLD for Large Volumes of Leukapheresis Material

One advantage of DLD is that it can be used to process small quantities of material with little increase in volume as well as relatively large quantities of material. The procedure may be used on leukapheresis products that have a small volume due to the concentration of leukocytes by centrifugation as well as in processing a large volume of material.

Thus, in another aspect, the invention is directed to a system for purifying cells from large volume leukapheresis processes in which at least one microfluidic device is used that separates materials by DLD. The objective is to obtain leukocytes that may be used therapeutically or that secrete agents that may be used therapeutically. Of particular importance, the invention includes binding specific types of leukocytes to one or more carriers in a way that promotes and, optionally, also complements DLD separation and then performing DLD on the complex. In this way, specific types of leukocytes may be separated from cells that are about the same size and that, in the absence of complex formation, could not be resolved by DLD. In this regard, a two step procedure as discussed above may sometimes be advantageous in which a one DLD procedure separates unbound leukocytes from smaller material and a another DLD procedure separates a carrier-leukocyte complex from uncomplexed cells. Essentially the same technique can be used in other contexts as well, e.g., on cultured cells, provided that cell specific carriers are available. In all instances, the cells may be recombinantly genetically engineered to alter the expression of one or more of their genes.

For leukapheresis material, the microfluidic devices must have at least one channel extending from a sample inlet to both a "collection outlet" for recovering white blood cells (WBCs) or specific leukocyte-carrier complexes and a "waste outlet" through which material of a different size (generally smaller) than WBCs or uncomplexed leukocytes flow. The channel is bounded by a first wall and a second wall opposite from the first wall and includes an array of obstacles arranged in rows, with each successive row being shifted laterally with respect to a previous row. The obstacles are disposed in a manner such that, when leukapheresis material is applied to an inlet of the device and fluidically passed through the channel, cells or cell complexes are deflected to the collection outlet (or outlets) where an enriched product is collected and material of a different (generally smaller) size flows to one or more separate waste outlets.

In order to facilitate the rapid processing of large volumes of starting material, the obstacles in microfluidic devices may be designed in the shape of diamonds or triangles and each device may have 6-40 channels. In addition, the microfluidic devices may be part of a system comprising 2-20 microfluidic devices (see FIG. 7). Individual devices may be operated at flow rates of 14 ml/hr but flow rates of at least 25 ml/hr (preferably at least 40, 60, 80 or 100 ml per hour) are preferable and allow large sample volumes (at least 200 ml and preferably 400-600 ml) to be processed within an hour.

Separation of Viable Cells

In another aspect, the invention is directed to methods of separating a viable cell from a nonviable cell comprising: (a) obtaining a sample comprising the viable cell and the nonviable cell, where the viable cell can have a first predetermined size and the nonviable cell can have a second predetermined size; and where the first predetermined size can be greater than or equal to a critical size, and the second predetermined size can be less than the critical size; (b) applying the sample to a device, where the device can comprise an array of obstacles arranged in rows, where the rows can be shifted laterally with respect to one another, where the rows can be configured to deflect a particle greater than or equal to the critical size in a first direction and a particle less than the critical size in a second direction; and (c) flowing the sample through the device, where the viable cell can be deflected by the obstacles in the first direction, and the non-viable cell can be deflected in the second direction, thereby separating the viable cell from the non-viable cell. The critical size can be about 1.1-fold greater than the second predetermined size and in some embodiments, the viable cell can be an actively dividing cell. In some embodiments, the device can comprise at least three zones with progressively smaller obstacles and gaps.

Separation of Adherent Cells

The invention also includes a method of obtaining adherent target cells, preferably cells of therapeutic value, e.g., adherent stem cells, by: a) obtaining a crude fluid composition comprising the adherent target cells from a patient; and b) performing Deterministic Lateral Displacement (DLD) to obtain a composition enriched in the adherent target cells. During this process, the adherent target cells may be bound to one or more carriers in a way that promotes or complements DLD separation. For example carriers may have on their surface an affinity agent (e.g., an antibody, activator, hapten or aptamer) that binds with specificity (as defined above) to the adherent target cells and may be transfected or transduced with nucleic acids designed to impart on the cells a desired phenotype, e.g., to express a chimeric molecule (preferably a protein that makes the cells of greater therapeutic value).

Carriers may be added at the time that the crude fluid composition is being collected or, alternatively after collection is completed but before DLD is performed for the first time. In a second alternative, DLD may be performed for a first time before carrier is added. For example, if the adherent cell has a size less than the critical size, the crude fluid composition may be applied to the device before the carrier is added, the adherent cell may be recovered, the cells may then be attached to one or more carriers to form a complex that is larger than the critical size of a device, a second DLD step may then be performed and the carrier adherent cell complexes may be collected.

Preferably, no more than three hours (and more preferably no more than two hours, or one hour) elapse from the time that the obtaining of the crude fluid composition from the patient is completed until the adherent cell is bound to a carrier for the first time. In another preferred embodiment, no more than four hours (and preferably no more than three or two hours) elapse from the time that the obtaining of the crude fluid composition from the patient is complete until the first time that the adherent cell or a carrier adherent cell complex is collected from the device for the first time.

The methodology described above may be used to separate adherent target cells, e.g., adherent stem cells, from a plurality of other cells. The method involves: a) contacting a crude fluid composition comprising the adherent target cells and the plurality of other cells, wherein the adherent target cells are at least partially associated with one or more carriers in a way that promotes DLD separation and form carrier associated adherent target cell complexes, wherein the complexes comprise an increased size relative to the plurality of other cells, and wherein the size of the carrier associated adherent cell complexes is preferably at least 50% greater than a critical size, and other, uncomplexed cells comprise a size less than the critical size; b) applying the crude fluid composition containing the carrier associated adherent cell complexes to a device, wherein the device comprises an array of obstacles arranged in rows, wherein the rows are shifted laterally with respect to one another, wherein the rows are configured to deflect cells or complexes greater than or equal to the critical size in a first direction and cells or complexes less than the critical size in a second direction; c) flowing the crude fluid composition comprising the carrier associated adherent target cell complexes through the device, wherein the complexes are deflected by the obstacles in the first direction, and uncomplexed cells are deflected in the second direction, thereby separating the carrier associated adherent cell complexes from the other uncomplexed cells; d) collecting a fluid composition comprising the separated carrier associated adherent target cell complexes.

The diameter of the complex formed between adherent target cells and one or more carriers should preferably be at least 20% larger than the uncomplexed cells and preferably at least 50% larger, at least twice as large or at least ten times as large. This increase in size may be either due to the binding of a single large carrier to the adherent target cells or due to the binding of several smaller carriers. Binding may involve using: a) only carriers with a diameter at least as large (or in other embodiments, at least twice as large or at least ten times as large) as that of the adherent target cells; b) only carriers with a diameter no more than 50% (or in other embodiments, no more than 25% or 15%) as large as that of the adherent target cells; or c) mixtures of large and small carriers with these size characteristics (e.g., there may be one group of carriers with a diameter at least as large (or at least twice or ten times as large) as the adherent target cells and a second group of carriers with a diameter no more than 50% (or no more than 25% or 15%) as large as that of the adherent target cells. Typically a carrier will have a diameter of 1-1000 μm (and often in the range of 5-600 or 5-400 μm).

The carriers may be made of any of the materials that are known in the art for the culturing of adherent cells including polypropylene, polystyrene, glass, gelatin, collagen, polysaccharides, plastic, acrylamide and alginate. They may be uncoated or coated with materials that promote adhesion and growth (e.g., serum, collagen, proteins or polymers) and may have agents (e.g., antibodies, antibody fragments, substrates, activators or other materials) attached to their surfaces. In some embodiments, the diluent can be growth media, the steps can be performed sequentially and, after step (d), buffer exchange can be performed.

Examples of specific adherent cells that may be isolated in the methods described above include: an MRC-5 cell; a HeLa cell; a Vero cell; an NIH 3T3 cell; an L929 cell; a Sf21 cell; a Sf9 cell; an A549 cell; an A9 cell; an AtT-20 cell; a BALB/3T3 cell; a BHK-21 cell; a BHL-100 cell; a BT cell; a Caco-2 cell; a Chang cell; a Clone 9 cell; a Clone M-3 cell; a COS-1 cell; a COS-3 cell; a COS-7 cell; a CRFK cell; a CV-1 cell; a D-17 cell; a Daudi cell; a GH1 cell; a GH3 cell; an HaK cell; an HCT-15 cell; an HL-60 cell; an HT-1080 cell; a HEK cell, HT-29 cell; an HUVEC cell; an I-10 cell; an IM-9 cell; a JEG-2 cell; a Jensen cell; a Jurkat cell; a K-562 cell; a KB cell; a KG-1 cell; an L2 cell; an LLC-WRC 256 cell; a McCoy cell; a MCF7 cell; a WI-38 cell; a WISH cell; an XC cell; a Y-1 cell; a CHO cell; a Raw 264.7 cell; a HEP G2 cell; a BAE-1 cell; an SH-SYS5 cell, and any derivative thereof.

Separation of Cells Bound to an Activator

The invention also includes methods of purifying cells capable of activation using the procedures described above. In a preferred embodiment, the invention is directed to a method of separating an activated cell from a plurality of other cells by: a) contacting a crude fluid composition comprising a cell capable of activation and the plurality of other cells with one or more carriers, in a way that promotes DLD separation, wherein one or more of the carriers comprise a cell activator, wherein one or more carriers are at least partially associated with the cell capable of activation by the cell activator upon or after contact to generate a carrier associated cell, wherein the association of the cell activator with the cell capable of activation at least partially activates the cell capable of activation, wherein the carrier associated cell complex comprises an increased size relative to other cells, and wherein a size of the carrier associated cell complex is greater than or equal to a critical size, and the cells in the plurality of other cells comprise a size less than the critical size; b) applying the crude fluid composition to a device, wherein the device comprises an array of obstacles arranged in rows; wherein the rows are shifted laterally with respect to one another, wherein the rows are configured to deflect a particle greater than or equal to the critical size in a first direction and a particle less than the critical size in a second direction; c) flowing the sample through the device, wherein the carrier associated cell complex is deflected by the obstacles in the first direction, and the cells in the plurality of other cells are deflected in the second direction, thereby separating the activated cell from the other cells of the plurality. The fluid composition comprising the separated carrier associated cell complex may then be collected. During this process the cells may optionally be transfected or transduced with nucleic acids designed to impart on the cells a desired phenotype, e.g., to express a chimeric molecule (preferably a protein that makes the cells of greater therapeutic value).

The cell capable of activation may be selected from the group consisting of: a T cell, a B cell, a macrophage, a dendritic cell, a granulocyte, an innate lymphoid cell, a megakaryocyte, a natural killer cell, a thrombocyte, a synoviocyte, a beta cell, a liver cell, a pancreatic cell; a DE3 lysogenized cell, a yeast cell, a plant cell, and a stem cell.

The cell activator may be selected from the group consisting of: an antibody or antibody fragment, CD3, CD28, an antigen, a helper T cell, a receptor, a cytokine, a glycoprotein, and any combination thereof. In other embodiments, the activator may be a small compound and may be selected from the group consisting of insulin, IPTG, lactose, allolactose, a lipid, a glycoside, a terpene, a steroid, an alkaloid, and any combination thereof.

In a preferred embodiment, the cell capable of activation is collected from a patient as part of a crude fluid composition comprising the cell capable of activation and a plurality of other cells, wherein no more than four hours (and preferably no more than three hours, two hours or one hour) elapse from the time that the obtaining of the crude fluid composition from the patient is completed until the cell capable of activation is bound to the carrier. It is also preferable that no more than four hours elapse from the time that the obtaining of the crude fluid composition from the patient is completed until step c) is completed. Alternatively, the method may be altered by binding activator before collection of cells begins.

Preferably, the diameter of the complex formed between a cell capable of activation and one or more carriers should be at least 20% larger than the uncomplexed cells and more preferably at least 50% larger, at least twice as large or at least ten times as large. This increase in size may be either due to the binding of a single large carrier to the cell capable of activation or due to the binding of several smaller carriers. Binding may involve using: a) only carriers with a diameter at least as large (or in other embodiments, at least twice as large or at least ten times as large) as that of the cell capable of activation; b) only carriers with a diameter no more than 50% (or in other embodiments, no more than 25% or 15%) as large as that of the cell capable of activation; or c) mixtures of large and small carriers with these size characteristics (e.g., there may be one group of carriers with a diameter at least as large (or at least twice or ten times as large) as the cell capable of activation and a second group of carriers with a diameter no more than 50% (or no more than 25% or 15%) as large as that of the cell capable of activation. Typically a carrier will have a diameter of 1-1000 μm (and often in the range of 5-600 or 5-400 μm).

Separating Compounds from Cells

In another embodiment, the invention includes methods of removing a compound from a cell comprising: (a) obtaining a fluid composition comprising the cell and the compound, where the cell has a predetermined size that is greater than a predetermined size of the compound, and where the predetermined size of the cell is greater than or equal to a critical size, and the predetermined size of the compound is less than the critical size; (b) applying the sample to a device, where the device comprises an array of obstacles arranged in rows, where the rows are shifted laterally with respect to one another, where the rows are configured to deflect a particle greater than or equal to the critical size in a first direction and a particle less than the critical size in a second direction; and (c) flowing the sample through the device, during which the cell is deflected by the obstacles in the first direction, and the compound can be deflected in the second direction, thereby removing the compound from the cell. In some embodiments, the method can further comprise culturing the cell after step (c) or recycling the cells to a culture from which the fluid composition of step a) was obtained.

The compound may be a toxic compound and may be selected from the group consisting of: an antibiotic, an antifungal, a toxic metabolite, sodium azide, a metal ion, an endotoxin, a plasticizer, a pesticide, and any combination thereof. In other embodiments, the compound can be a spent chemical component.

Continuous Purification of a Secreted Cellular Product

The invention also includes methods of continuously purifying a secreted product from a cell comprising: (a) obtaining a fluid composition comprising the cell (which may be a cell culture composition), where the cell is suspended in the fluid composition (or the cell is bound to one or more carriers in a way that promotes DLD separation and that forms a carrier-cell complex) and where the cell secretes the secreted product into the fluid composition, where the cell (or the carrier-cell complex) has a predetermined size that is greater than a predetermined size of the secreted product, and where the predetermined size of the cell (or the carrier-cell complex) is greater than or equal to a critical size, and the predetermined size of the secreted product is less than the critical size; (b) applying the fluid composition comprising the cell (or the carrier-cell complex) to a device for DLD, where the device comprises an array of obstacles arranged in rows; where the rows are shifted laterally with respect to one another, where the rows are configured to deflect a particle greater than or equal to the critical size in a first direction and a particle less than the critical size in a second direction; (c) flowing the fluid composition comprising the cell or the carrier-cell complex through the device, where the cell or carrier-cell complex is deflected by the obstacles in the first direction, and the secreted product is deflected in the second direction, thereby separating the secreted product from the cell; (d) collecting the secreted product, thereby producing a fluid composition of the secreted product that is purified; (e) collecting a recovered fluid composition comprising the separated cells or carrier-cell complexes; (f) re-applying the cells (or the carrier-cell complexes) to the fluid composition; and repeating steps (a) through (e); thereby continuously purifying the secreted product from the cell.

The secreted product can be a protein, an antibody, a biofuel, a polymer, a small molecule, and any combination thereof and the cell can be a bacterial cell, an algae cell, a mammalian cell, and a tumor cell. In one preferred embodiment, the secreted product is a therapeutically valuable protein, antibody, polymer or small molecule. In addition the fluid composition of step a) may be obtained from a culture in which cells are grown on carriers.

Use of Microfluidic Sizing Devices

More broadly, the invention is directed to methods of engineering a population of target cells prepared by any size based microfluidic separation method. Differences in sorting cells based on size may be the result of using bump arrays as discussed herein or result from inertial forces generated by controlling the flow rate during separations or through the design of the microfluidic devices themselves (see U.S. Pat. Nos. 9,895,694 and 9,610,582, incorporated herein by reference in their entirety). There may be only a single separation procedure used or there may be more than one. For example, target cells may be separated from smaller particles and cells using one microfluidic procedure and from larger particles and cells using a second procedure.

Once target cells are isolated, they are genetically engineered to have a desired phenotype. This may be accomplished using standard recombinant methodology for transfecting or transforming cells. For example, cells may be transfected with a vector to express a recombinant phenotype. By avoiding centrifugation prior to genetic engineering, there should be at least a 20% increase in cells with the desired characteristics.

Preferred target cells are leukocytes (especially T cells) or stem cells and the preferred crude fluid composition is blood or an apheresis preparation obtained from a patient. A central objective is to reduce the ratio of platelets to target cells in these preparations by at least 50% and preferably by at least 80% or 90%. The isolation of target cells should take place under conditions such that a product is obtained in which the total number of platelets is at least 70% (and preferably at least 90%) lower than in the starting apheresis preparation.

During or after genetic engineering, cells are expanded in cell culture. Using the procedures described above, the number of T cells obtained after 14 days in culture should be at least two times (and preferably at least five or ten times) higher than in a procedure in which cells are isolated using centrifugation. In addition, the percentage of memory T cells in culture relative to the total number of T cells should be at least 10% (and preferably 20% or 30%) higher than in a procedure in which T cells are isolated by centrifugation.

No more than one hour should elapse from the time that apheresis collection is completed until the time that DLD is performed and no more than four hours should elapse from the time the obtaining of the apheresis sample is completed until the target cells have been isolated and are genetically engineered.

In a particularly preferred embodiment, the method described above is used for the production of CAR T cells. This involves first obtaining a crude fluid composition containing T cells by apheresis and then isolating the cells on a microfluidic device using one or more procedures that separate T cells from platelets based on differences in size. As a result, a product should be obtained that is an enriched in T cells and depleted in platelets. In the next step, the isolated T cells are genetically engineered to express chimeric antigen receptors (CARs) on their surface. These cells are cultured to expand their number and then collected. The T cells should not be centrifuged or elutriated at any step prior to being genetically engineered and, in a preferred embodiment, reagents used for genetic engineering are separated from cells by size using a microfluidic device. In an additional preferred embodiment, T cells are collected by being transferred into a pharmaceutical composition for administration to a patient.

T cells should not be frozen before being collected or transferred into a pharmaceutical composition and preferably at least 90% of platelets are removed. Prior to, or during, culturing, cells may be exposed to a T cell activator or a carrier. This may help to stabilize the cells and may also facilitate size-based microfluidic separation. It should be noted however, that neither activators nor the carriers necessarily need to be bound to magnetic beads or particles.

Compared to a procedure in which cells are isolated or concentrated by centrifugation, CAR T cells obtained by microfluidic separation should be available for use by a patient at least one day (and preferably, at least 3, 5 or 10 days) earlier. Overall, the time necessary to produce a sufficient number of CAR T cells for treatment should be at least 10% (and preferably at least 20% or 30%) shorter than when the same method is carried out using Ficoll centrifugation to isolate cells. This is partly because, by using a size based microfluidic separation, the number of CAR T cells obtained after 14 days in culture will typically be at least two times (and preferably four or eight times) higher than the number in cultures which use cells obtained by Ficoll centrifugation. In addition, when cells prepared by the present method are administered to a patient, they should exhibit at least 10% less senescence than cells isolated from an apheresis composition by centrifugation.

The present invention also encompasses treating a patient for a disease or condition by administering a therapeutically effective amount of cells prepared by the methods discussed above. This includes any disease or condition that responds to engineered leukocytes or stem cells and, at least in the case of CAR T cells, cancer is among the diseases that may be treated.

BRIEF DESCRIPTION OF THE DRAWINGS

FIGS. 1A-1G: FIGS. 1A-1C illustrate different operating modes of DLD. This includes: i) Separation (FIG. 1A), ii) Buffer Exchange (FIG. 1B) and iii) Concentration (FIG. 1C). In each mode, essentially all particles above a critical diameter are deflected in the direction of the array from the point of entry, resulting in size selection, buffer exchange or concentration as a function of the geometry of the device. In all cases, particles below the critical diameter pass directly through the device under laminar flow conditions and subsequently off the device. FIG. 1D shows a 14 lane DLD design used in separation mode. The full length of the depicted array and microchannel is 75 mm and the width is 40 mm, each individual lane is 1.8 mm across. FIGS. 1E-1F are enlarged views of the plastic diamond post array and consolidating collection ports for the exits. FIG. 1G depicts a photo of a leukapheresis product being processed using a prototype device at 10 PSI.

FIGS. 2A-2H: FIG. 2A is a scatter plot showing the range of normal donor platelet and WBC cell counts used in this study. Mean counts of WBC: $162.4 \times 10^6$/mL and Platelets: $2718 \times 10^3/\mu L$ respectively (+). The outlier sample (▲), clogged the 20 μm prefilter and was excluded from the data set. Input sample shown (FIGS. 2C and 2D). Representative 24-hour old normal donor leukapheresis input (FIG. 2B) and PBMC product processed by either a 14-lane diamond post DLD at 10 PSI (FIG. 2E) or Ficoll-Hypaque (FIG. 2F). Representative DLD product (FIG. 2G) and Ficoll (FIG. 2H) from the same Leukapheresis donor (#37). Input (FIGS. 2B, 2C, 2D) and product fractions (FIGS. 2E and 2F) were fixed and stained on slides with CD41-FITC (platelets) plus CD45-Alexa647 (WBC) and counter-stained with DAPI (nuclear DNA).

FIG. 4 is a graph depicting rapid gain of memory cell phenotype and consistent activation of samples via DLD compared to Ficoll & Direct Magnet. Plot of % CD45RA−, CD25+ cells measuring conversion to T cell activation and conversion via CD45 RO status is shown. Cells were fed 200 Units IL-2/mL culture at Day 3 and again at day 8 only as the experiment was designed to address initial ability to expand.

FIG. 5B shows the percentage of T central memory cells (day 15) and FIG. 5C shows the number of T central memory cells (day 15).

FIGS. 6A-6B concern cytometric analysis of T central memory cells and the number of central memory cells produced. FIG. 6A: T Central Memory Cells: CD3+ T cells were gated on a singlet gate followed by a CD3 v Side scatter and central memory phenotyping using 4 parameter gate of CD45RO, CCR7, CD28 and CD95 to define the central memory population. The population was back gated to display central memory cells, which in a color figure are red, as fraction of T cells. Non-red cells in a color figure represent all non central memory T cells. FIG. 6B: Phenotype Conversion and Key Metrics (Day 15): Key metrics show # of donors where the number of central memory cells is >50%, with the average and % CV associated with the central memory expansion.

FIG. 7 is a schematic showing how current individual chips have been designed to be stackable in layers to achieve throughput as demanded by any particular application using established manufacturing approaches. Injection molded layers are planned as systems are developed.

FIG. 8A: DLD Product Derived from Whole Blood: Whole blood was passed over first DLD to remove erythrocytes. A second, in line, concentrating DLD, designed to achieve a concentration factor of 12, was connected to the product output of the separating DLD. Equal volumes of product and waste were added to tubes with equal numbers of absolute count beads and analyzed by flow cytometry. The resulting relative cell:bead ratio for Waste (FIG. 8B) and for Concentrate (FIG. 8C) was calculated compared to the input material to determine fold concentration. Leukocytes were stained with CD45 PerCP and 1 mM DRAQ5, which was used as a fluorescence threshold to acquire both the beads and the leukocytes. 5000 bead events acquired. (all reagents eBioscience). Designed Concentration Factor: 12.0×; Observed relative concentration: 15.714/1.302=12.07×

FIG. 9 is a supplemental figure on the expression of CD25 and CD4 on unstimulated CD3+ T Cells purified by either DLD or Ficoll methods (Day 8). Cells were prepared as described and analyzed as in FIG. 3. Mean CD4+25+: Ficoll: 20.25%; DLD: 8%.

FIG. 11 is a supplemental figure depicting estimates of the number of central memory T cells, post expansion with IL-2, assuming yields in this study and a typical leukapheresis harvest from a donor with $50 \times 10^6$ WBC cells per/mL and containing 50% CD3 lymphocytes in 250 mL.

FIG. 12 illustrates a protocol that might, in principle, be used for producing CAR T cells and administering the cells to a patient. It has been included to contrast other procedures discussed herein and does not represent work actually performed.

FIG. 13 illustrates a proposed protocol for producing CAR T cells that differs from the protocol of FIG. 12 in the initial steps of the procedure. The steps in the center portion of the figure are included for purposes of comparison. The diagram is intended to illustrate inventive concepts and does not represent work actually performed.

FIG. 14 illustrates a second proposed protocol for producing CAR T cells that differs from the protocol of FIG. 12 in the initial steps of the procedure. The steps in the center portion of the figure are included for purposes of comparison. As with FIGS. 12 and 13, the diagram is intended to illustrate inventive concepts and does not represent work actually performed.

FIG. 15 shows a schematic of a device for removing secreted products from spent cells.

FIG. 16 shows a schematic of a device for continuous removal of toxic compounds from actively growing cells.

FIG. 17 shows a schematic of a device for continuous removal of toxic compounds from actively growing cells with the option of adding carriers between each iteration.

FIG. 18A shows an example of a mirrored array of obstacles with a downshift. A central channel is between an array of obstacles on the left and on the right. The central channel can be a collection channel for particles of at least a critical size (i.e., particles of at least a critical size can be deflected by the arrays to the central channels, whereas particles of less than the critical size can pass through the channel with the bulk flow). By downshifting rows, changes in the width of the channel relative to a mirrored array with a downshift can be achieved. The amount of downshift can vary based on the size and/or cross-sectional shape of the obstacles. FIG. 18B illustrates a mirrored array of obstacles with no downshift. An array on the left and an array on the right can deflect particles of at least a critical size to the central channel.

FIG. 20 graphically shows the percentage of platelets left in apheresis samples processed by Ficoll centrifugation (white bars) and apheresis samples processed by DLD (striped bars) using three different buffers. The X axis is the percentage of platelets remaining. Results for a 1% BSA/PBS buffer are shown on the far left side of the figure; percentages for a buffer containing an F127 poloxamer intercalator are in the center and percentages for an elutriation buffer are on the far right.

FIG. 21 shows the results of FIG. 22 except that the Y axis represents the number of platelets per leukocyte, i.e., the ratio of platelets to leukocytes. Bars with triplet stripes represent the ratio present in the initial apheresis sample, white bars are the ratio after processing by Ficoll centrifugation and bars with widely spaced single stripes are the ratio after processing by DLD.

FIG. 22 is a bar graph showing the expansion of T cells that occurs as the result of processing apheresis samples by Ficoll centrifugation (solid white bars) and DLD (bars with single stripes adjacent to white bars). Moving from left to right the bars show the effect of adding 10% (bars with double stripes), 50% (stippled bars) and 100% (bars with dark widely spaced bars adjacent to stippled bars) of the platelets originally present in the apheresis starting material back to the cells processed by DLD before expansion. The left side of the figure depicts cells processed via DLD without EDTA and then stimulated with CD3/CD28 at day 0, with CD3 positive cells counted on day 3, 7 and 14. The right side of the figure shows cells processed with 2 mM EDTA and then stimulated with CD3/CD28 at day 0, with CD3 positive cells counted on day 3, 7 and 14.

FIG. 23 is a comparison of variability in the expansion of T cells obtained using three methods of processing: separation using magnetic beads alone (bar on the far left of the figure), separation using Ficoll centrifugation followed by magnetic beads (center bar), and separation by DLD followed by magnetic beads (bar on the far right).

FIG. 24 shows the percentage of cells present in the expanded T cell populations of FIG. 23 that are central memory T cells.

Overview of Workflow Figures: " FIG. 25 shows the workflow that might be expected for a typical process used, for example, in making CAR T cells. Transformation of the cells would typically occur at the manufacturing site after cryopreserved samples are thawed, washed, debulked and enriched. FIG. 26 shows several places (stippled boxes) in a prototype CAR T cell process where DLD might be used while maintaining the same basic workflow. FIGS. 27-32 then present a number of illustrative examples of how DLD may be used to modify workflow and improve the prototype process. Primary objectives are to produce cells of better overall quality, shorten the time needed to obtain a sufficient number of cells to treat a patient and to automate steps that are currently more labor intensive.

FIG. 25: FIG. 25 illustrates the basic workflow generally involved in current methods for processing cells from a patient for therapeutic use. As illustrated, the process starts at a clinic with the collection of cells ("apheresis collection"), proceeds to a manufacturing site where the cells are expanded and may be engineered, and ends back at the clinic with the administration of the cells to a patient ("Re-infusion").

FIG. 26: FIG. 26 shows several steps in the CAR T workflow where DLD could be used (stippled boxes). In this example, the basic workflow remains essentially unchanged.

FIG. 27: FIG. 27 illustrates that DLD may be used immediately after apheresis to clean up cells prior to freezing (stippled box). The advantages of using DLD at this point are that it removes platelets from cells before shipment and thereby eliminates deleterious effects from platelet activation, clot formation, any storage related degranulation and overall loss of cells. In this manner, DLD improves the quality of cell compositions being shipped and replaces one of the hands on labor steps in the process with an automated counterpart.

FIG. 28: In this scenario, DLD is used during early steps in which cells are cleaned up, activated, DLD separated and transfer into a desired medium, e.g., a growth medium (stippled boxes). Importantly, freezing and cryopreservation at the clinic and subsequent thawing at the manufacturing site are avoided which should reduce the time needed to complete the process, e.g., by about 2-3 days. Although not preferred, a cryopreservation step could, if desired, still be performed. Other steps that might be avoided are indicated by crossed through text.

FIG. 29: In this scenario, DLD is used in conjunction with magnetic beads that bind to cell surface CD3 on T cells. This scenario has the same advantage of reducing platelets described above but may be used to activate cells and begin growth much sooner than in the prototype procedure. Cells may also be shipped at warm temperatures compatible with growth. As a result, counterpart steps that would have been performed at the manufacturing site are eliminated and overall processing time is correspondingly reduced.

FIG. 30: The most important difference in the scenario shown in FIG. 30 compared to the scenario in FIG. 29 is that cells are genetically transformed with virus immediately after exposure to activator (see stippled boxes). Rather than several days elapsing before activation and transformation, cells are purified, activated, transformed and growing in culture medium within 24 hours after apheresis collection is completed. Preferably the time from the completion of apheresis until exposure to vector should be no more than 12 hours, and more preferably, no more than six or three hours. Most preferably, exposure would occur within two hours after apheresis is complete and, in all cases, before cells are frozen. The figure shows many processing steps at the manufacturing site that may be eliminated and it is expected that the time needed to obtain sufficient cells for treating a patient would be reduced by at least 3 or 4 days.

FIG. 31: The scenario shown in FIG. 31 is similar to that in FIG. 30 except that separation by an affinity procedure (exemplified by magnetic beads that recognize CD3 containing cells) is added in the early steps to help in the isolation of T cells. DLD is also used to purify and/or concentrate cells.

FIG. 32: In the scenario shown in FIG. 32, T cells collected by apheresis are purified, engineered, expanded and concentrated for reinfusion without ever undergoing a step in which they are frozen. All steps can, if desired, be performed at the site where cells are collected without a need for shipping.

DEFINITIONS

Figure 3:
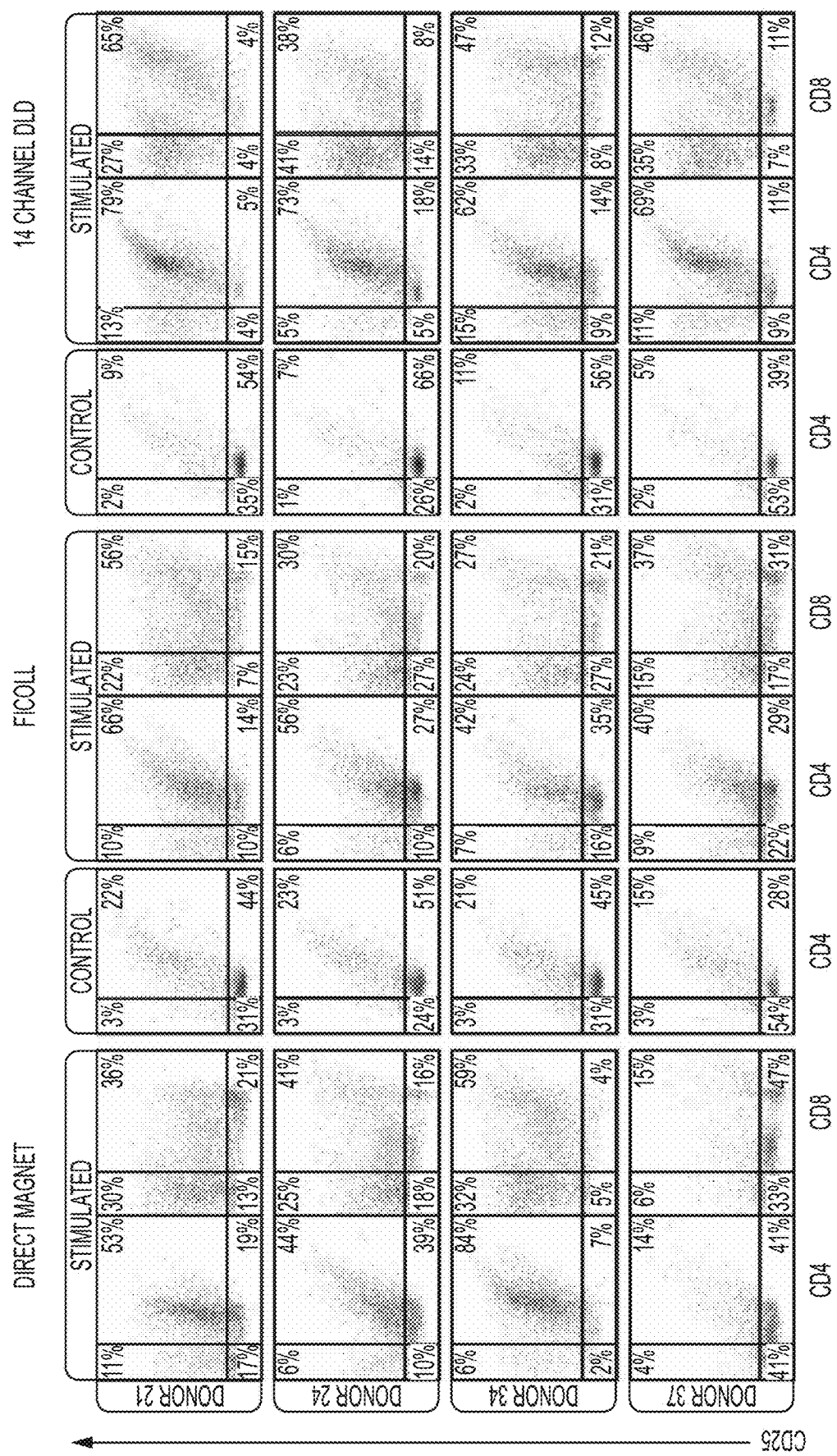
FIG. 3: This figure concerns the consistency of cell activation in DLD vs. Ficoll and Direct Magnet approaches (CD4, CD8 vs CD25 Day 8). Cell activation and Phenotypic profile shows a shift during expansion towards classic central memory T cell associated phenotype (Day 8). Cells were counted and de-beaded as described previously. At each time point ~100,000 cells were stained with CD3-BV421, CD45RA-BV605, CD95-FITC, CD279-PE, CD25-APC, CD4-Alexa 700, and CD8-APC-Cy7, incubated for 30 at room temperature in the dark and washed with 10 volumes of PBS prior to centrifugation and fixation in 1.0% Paraformaldehyde in PBS. Samples were acquired on a BD FACSAria, and analyzed using a CD3 and forward and side scatter gate using FlowLogic software.

Apheresis: As used herein this term refers to a procedure in which blood from a patient or donor is separated into its components, e.g., plasma, white blood cells and red blood cells. More specific terms are "plateletpheresis" (referring to the separation of platelets) and "leukapheresis" (referring to the separation of leukocytes). In this context, the term "separation" refers to the obtaining of a product that is enriched in a particular component compared to whole blood and does not mean that absolute purity has been attained.

CAR T cells: The term "CAR" is an acronym for "chimeric antigen receptor." A "CAR T cell" is therefore a T cell that has been genetically engineered to express a chimeric receptor.

CAR T cell therapy: This term refers to any procedure in which a disease is treated with CAR T cells. Diseases that may be treated include hematological and solid tumor cancers, autoimmune diseases and infectious diseases.

Carrier: As used herein, the term "carrier" refers an agent, e.g., a bead, or particle, made of either biological or synthetic material that is added to a preparation for the purpose of binding directly or indirectly (i.e., through one or more intermediate cells, particles or compounds) to some or all of the compounds or cells present. Carriers may be made from a variety of different materials, including DEAE-dextran, glass, polystyrene plastic, acrylamide, collagen, and alginate and will typically have a size of 1-1000 µm. They may be coated or uncoated and have surfaces that are modified to include affinity agents (e.g., antibodies, activators, haptens, aptamers, particles or other compounds) that recognize antigens or other molecules on the surface of cells. The carriers may also be magnetized and this may provide an additional means of purification to complement DLD and they may comprise particles (e.g., Janus or Strawberry-like particles) that confer upon cells or cell complexes non-size related secondary properties. For example the particles may result in chemical, electrochemical, or magnetic properties that can be used in downstream processes, such as magnetic separation, electroporation, gene transfer, and/or specific analytical chemistry processes. Particles may also cause metabolic changes in cells, activate cells or promote cell division.

Carriers that bind "in a way that promotes DLD separation": This term, refers to carriers and methods of binding carriers that affect the way that, depending on context, a cell, protein or particle behaves during DLD. Specifically, "binding in a way that promotes DLD separation" means that: a) the binding must exhibit specificity for a particular target cell type, protein or particle; and b) must result in a complex that provides for an increase in size of the complex relative to the unbound cell, protein or particle. In the case of binding to a target cell, there must be an increase of at least 2 µm (and alternatively at least 20, 50, 100, 200, 500 or 1000% when expressed as a percentage). In cases where therapeutic or other uses require that target cells, proteins or other particles be released from complexes to fulfill their intended use, then the term "in a way that promotes DLD separation" also requires that the complexes permit such release, for example by chemical or enzymatic cleavage, chemical dissolution, digestion, due to competition with other binders, or by physical shearing (e.g., using a pipette to create shear stress) and the freed target cells, proteins or other particles must maintain activity; e.g., therapeutic cells after release from a complex must still maintain the biological activities that make them therapeutically useful.

Carriers may also bind "in a way that complements DLD separation": This term refers to carriers and methods of binding carriers that change the chemical, electrochemical, or magnetic properties of cells or cell complexes or that change one or more biological activities of cells, regardless of whether they increase size sufficiently to promote DLD separation. Carriers that complement DLD separation also do not necessarily bind with specificity to target cells, i.e., they may have to be combined with some other agent that makes them specific or they may simply be added to a cell preparation and be allowed to bind non-specifically. The terms "in a way that complements DLD separation" and "in a way that promotes DLD separation" are not exclusive of one another. Binding may both complement DLD separation and also promote DLD separation. For example a polysaccharide carrier may have an activator on its surface that increases the rate of cell growth and the binding of one or more of these carriers may also promote DLD separation. Alternatively binding may just promote DLD separation or just complement DLD separation.

Target cells: As used herein "target cells" are the cells that various procedures described herein require or are designed to purify, collect, engineer etc. What the specific cells are will depend on the context in which the term is used. For example, if the objective of a procedure is to isolate a particular kind of stem cell, that cell would be the target cell of the procedure.

Isolate, purify: Unless otherwise indicated, these terms, as used herein, are synonymous and refer to the enrichment of a desired product relative to unwanted material. The terms do not necessarily mean that the product is completely isolated or completely pure. For example, if a starting sample had a target cell that constituted 2% of the cells in a sample, and a procedure was performed that resulted in a composition in which the target cell was 60% of the cells present, the procedure would have succeeded in isolating or purifying the target cell.

Bump Array: The terms "bump array" and "obstacle array" are used synonymously herein and describe an ordered array of obstacles that are disposed in a flow channel through which a cell or particle-bearing fluid can be passed.

Deterministic Lateral Displacement: As used herein, the term "Deterministic Lateral Displacement" or "DLD" refers to a process in which particles are deflected on a path through an array, deterministically, based on their size in relation to some of the array parameters. This process can be used to separate cells, which is generally the context in which it is discussed herein. However, it is important to recognize that DLD can also be used to concentrate cells and for buffer exchange. Processes are generally described herein in terms of continuous flow (DC conditions; i.e., bulk fluid flow in only a single direction). However, DLD can also work under oscillatory flow (AC conditions; i.e., bulk fluid flow alternating between two directions).

Critical size: The "critical size" or "predetermined size" of particles passing through an obstacle array describes the size limit of particles that are able to follow the laminar flow of fluid. Particles larger than the critical size can be 'bumped' from the flow path of the fluid while particles having sizes lower than the critical size (or predetermined size) will not necessarily be so displaced. When a profile of fluid flow through a gap is symmetrical about the plane that bisects the gap in the direction of bulk fluid flow, the critical size can be identical for both sides of the gap; however when the profile is asymmetrical, the critical sizes of the two sides of the gap can differ.

Fluid flow: The terms "fluid flow" and "bulk fluid flow" as used herein in connection with DLD refer to the macroscopic movement of fluid in a general direction across an obstacle array. These terms do not take into account the temporary displacements of fluid streams for fluid to move around an obstacle in order for the fluid to continue to move in the general direction.

Tilt angle ε: In a bump array device, the tilt angle is the angle between the direction of bulk fluid flow and the direction defined by alignment of rows of sequential (in the direction of bulk fluid flow) obstacles in the array.

Array Direction: In a bump array device, the "array direction" is a direction defined by the alignment of rows of sequential obstacles in the array. A particle is "bumped" in a bump array if, upon passing through a gap and encountering a downstream obstacle, the particle's overall trajectory follows the array direction of the bump array (i.e., travels at the tilt angle relative to bulk fluid flow). A particle is not bumped if its overall trajectory follows the direction of bulk fluid flow under those circumstances.

DETAILED DESCRIPTION OF THE INVENTION

The present invention is primarily concerned with the use of DLD in preparing cells that are of therapeutic value. The text below provides guidance regarding methods disclosed herein and information that may aid in the making and use of devices involved in carrying out those methods.

I. Designing Microfluidic Plates

Cells, particularly cells in compositions prepared by apheresis or leukapheresis, may be isolated by performing DLD using microfluidic devices that contain a channel through which fluid flows from an inlet at one end of the device to outlets at the opposite end. Basic principles of size based microfluidic separations and the design of obstacle arrays for separating cells have been provided elsewhere (see, US 2014/0342375; US 2016/0139012; 7,318,902 and U.S. Pat. No. 7,150,812, which are hereby incorporated herein in their entirety) and are also summarized in the sections below.

During DLD, a fluid sample containing cells is introduced into a device at an inlet and is carried along with fluid flowing through the device to outlets. As cells in the sample traverse the device, they encounter posts or other obstacles that have been positioned in rows and that form gaps or pores through which the cells must pass. Each successive row of obstacles is displaced relative to the preceding row so as to form an array direction that differs from the direction of fluid flow in the flow channel. The "tilt angle" defined by these two directions, together with the width of gaps between obstacles, the shape of obstacles, and the orientation of obstacles forming gaps are primary factors in determining a "critical size" for an array. Cells having a size greater than the critical size travel in the array direction, rather than in the direction of bulk fluid flow and particles having a size less than the critical size travel in the direction of bulk fluid flow. In devices used for leukapheresis-derived compositions, array characteristics may be chosen that result in white blood cells being diverted in the array direction whereas red blood cells and platelets continue in the direction of bulk fluid flow. In order to separate a chosen type of leukocyte from others having a similar size, a carrier may then be used that binds to that cell with in a way that promotes DLD separation and which thereby results in a complex that is larger than uncomplexed leukocytes. It may then be possible to carry out a separation on a device having a critical size smaller than the complexes but bigger than the uncomplexed cells.

The obstacles used in devices may take the shape of columns or be triangular, square, rectangular, diamond shaped, trapezoidal, hexagonal or teardrop shaped. In addition, adjacent obstacles may have a geometry such that the portions of the obstacles defining the gap are either symmetrical or asymmetrical about the axis of the gap that extends in the direction of bulk fluid flow.

II. Making and Operating Microfluidic Devices

General procedures for making and using microfluidic devices that are capable of separating cells on the basis of size are well known in the art. Such devices include those described in U.S. Pat. Nos. 5,837,115; 7,150,812; 6,685,841; 7,318,902; 7,472,794; and 7,735,652; all of which are hereby incorporated by reference in their entirety. Other references that provide guidance that may be helpful in the making and use of devices for the present invention include: U.S. Pat. Nos. 5,427,663; 7,276,170; 6,913,697; 7,988,840; 8,021,614; 8,282,799; 8,304,230; 8,579,117; US 2006/0134599; US 2007/0160503; US 20050282293; US 2006/0121624; US 2005/0266433; US 2007/0026381; US 2007/0026414; US 2007/0026417; US 2007/0026415; US 2007/0026413; US 2007/0099207; US 2007/0196820; US 2007/0059680; US 2007/0059718; US 2007/005916; US 2007/0059774; US 2007/0059781; US 2007/0059719; US 2006/0223178; US 2008/0124721; US 2008/0090239; US 2008/0113358; and WO2012094642 all of which are also incorporated by reference herein in their entirety. Of the various references describing the making and use of devices, U.S. Pat. No. 7,150,812 provides particularly good guidance and 7,735,652 is of particular interest with respect to microfluidic devices for separations performed on samples with cells found in blood (in this regard, see also US 2007/0160503).

A device can be made using any of the materials from which micro- and nano-scale fluid handling devices are typically fabricated, including silicon, glasses, plastics, and hybrid materials. A diverse range of thermoplastic materials suitable for microfluidic fabrication is available, offering a wide selection of mechanical and chemical properties that can be leveraged and further tailored for specific applications.

Techniques for making devices include Replica molding, Softlithography with PDMS, Thermoset polyester, Embossing, Injection Molding, Laser Ablation and combinations thereof. Further details can be found in "Disposable microfluidic devices: fabrication, function and application" by Fiorini, et al. (*BioTechniques* 38:429-446 (March 2005)), which is hereby incorporated by reference herein in its entirety. The book "Lab on a Chip Technology" edited by Keith E. Herold and Avraham Rasooly, Caister Academic Press Norfolk UK (2009) is another resource for methods of fabrication, and is hereby incorporated by reference herein in its entirety.

High-throughput embossing methods such as reel-to-reel processing of thermoplastics is an attractive method for industrial microfluidic chip production. The use of single chip hot embossing can be a cost-effective technique for realizing high-quality microfluidic devices during the prototyping stage. Methods for the replication of microscale features in two thermoplastics, polymethylmethacrylate (PMMA) and/or polycarbonate (PC), are described in "Microfluidic device fabrication by thermoplastic hot-embossing" by Yang, et al. (*Methods Mol. Biol.* 949: 115-23 (2013)), which is hereby incorporated by reference herein in its entirety The flow channel can be constructed using two or more pieces which, when assembled, form a closed cavity (preferably one having orifices for adding or withdrawing fluids) having the obstacles disposed within it. The obstacles can be fabricated on one or more pieces that are assembled to form the flow channel, or they can be fabricated in the form of an insert that is sandwiched between two or more pieces that define the boundaries of the flow channel.

The obstacles may be solid bodies that extend across the flow channel, in some cases from one face of the flow channel to an opposite face of the flow channel. Where an obstacle is integral with (or an extension of) one of the faces of the flow channel at one end of the obstacle, the other end of the obstacle can be sealed to or pressed against the opposite face of the flow channel. A small space (preferably too small to accommodate any particles of interest for an intended use) is tolerable between one end of an obstacle and a face of the flow channel, provided the space does not adversely affect the structural stability of the obstacle or the relevant flow properties of the device.

The number of obstacles present should be sufficient to realize the particle-separating properties of the arrays. The obstacles can generally be organized into rows and columns (Note: Use of the term "rows and columns" does not mean or imply that the rows and columns are perpendicular to one another). Obstacles that are generally aligned in a direction transverse to fluid flow in the flow channel can be referred to as obstacles in a column. Obstacles adjacent to one another in a column may define a gap through which fluid flows.

Obstacles in adjacent columns can be offset from one another by a degree characterized by a tilt angle, designated ε (epsilon). Thus, for several columns adjacent to one another (i.e., several columns of obstacles that are passed consecutively by fluid flow in a single direction generally transverse to the columns), corresponding obstacles in the columns can be offset from one another such that the corresponding obstacles form a row of obstacles that extends at the angle ε relative to the direction of fluid flow past the columns. The tilt angle can be selected and the columns can be spaced apart from each other such that 1/ε (when expressed in radians) is an integer, and the columns of obstacles repeat periodically. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of E.

Surfaces can be coated to modify their properties and polymeric materials employed to fabricate devices, can be modified in many ways. In some cases, functional groups such as amines or carboxylic acids that are either in the native polymer or added by means of wet chemistry or plasma treatment are used to crosslink proteins or other molecules. DNA can be attached to COC and PMMA substrates using surface amine groups. Surfactants such as Pluronic® can be used to make surfaces hydrophilic and protein repellant by adding Pluronic® to PDMS formulations. In some cases, a layer of PMMA is spin coated on a device, e.g., microfluidic chip and PMMA is "doped" with hydroxypropyl cellulose to vary its contact angle.

To reduce non-specific adsorption of cells or compounds, e.g., released by lysed cells or found in biological samples, onto the channel walls, one or more walls may be chemically modified to be non-adherent or repulsive. The walls may be coated with a thin film coating (e.g., a monolayer) of commercial non-stick reagents, such as those used to form hydrogels. Additional examples of chemical species that may be used to modify the channel walls include oligoethylene glycols, fluorinated polymers, organosilanes, thiols, poly-ethylene glycol, hyaluronic acid, bovine serum albumin, poly-vinyl alcohol, mucin, poly-HEMA, methacrylated PEG, and agarose. Charged polymers may also be employed to repel oppositely charged species. The type of chemical species used for repulsion and the method of attachment to the channel walls can depend on the nature of the species being repelled and the nature of the walls and the species being attached. Such surface modification techniques are well known in the art. The walls may be functionalized before or after the device is assembled.

III. CAR T Cells

Methods for making and using CAR T cells are well known in the art. Procedures have been described in, for example, U.S. Pat. Nos. 9,629,877; 9,328,156; 8,906,682; US 2017/0224789; US 2017/0166866; US 2017/0137515; US 2016/0361360; US 2016/0081314; US 2015/0299317; and US 2015/0024482; each of which is incorporated by reference herein in its entirety.

IV. Separation Processes that Use DLD

The DLD devices described herein can be used to purify cells, cellular fragments, cell adducts, or nucleic acids. As discussed herein, these devices can also be used to separate a cell population of interest from a plurality of other cells. Separation and purification of blood components using devices can be found, for example, in US Publication No. US2016/0139012, the teaching of which is incorporated by reference herein in its entirety. A brief discussion of a few illustrative separations is provided below.

A. Viable Cells

In one embodiment devices are used in procedures designed to separate a viable cell from a nonviable cell. The term "viable cell" refers to a cell that is capable of growth, is actively dividing, is capable of reproduction, or the like. In instances where a viable cell has a size that is greater than a nonviable cell, DLD devices can be designed to comprise a critical size that is greater than a predetermined size of the nonviable cell and less than a predetermined size of the viable cell. The critical size may be as little as 1.1 fold greater than (or less than) the predetermined size of the nonviable cell but generally, larger degrees (or smaller) are preferred, e.g., about 1.2 fold-2 fold, and preferably 3-10 fold.

B. Adherent Cells

In another embodiment, DLD devices can be used to in procedures to separate adherent cells. The term "adherent cell" as used herein refers to a cell capable of adhering to a surface. Adherent cells include immortalized cells used in cell culturing and can be derived from mammalian hosts. In some instances, the adherent cell may be trypsinized prior to purification. Examples of adherent cells include MRC-5 cells; HeLa cells; Vero cells; NIH 3T3 cells; L929 cells; Sf21 cells; Sf9 cells; A549 cells; A9 cells; AtT-20 cells; BALB/3T3 cells; BHK-21 cells; BHL-100 cells; BT cells; Caco-2 cells; Chang cells; Clone 9 cells; Clone M-3 cells; COS-1 cells; COS-3 cells; COS-7 cells; CRFK cells; CV-1 cells; D-17 cells; Daudi cells; GH1 cells; GH3 cells; HaK cells; HCT-15 cells; HL-60 cells; HT-1080 cells; HT-29 cells; HUVEC cells; I-10 cells; IM-9 cells; JEG-2 cells; Jensen cells; Jurkat cells; K-562 cells; KB cells; KG-1 cells; L2 cells; LLC-WRC 256 cells; McCoy cells; MCF7 cells; WI-38 cells; WISH cells; XC cells; Y-1 cells; CHO cells; Raw 264.7; BHK-21 cells; HEK 293 cells to include 293A, 293T and the like; HEP G2 cells; BAE-1 cells; SH-SYS5 cells; and any derivative thereof to include engineered and recombinant strains.

In some embodiments, procedures may involve separating cells from a diluent such as growth media, which may provide for the efficient maintenance of a culture of the adherent cells. For example, a culture of adherent cells in a growth medium can be exchanged into a transfection media comprising transfection reagents, into a second growth medium designed to elicit change within the adherent cell such as differentiation of a stem cell, or into sequential wash buffers designed to remove compounds from the culture.

In a particularly preferred procedure, adherent cells are purified through association with one or more carriers that bind in a way that promotes DLD separation. The carriers may be of the type described herein and binding may stabilize and/or activate the cells. A carrier will typically be in the rage of 1-1000 μm but may sometimes also be outside of this range.

The association between a carrier and a cell should produce a complex of increased size relative to other material not associated with the carrier. Depending of the particular size of the cells and carriers and the number of cells and carriers present, a complex may be anywhere from a few percent larger than the uncomplexed cell to many times the size of the uncomplexed cell. In order to facilitate separations, an increase of at least 20% is desirable with higher percentages (50; 100; 1000 or more) being preferred.

C. Activated Cells

The DLD devices can also be used in procedures for separating an activated cell or a cell capable of activation, from a plurality of other cells. The cells undergoing activation may be grown on a large scale but, in a preferred embodiment, the cells are derived from a single patient and DLD is performed within at least few hours after collection. The terms "activated cell" or "cell capable of activation" refers to a cell that has been, or can be activated, respectively, through association, incubation, or contact with a cell activator. Examples of cells capable of activation can include cells that play a role in the immune or inflammatory response such as: T cells, B cells; regulatory T cells, macrophages, dendritic cells, granulocytes, innate lymphoid cells, megakaryocytes, natural killer cells, thrombocytes, synoviocytes, and the like; cells that play a role in metabolism, such as beta cells, liver cells, and pancreatic cells; and recombinant cells capable of inducible protein expression such as DE3 lysogenized *E. coli* cells, yeast cells, plant cells, etc.

Typically, one or more carriers will have the activator on their surface. Examples of cell activators include proteins, antibodies, cytokines, CD3, CD28, antigens against a specific protein, helper T cells, receptors, and glycoproteins; hormones such as insulin, glucagon and the like; IPTG, lactose, allolactose, lipids, glycosides, terpenes, steroids, and alkaloids. The activatable cell should be at least partially associated with carriers through interaction between the activatable cell and cell activator on the surface of the carriers. The complexes formed may be just few percent larger than the uncomplexed cell or many times the size of the uncomplexed cell. In order to facilitate separations, an increase of at least 20% is desirable with higher percentages (40, 50 100 1000 or more) being preferred.

D. Separating Cells from Toxic Material

DLD can also be used in purifications designed to remove compounds that may be toxic to a cell or to keep the cells free from contamination by a toxic compound. Examples include an antibiotic, a cryopreservative, an antifungal, a toxic metabolite, sodium azide, a metal ion, a metal ion chelator, an endotoxin, a plasticizer, a pesticide, and any combination thereof. The device can be used to remove toxic compounds from cells to ensure consistent production of material from the cells. In some instances, the cell can be a log phase cell. The term "log phase cell" refers to an actively dividing cell at a stage of growth characterized by exponential logarithmic growth. In log phase, a cell population can double at a constant rate such that plotting the natural logarithm of cell number against time produces a straight line.

The ability to separate toxic material may be important for a wide variety of cells including: bacterial strains such as BL21, Tuner, Origami, Origami B, Rosetta, C41, C43, DH5α, DH10β, or XL1Blue; yeast strains such as those of genera *Saccharomyces, Pichia, Kluyveromyces, Hansenula* and *Yarrowia*; algae; and mammalian cell cultures, including cultures of MRC-5 cells; HeLa cells; Vero cells; NIH 3T3 cells; L929 cells; Sf21 cells; Sf9 cells; A549 cells; A9 cells; AtT-20 cells; BALB/3T3 cells; BHK-21 cells; BHL-100 cells; BT cells; Caco-2 cells; Chang cells; Clone 9 cells; Clone M-3 cells; COS-1 cells; COS-3 cells; COS-7 cells; CRFK cells; CV-1 cells; D-17 cells; Daudi cells; GH1 cells; GH3 cells; HaK cells; HCT-15 cells; HL-60 cells; HT-1080 cells; HT-29 cells; HUVEC cells; I-10 cells; IM-9 cells; JEG-2 cells; Jensen cells; Jurkat cells; K-562 cells; KB cells; KG-1 cells; L2 cells; LLC-WRC 256 cells; McCoy cells; MCF7 cells; WI-38 cells; WISH cells; XC cells; Y-1 cells; CHO cells; Raw 264.7; BHK-21 cells; HEK 293 cells to include 293A, 293T and the like; HEP G2 cells; BAE-1 cells; SH-SYS5 cells; stem cells and any derivative thereof to include engineered and recombinant strains.

E. Purification of Material Secreted from Cells

The DLD devices may also be used in the purification of material secreted from a cell. Examples of such secreted materials includes proteins, peptides, enzymes, antibodies, fuel, biofuels such as those derived from algae, polymers, small molecules such as simple organic molecules, complex organic molecules, drugs and pro-drugs, carbohydrates and any combination thereof. Secreted products can include therapeutically useful proteins such as insulin, Imatinib, T cells, T cell receptors, Fc fusion proteins, anticoagulants, blood factors, bone morphogenetic proteins, engineered protein scaffolds, enzymes, growth factors, hormones, interferons, interleukins, and thrombolytics.

Figure 15:
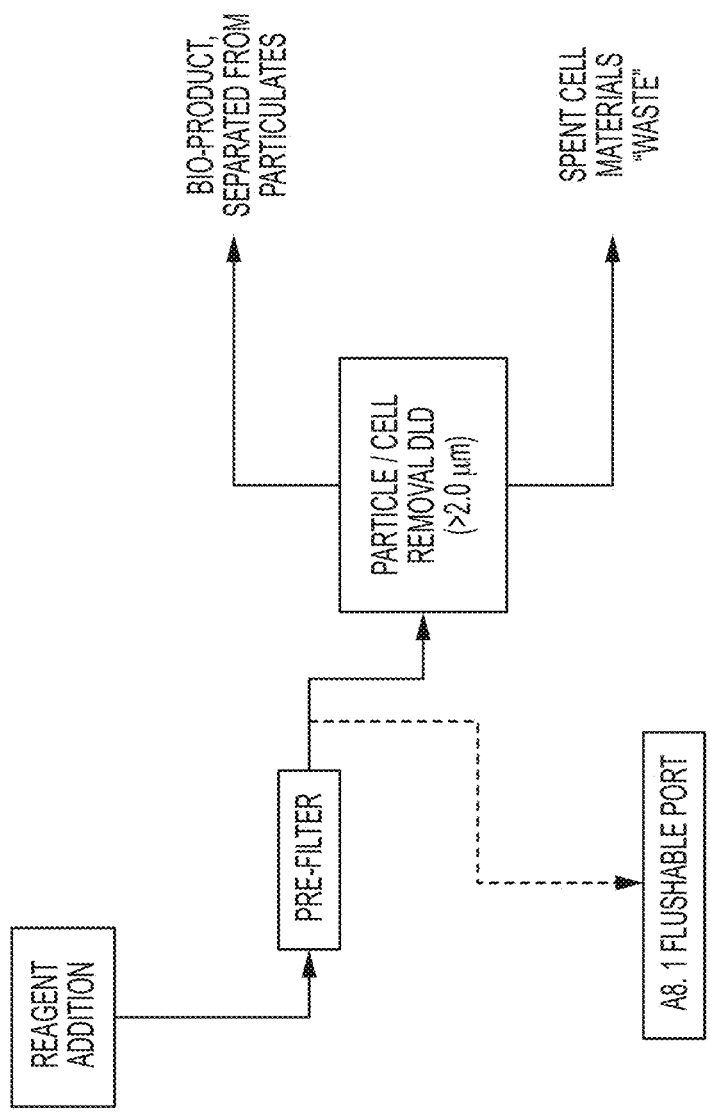
FIG. 15.

FIG. 15 is a schematic depicting the use of DLD in the purification of secreted products. In some instances, the cells may be in an aqueous suspension of buffer, growth medium, or the like, such that the cell secretes product into the suspension. Examples of such secreted products include proteins, peptides, enzymes, antibodies, fuel, biofuels such as those derived from algae, polymers, small molecules such as simple organic molecules, complex organic molecules, drugs and pro-drugs, carbohydrates and any combination thereof. Secreted products can include therapeutically useful proteins such as insulin, Imatinib, T cells, T cell receptors, Fc fusion proteins, anticoagulants, blood factors, bone morphogenetic proteins, engineered protein scaffolds, enzymes, growth factors, hormones, interferons, interleukins, and thrombolytics.

Purification might be carried out, for example, in situations where cells have a predetermined size that is greater than a predetermined size of the secreted compound, where the predetermined size of the cell is greater than or equal to a critical size, and the predetermined size of the secreted compound is less than the critical size. In such a configuration, when applied to a DLD device, the cells can be deflected in a first direction while the secreted compound can be deflected in a second direction, thereby separating the secreted compound from the cell. Also, a secreted protein may be captured by a large carrier that binds in a way that promotes DLD separation. DLD may then be performed and the carrier-protein complex may then be treated to further purify, or release, the protein.

Figure 16:
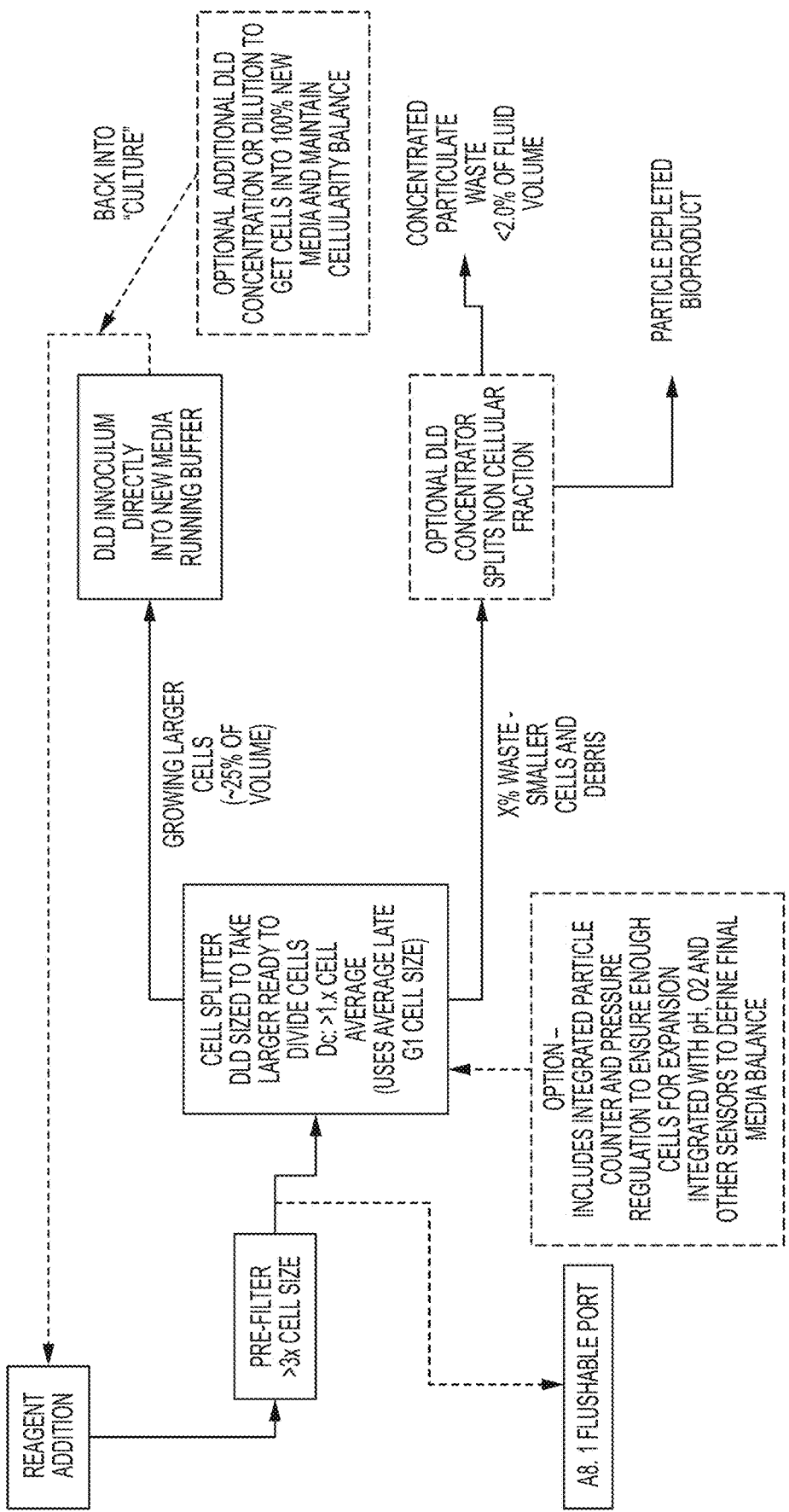
FIG. 16.
Figure 17:
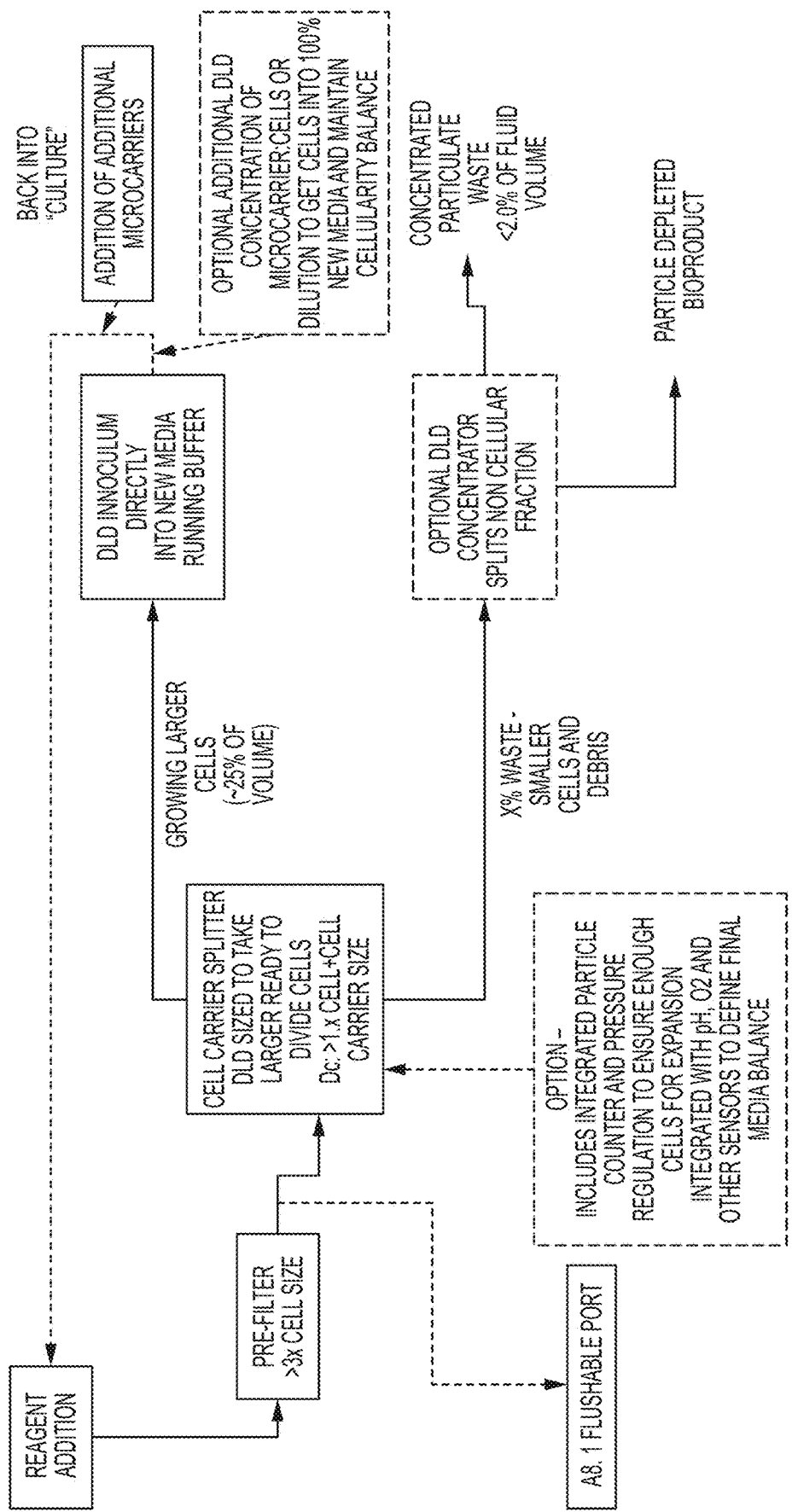
FIG. 17.
Figure 18A:
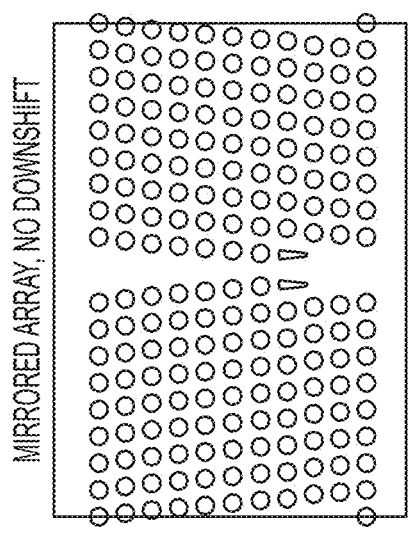
FIGS. 18A and 18B.
Figure 18B:
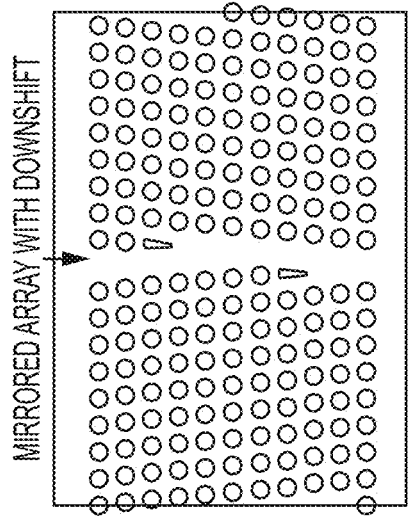

Such processes can be carried out in an iterative fashion such that a population of separated particles can be continuously looped back into a device for further separation. In this regard, FIGS. 16 and 17 are schematics of an iterative process in which separated cells are looped back into the DLD device after separation. In some instances, the cells may be looped from a first device into a second, different device with obstacles comprising different critical sizes. Such a system can allow systematic separation of a plurality of size ranges by manipulating the range of critical sizes. In other instances, cells may be looped back to the same device used previously to separate the isolated particles. This system can be advantageous for continuous purification of actively dividing cells or compounds being actively expressed. For example, such a method could be combined with the method of purifying the secreted product to both collect the secreted product from one flow stream and the cell producing the secreted product from another flow stream. Because the cells can continuously produce the secreted product, the purified cells can be reapplied to the device to continuously collect the secreted product from the cells.

F. Purity and Yields

The purity, yields and viability of cells produced by the DLD methods discussed herein will vary based on a number of factors including the nature of the starting material, the exact procedure employed and the characteristics of the DLD device. Preferably, purifications, yields and viabilities of at least 60% should be obtained with, higher percentages, at least 70, 80 or 90% being more preferred. In a preferred embodiment, methods may be used to isolate leukocytes from whole blood, apheresis products or leukapheresis products with at least 70% purity, yield and viability with higher percentages (at least 80%, 85%, or 90%) being preferred.

V. Technological Background

Without being held to any particular theory, a general discussion of some technical aspects of microfluidics may help in understanding factors that affect separations carried out in this field. A variety of microfabricated sieving matrices have been disclosed for separating particles (Chou, et. al., *Proc. Natl. Acad. Sci.* 96:13762 (1999); Han, et al., *Science* 288:1026 (2000); Huang, et al., *Nat. Biotechnol.* 20:1048 (2002); Turner et al., *Phys. Rev. Lett.* 88(12): 128103 (2002); Huang, et al., *Phys. Rev. Lett.* 89:178301 (2002); U.S. Pat. Nos. 5,427,663; 7,150,812; 6,881,317). Bump array (also known as "obstacle array") devices have been described, and their basic operation is explained, for example in U.S. Pat. No. 7,150,812, which is incorporated herein by reference in its entirety. A bump array operates essentially by segregating particles passing through an array (generally, a periodically-ordered array) of obstacles, with segregation occurring between particles that follow an "array direction" that is offset from the direction of bulk fluid flow or from the direction of an applied field (U.S. Pat. No. 7,150,812).

A. Bump Arrays

In some arrays, the geometry of adjacent obstacles is such that the portions of the obstacles defining the gap are symmetrical about the axis of the gap that extends in the direction of bulk fluid flow. The velocity or volumetric profile of fluid flow through such gaps is approximately parabolic across the gap, with fluid velocity and flux being zero at the surface of each obstacle defining the gap (assuming no-slip flow conditions) and reaching a maximum value at the center point of the gap. The profile being parabolic, a fluid layer of a given width adjacent to one of the obstacles defining the gap contains an equal proportion of fluid flux as a fluid layer of the same width adjacent to the other obstacle that defines the gap, meaning that the critical size of particles that are 'bumped' during passage through the gap is equal regardless of which obstacle the particle travels near.

In some cases, particle size-segregating performance of an obstacle array can be improved by shaping and disposing the obstacles such that the portions of adjacent obstacles that deflect fluid flow into a gap between obstacles are not symmetrical about the axis of the gap that extends in the direction of bulk fluid flow. Such lack of flow symmetry into the gap can lead to a non-symmetrical fluid flow profile within the gap. Concentration of fluid flow toward one side of a gap (i.e., a consequence of the non-symmetrical fluid flow profile through the gap) can reduce the critical size of particles that are induced to travel in the array direction, rather than in the direction of bulk fluid flow. This is because the non-symmetry of the flow profile causes differences between the width of the flow layer adjacent to one obstacle that contains a selected proportion of fluid flux through the gap and the width of the flow layer that contains the same proportion of fluid flux and that is adjacent to the other obstacle that defines the gap. The different widths of the fluid layers adjacent to obstacles define a gap that exhibits two different critical particle sizes. A particle traversing the gap can be bumped (i.e., travel in the array direction, rather than the bulk fluid flow direction) if it exceeds the critical size of the fluid layer in which it is carried. Thus, it is possible for a particle traversing a gap having a non-symmetrical flow profile to be bumped if the particle travels in the fluid layer adjacent to one obstacle, but to be not-bumped if it travels in the fluid layer adjacent to the other obstacle defining the gap.

In another aspect, decreasing the roundness of edges of obstacles that define gaps can improve the particle size-segregating performance of an obstacle array. By way of example, arrays of obstacles having a triangular cross-section with sharp vertices can exhibit a lower critical particle size than do arrays of identically-sized and -spaced triangular obstacles having rounded vertices.

Thus, by sharpening the edges of obstacles defining gaps in an obstacle array, the critical size of particles deflected in the array direction under the influence of bulk fluid flow can be decreased without necessarily reducing the size of the obstacles. Conversely, obstacles having sharper edges can be spaced farther apart than, but still yield particle segregation properties equivalent to, identically-sized obstacles having less sharp edges.

B. Fractionation Range

Objects separated by size on microfluidic include cells, biomolecules, inorganic beads, and other objects. Typical sizes fractionated range from 100 nanometers to 50 micrometers. However, larger and smaller particles may also sometimes be fractionated.

C. Volumes

Depending on design, a device or combination of devices might be used to process between about 10 µl to at least 500 µl of sample, between about 500 µl and about 40 mL of sample, between about 500 µl and about 20 mL of sample, between about 20 mL of sample and about 200 mL of sample, between about 40 mL of sample and about 200 mL of sample, or at least 200 mL of sample.

D. Channels

A device can comprise one or multiple channels with one or more inlets and one or more outlets. Inlets may be used for sample or crude (i.e., unpurified) fluid compositions, for buffers or to introduce reagents. Outlets may be used for collecting product or may be used as an outlet for waste. Channels may be about 0.5 to 100 mm in width and about 2-200 mm long but different widths and lengths are also possible. Depth may be 1-1000 µm and there may be anywhere from 1 to 100 channels or more present. Volumes may vary over a very wide range from a few µl to many ml and devices may have a plurality of zones (stages, or sections) with different configurations of obstacles.

E. Gap Size (Edge-to-Edge Distance Between Posts or Obstacles)

Gap size in an array of obstacles (edge-to-edge distance between posts or obstacles) can vary from about a few (e.g., 1-500) micrometers or be more than a millimeter. Obstacles may, in some embodiments have a diameter of 1-3000 micrometers and may have a variety of shapes (round, triangular, teardrop shaped, diamond shaped, square, rectangular etc.). A first row of posts can be located close to (e.g. within 5 µm) the inlet or be more than 1 mm away.

F. Stackable Chips

A device can include a plurality of stackable chips. A device can comprise about 1-50 chips. In some instances, a device may have a plurality of chips placed in series or in parallel or both.

VI. Inventive Concepts

The numbered paragraphs below present inventive concepts that are part of the present application. These concepts are expressed in the form of example paragraphs E1-E273.

E1. A method of engineering a population of target cells, comprising:
  a) isolating the target cells from a crude fluid composition wherein the isolation procedure comprises performing Deterministic Lateral Displacement (DLD) on a microfluidic device, wherein said device comprises:
    i) at least one channel extending from a sample inlet to one or more fluid outlets, wherein the channel is bounded by a first wall and a second wall opposite from the first wall;
    ii) an array of obstacles arranged in rows in the channel, each subsequent row of obstacles being shifted laterally with respect to a previous row, and wherein said obstacles are disposed in a manner such that, when said crude fluid composition is applied to an inlet of the device and fluidically passed through the channel, target cells flow to one or more collection outlets where an enriched product is collected and contaminant cells or particles that are of a different size than the target cells flow to one or more waste outlets that are separate from the collection outlets;
  b) genetically engineering the target cells obtained from the collection outlet(s) to have a desired phenotype.

E2. The method of E1, wherein said genetic engineering comprises transfecting or transducing the target cells and the genetically engineered target cells are expanded by culturing them in vitro.

E3. The method of E2, wherein the yield of target cells exhibiting the desired phenotype is at least 10% greater than identical cells isolated by Ficoll centrifugation and not subjected to DLD.

E4. The method of E1, wherein the crude fluid composition is blood or a composition that has been obtained by performing apheresis or leukapheresis on blood.

E5. The method of any one of E1-4, wherein the target cells are leukocytes.

E6. The method of any one of E1-4, wherein the target cells are B-cells, T cells, NK-cells, monocytes or progenitor cells.

E7. The method of any one of E1-4, wherein the target cell a dendritic cell.

E8. The method of any one of E1-7, wherein said crude fluid composition is obtained from a patient.

E9. The method of E8, wherein, target cells in the crude fluid composition are not bound to a carrier before being transduced or transfected.

E10. The method of E8, wherein target cells are bound to one or more carriers in a way that promotes or complements DLD separation before performing DLD.

E11. The method of E9, wherein target cells are bound to one or more carriers in a way that promotes or complements DLD separation after performing DLD and either before or after transducing or transfecting them.

E12. The method of E10 or E11, wherein said one or more carriers comprise on their surface an affinity agent that binds specifically to said target cells.

E13. The method of E12, wherein said agent is an antibody, an activator, a hapten or an aptamer.

E14. The method of any one of E10-13, wherein the diameter of said carriers is at least as large as that of the target cells.

E15. The method of any one of E10-13, wherein the diameters of all of said carriers are no more than 50% as large as that of the target cells.

E16. The method of any one of E10-13, wherein the diameters of all of said carriers are at least two times larger than that of the target cells.

E17. The method of any one of E10-13, wherein the diameters of all of said carriers are no more than 25% as large as that of the target cells.

E18. The method of any one of E10-13, wherein one group of carriers has a diameter at least as large as the target cells and a second group of carriers has a diameter no more than 50% as large as that of the target cells.

E19. The method of any one of E10-13, wherein one group of carriers has a diameter at least twice as large as the target cells and a second group of carriers has a diameter no more than 25% as large as the target cells.

E20. The method of any one of E10-19, wherein said carriers are made of collagen or a polysaccharide.

E21. The method of any one of E10-20, wherein said carriers are made of gelatin or alginate.

E22. The method of any one of E10-21, wherein the crude fluid composition is obtained from a patient and no more than four hours elapse from the time that the obtaining of the crude fluid composition is complete until the target cells are first bound to a carrier.

E23. The method of any one of E10-21, wherein the crude fluid composition is an apheresis or leukapheresis product derived from the blood of a patient and no more than four hours elapse from the time that apheresis or leukapheresis is completed until the target cells are first bound to a carrier.

E24. The method of any one of E1-23, wherein the crude fluid composition is obtained from a patient and no more than five hours elapse from the time that the obtaining of the crude fluid composition is complete until the first time that target cells are transfected or transduced.

E25. The method of any one of E1-23, wherein the crude fluid composition is an apheresis or leukapheresis product derived from the blood of a patient and no more than five hours elapse from the time that apheresis or leukapheresis is completed until the first time that target cells are transfected or transduced.

E26. The method of either E24 or E25, wherein no more than four hours elapse until the first time that target cells are transfected or transduced.

E27. A method of producing Chimeric Antigen Receptor (CAR) T cells, comprising:
  a) obtaining a crude fluid composition comprising T cells;
  b) performing Deterministic Lateral Displacement (DLD) on the crude fluid composition using a microfluidic device comprising:
    i) at least one channel extending from a sample inlet to one or more fluid outlets, wherein the channel is bounded by a first wall and a second wall opposite from the first wall;
    ii) an array of obstacles arranged in rows in the channel, each subsequent row of obstacles being shifted laterally with respect to a previous row, and wherein said obstacles are disposed in a manner such that, when the crude fluid composition is applied to an inlet of the device and fluidically passed through the channel, T cells in the composition flow to one or more collection outlets where an enriched product is collected, and cells, or particles that are in the crude fluid composition and that are of a different size than the T cells, flow to one or more waste outlets that are separate from the collection outlets;

c) genetically engineering the T cells in the enriched product obtained in step b) to produce the chimeric antigen receptors (CARs) on their surface.

E28. The method of E27, wherein said crude fluid composition is an apheresis product or leukapheresis product obtained from blood from a patient and wherein, when the crude fluid composition is applied to an inlet of the device and fluidically passed through the channel, T cells in the composition flow to one or more collection outlets where an enriched product is collected, and red blood, platelets or other particles that are in the crude fluid composition and that are of a different size, flow to one or more waste outlets that are separate from the collection outlets.

E29. The method of either E27 or E28, wherein said genetic engineering comprises transfecting or transducing the target cells and the genetically engineered target cells are expanded further by growing the cells in vitro.

E30. The method of any one of E27-29, wherein the yield of T cells expressing the chimeric receptors on their surface is at least 10% greater than T cells isolated from the crude fluid composition by Ficoll centrifugation and not subjected to DLD.

E31. The method of E30, wherein the yield of T cells expressing the chimeric receptors on their surface is at least 20% greater than T cells isolated from the crude fluid composition by Ficoll centrifugation and not subjected to DLD.

E32. The method of E30, wherein the yield of T cells expressing the chimeric receptors on their surface is at least 50% greater than T cells isolated from the crude fluid composition by Ficoll centrifugation and not subjected to DLD.

E33. The method of any one of E27-32, wherein said CAR comprises a) an extracellular region comprising antigen binding domain; b) a transmembrane region; c) an intracellular region and wherein said CAR T cells optionally comprise one or more recombinant sequences that provide the cells with a molecular switch that, when triggered, reduce CAR T cell number or activity.

E34. The method of E33, wherein said antigen binding domain is a single chain variable fragment (scFv), from antigen binding regions of both heavy and light chains of a monoclonal antibody.

E35. The method of E33 or E34 wherein said CAR comprises a hinge region of 2-20 amino acids connecting the extracellular region and the transmembrane region.

E36. The method of E35, wherein said transmembrane region comprises CD8 or CD28 protein sequences.

E37. The method of any one of E33-36, wherein said intracellular region comprises a signaling domain derived from CD3-zeta, CD137 or a CD28 intracellular domain.

E38. The method of any one of E27-37, wherein said crude fluid composition comprising T cells is obtained from a patient with cancer, an autoimmune disease or an infectious disease.

E39. The method of E38 wherein, after obtaining the crude fluid composition comprising T cells, the T cells in the fluid composition are bound to one or more carriers in a way that promotes DLD separation.

E40. The method of E39, wherein T cells are bound to one or more carriers in a way that promotes DLD separation before performing DLD.

E41. The method of E39, wherein T cells are bound to one or more carriers in a way that promotes DLD separation after performing DLD and either before or after they are genetically engineered.

E42. The method of E39-41, wherein said one or more carriers comprise on their surface an antibody or activator that binds specifically to said T cells.

E43. The method of any one of E39-42, wherein the diameters of all of said carriers are at least as large as that of the T cells.

E44. The method of any one of E39-42, wherein the diameters of all of said carriers are no more than 50% as large as that of the T cells.

E45. The method of any one of E39-42, wherein the diameters of all of said carriers are at least two times larger than that of the T cells.

E46. The method of any one of E39-42, wherein the diameters of all of said carriers are no more than 25% as large as that of the T cells.

E47. The method of any one of E39-42, wherein one group of carriers has a diameter at least as large as the T cells and a second group of carriers has a diameter no more than 50% as large as that of the T cells.

E48. The method of any one of E39-42, wherein one group of carriers has a diameter at least twice as large as the T cells and a second group of carriers has a diameter no more than 25% as large as the T cells.

E49. The method of any one of E39-48, wherein said carriers are made of collagen or a polysaccharide.

E50. The method of any one of E39-49, wherein said carriers are made of gelatin or alginate.

E51. The method of any one of E39-50, wherein no more than four hours elapse from the time that obtaining of the crude fluid composition comprising T cells is completed until the T cells are bound to a carrier.

E52. The method of any one of E39-50, wherein the crude fluid composition is an apheresis or leukapheresis product derived from the blood of a patient and no more than four hours elapse from the time that apheresis or leukapheresis is completed until the target cells are bound to a carrier.

E53. The method of any one of E27-50, wherein no more than five hours elapse from the time that obtaining of the crude fluid composition comprising T cells is completed until the first time that T cells are transfected or transduced.

E54. The method of any one of E27-50, wherein the crude fluid composition is an apheresis or leukapheresis product derived from the blood of a patient and no more than five hours elapse from the time that apheresis or leukapheresis is completed until the first time that T cells are transfected or transduced.

E55. The method of either E53 or E54, wherein no more than four hours elapse until the first time that T cells are transfected or transduced.

E56. The method of any one of E27-55 where all steps in producing the CAR T cells are performed at the same facility where the a crude fluid composition comprising T cells is obtained and all steps are completed in a total of no more than four hours.

E57. CART cells made by the method of any one of E27-55.

E58. A method of treating a patient for cancer, an autoimmune disease, or an infectious disease, comprising administering to said patient CAR T cells engineered to express chimeric antigen receptors that recognize antigens on cancer cells, autoimmune cells or infectious cells from said patient, wherein said CAR T cells have been produced by a process comprising:

a) obtaining a crude fluid composition comprising T cells from a patient;
b) performing Deterministic Lateral Displacement (DLD) on the crude fluid composition using a microfluidic device comprising:
  i) at least one channel extending from a sample inlet to one or more fluid outlets, wherein the channel is bounded by a first wall and a second wall opposite from the first wall;
  ii) an array of obstacles arranged in rows in the channel, each subsequent row of obstacles being shifted laterally with respect to a previous row, and wherein said obstacles are disposed in a manner such that, when the crude fluid composition is applied to an inlet of the device and fluidically passed through the channel, T cells in the composition flow to one or more collection outlets where an enriched product is collected, and cells, or particles that are in the crude fluid composition and that are of a different size than the T cells, flow to one or more waste outlets that are separate from the collection outlets;
c) genetically engineering the T cells obtained in step b) to express chimeric antigen receptors (CARs) on their surface;
d) expanding the number of engineered T cells by growing the cells in vitro; and
e) administering the engineered T cells to the patient from which the crude fluid composition was obtained.

E59. The method of E58, wherein said crude fluid composition is an apheresis product or leukapheresis product obtained from blood from said patient and wherein, when the crude fluid composition is applied to an inlet of the device and fluidically passed through the channel, T cells in the composition flow to one or more collection outlets where an enriched product is collected, and red blood cells, platelets or other particles that are in the crude fluid composition and that are of a different size, flow to one more waste outlets that are separate from the collection outlets.

E60. The method of E58 or E59, wherein genetic engineering comprises transfecting or transducing the target cells.

E61. The method of E60, wherein the yield of cells expressing the chimeric receptors on their surface is at least 10% greater than T cells isolated from the crude fluid composition by Ficoll centrifugation and not subjected to DLD.

E62. The method of E60, wherein the yield of target cells expressing the chimeric receptors on their surface is at least 50% greater than T cells isolated from the crude fluid composition by Ficoll centrifugation and not subjected to DLD.

E63. The method of any one of E58-62, wherein said CAR comprises a) an extracellular region comprising antigen binding domain; b) a transmembrane region; and c) an intracellular region and wherein said CAR T cells optionally comprise one or more recombinant sequences that provide the cells with a molecular switch that, when triggered, reduce CAR T cell number or activity.

E64. The method of E63, wherein said antigen binding domain is a single chain variable fragment (scFv), from the antigen binding regions of both heavy and light chains of a monoclonal antibody.

E65. The method of E63 or E64 wherein said CAR comprises a hinge region of 2-20 amino acids connecting the extracellular region and the transmembrane region.

E66. The method of any one of E63-65, wherein said transmembrane region comprises CD8 or CD28 protein sequences.

E67. The method of any one of E63-66, wherein said intracellular region comprises a signaling domain derived from CD3-zeta, CD137, a CD28 intracellular domain.

E68. The method of any one of E58-67, wherein said patient has leukemia.

E69. The method of E68, wherein said leukemia is acute lymphoblastic leukemia.

E70. The method of E68 or E69, wherein said CAR recognizes as an antigen CD19 or CD20.

E71. The method of any one of E58-67, wherein said patient has a solid tumor.

E72. The method of E71, wherein said CAR recognizes an antigen selected from the group consisting of: CD22; RORI; mesothelin; CD33/IL3Ra; c-Met; PSMA; Glycolipid F77; EGFRvIII; GD-2; NY-ESO-1 TCR; MAGE A3 TCR; and combinations thereof.

E73. The method of any one of E58-72 wherein, after obtaining the crude fluid composition comprising T cells, the T cells in the fluid are bound to a carrier in a way that promotes DLD separation.

E74. The method of E73, wherein T cells are bound to one or more carriers in a way that promotes DLD separation before performing DLD.

E75. The method of E73, wherein T cells are bound to one or more carriers in a way that promotes DLD separation after performing DLD and either before or after the T cells are genetically engineered to express chimeric receptors.

E76. The method of E73-75, wherein said one or more carriers comprise on their surface an antibody or activator that binds specifically to said T cells.

E77. The method of any one of E73-76, wherein the diameters of all of said carriers are at least as large as that of the T cells.

E78. The method of any one of E73-76, wherein the diameters of all of said carriers are no more than 50% as large as that of the T cells.

E79. The method of any one of E73-76, wherein the diameters of all of said carriers are at least two times larger than that of the T cells.

E80. The method of any one of E73-76, wherein the diameters of all of said carriers are no more than 25% as large as that of the T cells.

E81. The method of E80, wherein one group of carriers has a diameter at least as large as the T cells and a second group of carriers has a diameter no more than 50% as large as that of the T cells.

E82. The method of any one of E73-81, wherein one group of carriers has a diameter at least twice as large as the T cells and a second group of carriers has a diameter no more than 25% as large as the T cells.

E83. The method of any one of E73-82, wherein said carriers are made of collagen or a polysaccharide.

E84. The method of any one of E73-83, wherein said carriers are made of gelatin or alginate.

E85. The method of any one of E73-84, wherein no more than four hours elapse from the time that obtaining of the crude fluid composition comprising T cells is completed until the T cells are bound to a carrier.

E86. The method of any one of E73-84, wherein the crude fluid composition is an apheresis or leukapheresis product derived from the blood of a patient and no more than four hours elapse from the time that apheresis or leukapheresis is completed until the target cells are bound to a carrier.

E87. The method of any one of E73-84, wherein no more than five hours elapse from the time that obtaining of the crude fluid composition comprising T cells is completed until the first time that the T cells are transfected or transduced.

E88. The method of any one of E73-84, wherein the crude fluid composition is an apheresis or leukapheresis product derived from the blood of a patient and no more than five hours elapse from the time that apheresis or leukapheresis is completed until the first time that T cells are transfected or transduced.

E89. The method of E87 or E88, wherein no more than four hours elapse until the first time that T cells are transfected or transduced.

E90. The method of any one of E58-89, wherein T cells are available for administration to a patient at least 1 day earlier than for cells processed via a method not including DLD.

E91. The method of any one of E58-89, wherein target cells are available for administration to a patient at least 3 days earlier than for cells processed via a method not including DLD.

E92. A method of collecting target cells from a patient comprising:
- a) obtaining from the patient a crude fluid composition comprising target cells;
- b) performing Deterministic Lateral Displacement (DLD) on the crude fluid composition comprising target cells using a microfluidic device to obtain a composition enriched in target cells;

wherein, either before or after DLD, target cells are bound to one or more carriers in a way that promotes DLD separation and wherein no more than five hours elapse from the time that the obtaining of the crude fluid composition comprising target cells from the patient is completed until the target cells are bound to a carrier.

E93. The method of E92, wherein said one or more carriers comprise on their surface an antibody or activator that binds specifically to said target cells.

E94. The method of either E92 or E93, wherein the diameters of all of said carriers are at least as large as that of the target cells.

E95. The method of either E92 or E93, wherein the diameters of all of said carriers are no more than 50% as large as that of the target cells.

E96. The method of either E92 or E93, wherein the diameters of all of said carriers are at least two times larger than that of the target cells.

E97. The method of either E92 or E93, wherein the diameters of all of said carriers are no more than 25% as large as that of the target cells.

E98. The method of either E92 or E93, wherein one group of carriers has a diameter at least as large as the target cells and a second group of carriers has a diameter no more than 50% as large as that of the target cells.

E99. The method of either E92 or E93, wherein one group of carriers has a diameter at least twice as large as the T cells and a second group of carriers has a diameter no more than 25% as large as the T cells.

E100. The method of any one of E92-99, wherein said carriers are made of collagen or a polysaccharide.

E101. The method of any one of E92-100, wherein said carriers are made of gelatin or alginate.

E102. The method of any one of E92-101, wherein no more than four hours elapse from the time that the obtaining of the crude fluid composition comprising target cells is completed until the target cells are bound to a carrier.

E103. The method of any one of E92-101, wherein no more than three hours elapse from the time that the obtaining of the crude fluid composition comprising target cells is completed until the target cells are bound to a carrier.

E104. The method of any one of E92-103, wherein said crude fluid composition comprising target cells is obtained by performing apheresis or leukapheresis on blood from the patient.

E105. The method of any one of E92-104 wherein target cells in the composition enriched in target cells by DLD are transduced using a viral vector.

E106. The method of E105 wherein target cells are transfected electrically, chemically or by means of nanoparticles.

E107. The method of any one of E92-106, wherein said microfluidic device comprises:
- a) at least one channel extending from a sample inlet to one or more fluid outlets, wherein the channel is bounded by a first wall and a second wall opposite from the first wall;
- b) an array of obstacles arranged in rows in the channel, each subsequent row of obstacles being shifted laterally with respect to a previous row, and wherein said obstacles are disposed in a manner such that, when said crude fluid composition comprising target cells is applied to an inlet of the device and fluidically passed through the channel, target cells flow to one or more collection outlets where an enriched product is collected and contaminant cells, or particles that are in the crude fluid composition and that are of a different size than the target cells flow to one or more waste outlets that are separate from the collection outlets.

E108. The method of any one of E92-107, wherein said target cells are T cells.

E109. The method of E108, wherein said T cells are selected from the group consisting of: Natural Killer T cells; Central Memory T cells; Helper T cells and Regulatory T cells.

E110. The method of any one of E92-107, wherein said target cells are stem cells.

E111. The method of any one of E92-107, wherein said target cells are B cells, macrophages, dendritic cells, or granulocytes.

E112. The method of any one of E92-111, wherein said crude fluid composition comprising target cells comprises one or more additives that act as anticoagulants or that prevent the activation of platelets.

E113. The method of E112, wherein said additives are selected from the group consisting of ticlopidine, inosine, protoctechuic acid, acetylsalicylic acid, and tirofiban.

E114. The method of any one of E92-113, wherein steps a) and b) are both carried out at the site where the crude fluid composition comprising target cells is obtained from the patient.

E115. The method of any one of E92-114, wherein no more than four hours elapse from the time that the obtaining of the crude fluid composition comprising target cells from the patient is completed until the target cells are bound to a carrier.

E116. The method of any one of E92-114, wherein the crude fluid composition is an apheresis or leukapheresis product derived from the blood of the patient and no more than four hours elapse from the time that apheresis or leukapheresis is completed until the target cells are bound to a carrier.

E117. The method of any one of E92-116, wherein said method further comprises:
- c) genetically engineering and/or expanded cells in number; and/or d) treating the same patient from which the target cells were obtained with the target cells collected.

E118. The method of E117, wherein, after step d), said target cells are cryopreserved.

E119. The method of either E117 or E118, wherein target cells that are cultured in step c) are T cells that are cultured in the presence of an activator.

E120. The method of E119, wherein the activator is bound to a carrier.

E121. The method of any one of E58-89, wherein target cells are available for administration to the patient at least 1 day earlier than for cells processed via a method not including DLD.

E122. The method of any one of E58-89, wherein target cells are available for administration to the patient at least 3 days earlier than for cells processed via a method not including DLD.

E123. Target cells produced by the method of any one of E92-122.

E124. A method of treating a patient for a disease or condition comprising administering to said patient the target cells of E123.

E125. A method of separating an adherent cell from a plurality of other cells comprising:
  a) contacting a crude fluid composition comprising the plurality of other cells and the adherent cell with one or more carriers that bind in a way that promotes DLD separation, wherein the adherent cell is at least partially associated with carriers upon or after contact to generate a carrier associated adherent cell complex, wherein the carrier associated adherent cell complex comprises an increased size relative to cells in the plurality of other cells, and wherein the size of the carrier associated adherent cell complex is greater than or equal to a critical size, and the cells in the plurality of other cells comprise a size less than the critical size;
  b) applying the crude fluid composition to a device, wherein the device comprises an array of obstacles arranged in rows, wherein the rows are shifted laterally with respect to one another, wherein the rows are configured to deflect a particle greater than or equal to the critical size in a first direction and a particle less than the critical size in a second direction; and
  c) flowing the sample comprising the carrier associated adherent cell complex through the device, wherein the carrier associated adherent cell complex is deflected by the obstacles in the first direction, and the cells in the plurality of other cells are deflected in the second direction, thereby separating the carrier associated adherent cell complex from the other cells of the plurality;
  d) collecting a fluid composition comprising the separated carrier associated adherent cell complex.

E126. The method of E125, wherein said adherent cell is collected from a patient as part of a crude fluid composition comprising said adherent cell and a plurality of other cells, and wherein no more than three hours elapse from the time that the obtaining of the crude fluid composition from the patient is completed until the adherent cell is bound to a carrier for the first time.

E127. The method of E125, wherein no more than two hours elapse from the time that the obtaining of the crude fluid composition from the patient is completed until the adherent cell is bound to the carrier for the first time.

E128. The method of E125, wherein no more than one hour elapses from the time that the obtaining of the crude fluid composition from the patient is completed until the adherent cell is bound to the carrier for the first time.

E129. The method of E125, wherein no more than four hours elapse from the time that the obtaining of the crude fluid composition from the patient is completed until the adherent cell or the carrier adherent cell complex is collected from the device for the first time.

E130. The method of E125, wherein no more than four hours elapse from the time that the obtaining of the crude fluid composition from the patient is completed until the adherent cell or the carrier adherent cell complex is collected from the device for the first time.

E131 The method of any one of E125-130, wherein said carrier comprises on its surface an antibody or activator that binds specifically to said adherent cell.

E132. The method of any one of E125-131, wherein the diameter of said carrier is at least as large as that of the adherent cell.

E133. The method of any one of E125-131, wherein the diameters of all of said carriers are at least twice as large as that of the adherent cell.

E134. The method of any one of E125-131, wherein the diameters of all of said carriers are at least ten times as large as that of the adherent cell.

E135. The method of any one of E125-131, wherein the diameters of all of said carriers are 10-600 µm.

E136. The method of any one of E125-135, wherein the adherent cell is selected from the group consisting of: an MRC-5 cell; a HeLa cell; a Vero cell; an NIH 3T3 cell; an L929 cell; a Sf21 cell; a Sf9 cell; an A549 cell; an A9 cell; an AtT-20 cell; a BALB/3T3 cell; a BHK-21 cell; a BHL-100 cell; a BT cell; a Caco-2 cell; a Chang cell; a Clone 9 cell; a Clone M-3 cell; a COS-1 cell; a COS-3 cell; a COS-7 cell; a CRFK cell; a CV-1 cell; a D-17 cell; a Daudi cell; a GH1 cell; a GH3 cell; an HaK cell; an HCT-15 cell; an HL-60 cell; an HT-1080 cell; a HEK cell, HT-29 cell; an HUVEC cell; an I-10 cell; an IM-9 cell; a JEG-2 cell; a Jensen cell; a Jurkat cell; a K-562 cell; a KB cell; a KG-1 cell; an L2 cell; an LLC-WRC 256 cell; a McCoy cell; a MCF7 cell; a WI-38 cell; a WISH cell; an XC cell; a Y-1 cell; a CHO cell; a Raw 264.7 cell; a HEP G2 cell; a BAE-1 cell; an SH-SYS5 cell, and any derivative thereof.

E137. The method of any one of E125-135, wherein the adherent cell is a stem cell.

E138. A method of separating an activated cell from a plurality of other cells comprising:
  a) contacting a crude fluid composition comprising a cell capable of activation and the plurality of other cells with one or more carriers, wherein at least one carrier comprises a cell activator, wherein the cell activator is at least partially associated with the cell capable of activation by the cell activator upon or after contact to generate a carrier associated cell complex, wherein the association of the cell activator with the cell capable of activation by the cell activator at least partially activates the cell capable of activation, wherein the carrier associated cell complex comprises an increased size relative to cells in the plurality of other cells, and wherein a size of the carrier associated cell complex is greater than or equal to a critical size, and the cells in the plurality of other cells comprise a size less than the critical size;
  b) applying the sample to a device, wherein the device comprises an array of obstacles arranged in rows; wherein the rows are shifted laterally with respect to one another, wherein the rows are configured to deflect a particle greater than or equal to the critical size in a first direction and a particle less than the critical size in a second direction; and c) flowing the sample through the device, wherein the carrier associated cell complex is deflected by the obstacles in the first direction, and the cells in the plurality of other cells are deflected in the second direction, thereby separating the activated cell from the other cells of the plurality;

d) collecting a fluid composition comprising the separated carrier associated cell complex.

E139. The method of E138, wherein the cell capable of activation is selected from the group consisting of: a T cell, a B cell, a regulatory T cell, a macrophage, a dendritic cell, a granulocyte, an innate lymphoid cell, a megakaryocyte, a natural killer cell, a thrombocyte, a synoviocyte, a beta cell, a liver cell, a pancreatic cell; a DE3 lysogenized cell, a yeast cell, a plant cell, and a stem cell.

E140. The method of E138 or E139, wherein the cell activator is a protein.

E141. The method of E140, wherein the protein is an antibody.

E142. The method of E140, wherein the protein is selected from the group consisting of: CD3, CD28, an antigen, a helper T cell, a receptor, a cytokine, a glycoprotein, and any combination thereof E143. The method of E138, wherein the cell activator is selected from the group consisting of insulin, IPTG, lactose, allolactose, a lipid, a glycoside, a terpene, a steroid, an alkaloid, and any combination thereof.

E144. The method of any one of E138-143, wherein said cell capable of activation is collected from a patient as part of a crude fluid composition comprising said cell capable of activation and a plurality of other cells, and wherein no more than four hours elapse from the time that the obtaining of the crude fluid composition from the patient is completed until the cell capable of activation is bound to the carrier.

E145. The method of any one of E138-143, wherein no more than three hours elapse from the time that the obtaining of the crude fluid composition from the patient is completed until the cell capable of activation is bound to the carrier.

E146 The method of E138-143, wherein no more than two hours elapse from the time that the obtaining of the crude fluid composition from the patient is completed until the cell capable of activation is bound to the carrier.

E147. The method of any one of E138-143, wherein no more than four hours elapse from the time that the obtaining of the crude fluid composition from the patient is completed until step c) is completed.

E148. The method of any one of E138-143, wherein no more than three hours elapse from the time that the obtaining of the crude fluid composition from the patient is completed until step c) is completed.

E149. The method of any one of E138-148, wherein the diameters of all of said carriers are at least as large as the cell capable of activation.

E150. The method of any one of E138-148, wherein the diameters of all of said carriers are at least twice as large as that of the cell capable of activation.

E151. The method of any one of E138-148, wherein the diameters of all of said carriers are at least ten times as large as that of the cell capable of activation.

E152. The method of any one of E138-148, wherein the diameters of said carriers are 10-600 μm.

E153. A method of continuously purifying a secreted product from a cell comprising:

a) obtaining a fluid composition comprising the cell, wherein the cell is suspended in the fluid composition, wherein the cell secretes the secreted product into the suspension, wherein the cell has a predetermined size that is greater than a predetermined size of the secreted product, and wherein the predetermined size of the cell is greater than or equal to a critical size, and the predetermined size of the secreted product is less than the critical size;

b) applying the fluid composition comprising the cell to a device, wherein the device comprises an array of obstacles arranged in rows; wherein the rows are shifted laterally with respect to one another, wherein the rows are configured to deflect a particle greater than or equal to the critical size in a first direction and a particle less than the critical size in a second direction;

c) flowing the sample through the device, wherein the cell is deflected by the obstacles in the first direction, and the secreted product is deflected in the second direction, thereby separating the secreted product from the cell;

d) collecting the secreted product, thereby producing a sample of the secreted product that is substantially pure;

e) collecting a recovered fluid composition comprising the separated cell; and f) re-applying the recovered fluid composition comprising the separated cell to the device and repeating steps (a) through (e); thereby continuously purifying the secreted product from the cell.

E154. The method of E153, wherein the secreted product is selected from the group consisting of: a protein, an antibody, a biofuel, a polymer, a small molecule, and any combination thereof.

E155. The method of E153, wherein the cell is selected from the group consisting of: a bacterial cell, an algae cell, a mammalian cell, and a tumor cell.

E156. A method for decreasing the ratio of platelets to leukocytes in an apheresis sample, comprising performing deterministic lateral displacement (DLD) on the sample, in the absence of centrifugation or elutriation, wherein a product is obtained in which the ratio of platelets to leukocytes is at least 20% lower than the ratio obtained with the same procedure performed using centrifugation or elutriation instead of DLD.

E157. The method of E156, wherein a product is obtained in which the ratio of platelets to leukocytes is at least 20% lower than the ratio obtained with the same procedure performed using density gradient centrifugation or counterflow centrifugation.

E158. The method of E156, wherein a product is obtained in which the ratio of platelets to leukocytes is at least 20% lower than the ratio obtained with the same procedure performed using elutriation.

E159. The method of E156, wherein a product is obtained in which the ratio of platelets to leukocytes is at least 50% lower than the ratio obtained using centrifugation or elutriation instead of DLD.

E160. The method of any one of E156-159, wherein there are no separation steps performed on the apheresis sample prior to DLD.

E161. The method of any one of E156-160, wherein DLD is performed in a buffer that does not comprise intercalators that alter the size of platelets and that does not promote platelet aggregation.

E162. The method of any one of E156-159 wherein DLD is performed in a buffer that does not comprise dextran or other highly charge polymers.

E163. The method of any one of E156-162, wherein the total number of platelets in the product is at least 70% lower than in the apheresis sample.

E164. The method of any one of E156-163, wherein the total number of platelets in the product is at least 90% lower than in the apheresis sample.

E165. A method for purifying T cells from an apheresis sample, comprising performing DLD on the sample, followed by an affinity separation step and expansion of the T cells by culturing in the presence of activator, wherein the number of T cells obtained is at least twice as high as the number produced by the same procedure performed using Ficoll centrifugation instead of DLD.

E166. The method of E165, wherein the affinity separation step comprises the use of magnetic beads or particles comprising an antibody binding to CD3.

E167. The method of E165, wherein the number of T cells obtained after 14 days in culture is at least two times higher than the number produced by the same procedure performed using Ficoll centrifugation instead of DLD.

E168. The method of E165, wherein the number of T cells obtained after 14 days in culture is at least four times higher than the number produced by the same procedure performed using Ficoll centrifugation instead of DLD.

E169. The method of any one of E156-168 wherein, when cells in the DLD product are transformed with a vector to express a recombinant phenotype, the yield of cells exhibiting the desired phenotype is at least 10% greater than for identical cells isolated by Ficoll centrifugation and not subjected to DLD.

E170. The method of any one of E156-169, wherein when cells in the DLD product are transformed with a vector to express a recombinant phenotype, the yield of T cells exhibiting the desired phenotype is at least 20% greater than for identical cells isolated by Ficoll centrifugation and not subjected to DLD.

E171. The method of any one of E163-165 wherein the percentage of memory T cells in the DLD product relative to the total number of T cells is at least 10% higher than the percentage produced using the same procedure but with Ficoll centrifugation instead of DLD.

E172. The method of any one of E156-171, wherein the method is used to produce T cells for CAR T cell therapy and the time needed to produce a sufficient number of cells to treat a patient is reduced by at least 20% using DLD instead of Ficoll centrifugation.

E173. The method of E172, wherein the process for producing CART cells does not include a step in which cells are frozen.

E174. The method of either E172 or E173, wherein the processing of T cells is performed at the same site where apheresis is performed.

E175. The method of any one of E172-174, wherein T cells are genetically transformed at the same site where apheresis is performed.

E176. The method of any one of E156-169, wherein no more than one hour elapses from the time that the apheresis sample collection is completed until the time that DLD is performed.

E177. A method for decreasing the ratio of platelets to leukocytes in an apheresis sample, comprising performing deterministic lateral displacement (DLD) on the sample, in the absence of centrifugation or elutriation, wherein a product is obtained in which the total number of platelets in the product is at least 90% lower than in the apheresis sample.

E178. The method of E177, wherein DLD is performed in a buffer that does not comprise intercalators that alter the size of platelets and that does not promote platelet aggregation.

E179. The method of E177, wherein DLD is performed in a buffer that does not comprise dextran or other highly charge polymers.

E180. A method of producing CART cells, comprising:
a) obtaining a sample composition from a patient by apheresis, wherein said sample composition comprises T cells;
b) performing DLD on the sample composition to reduce the total number of platelets present by at least 70%, wherein DLD is carried out on a microfluidic device comprising:
i) at least one channel extending from a sample inlet to one or more fluid outlets, wherein the channel is bounded by a first wall and a second wall opposite from the first wall;
ii) an array of obstacles arranged in rows in the channel, each subsequent row of obstacles being shifted laterally with respect to a previous row, and wherein said obstacles are disposed in a manner such that, when the crude fluid composition is applied to an inlet of the device and fluidically passed through the channel, T cells in the composition flow to one or more collection outlets where an enriched product is collected, and wherein platelets and other materials smaller than T cells flow to one or more waste outlets that are separate from the collection outlets;
c) genetically engineering the T cells in the enriched product obtained in step b) to produce chimeric antigen receptors (CARs) on their surface;
d) culturing the T cells to expand their number;
e) transferring the T cells into a pharmaceutical composition for administration to a patient.

E181. The method of E180, wherein at least 90% of platelets are removed in step b).

E182. The method of either E180 or E181, wherein all isolation steps and concentration steps are carried out using DLD.

E183. The method of any one of E180-182, wherein prior to, or during culturing, cells are exposed to a T cell activator.

E184. The method of any one of E180-183, wherein, in step b) and prior to step c), cells are transferred into a medium in which a T cell activator is present or added.

E185. The method of E184, wherein the medium containing activator is processed by DLD to separate activator from cells and to transfer cells into a medium in which a vector for recombinantly engineering cells is present or added.

E186. The method of any one of E180-185, wherein cells are not frozen until they are transferred into a pharmaceutical composition for administration to a patient.

E187. The method of any one of E180-185, wherein cells are not frozen at any step.

E188. The method of any one of E180-187, wherein, compared to a procedure in which cells are isolated or concentrated by a method other than DLD, the process is completed at least one day sooner.

E189. The method of any one of E180-187, wherein, compared to a procedure in which cells are isolated or concentrated by a method other than DLD, the process is completed at least three days sooner.

E190. The method of any one of E180-187, wherein, compared to a procedure in which cells are isolated or concentrated by a method other than DLD, the process is completed at least five days sooner.

E191. The method of any one of E180-187, wherein, compared to a procedure in which cells are isolated or concentrated by a method other than DLD, the process is completed at least ten days sooner.

E192. The method of any one of E180-191, wherein, in step d), the number of T cells obtained after 14 days in culture is at least two times higher than the number produced by the same procedure performed using Ficoll centrifugation instead of DLD.

E193. The method of any one of E180-191, wherein, in step d), the number of T cells obtained after 14 days in culture is at least four times higher than the number produced by the same procedure performed using Ficoll centrifugation instead of DLD.

E194. A method of preparing CART cells, comprising:
a) collecting cells from a patient by apheresis;
b) performing DLD on the cells obtained in step a) to separate leukocytes from other cells and particles, and to transfer the leukocytes into a medium that supports their growth and that has, or is supplemented with, a T cell activator;
c) performing DLD to separate T cells from the medium of step b) and to transfer cells into a medium where they are recombinantly engineered to express chimeric antigen receptors (CARs) on their surface;
d) performing DLD to separate the T cells from reagents and to transfer the cells into a growth medium;
e) culturing the cells to expand their number
f) performing DLD to transfer expanded T cells into a medium for administration to a patient.

E195. The method of E194, wherein cells are not frozen until they are transferred into a pharmaceutical composition for administration to a patient.

E196. The method of E194, wherein cells are not frozen at any step.

E197. The method of any one of E194-196, wherein, compared to a procedure in which cells are isolated or concentrated by a method other than DLD, the process is completed at least three days sooner.

E198. The method of any one of E194-196, wherein, compared to a procedure in which cells are isolated or concentrated by a method other than DLD, the process is completed at least five days sooner.

E199. The method of any one of E194-196, wherein, compared to a procedure in which cells are isolated or concentrated by a method other than DLD, the process is completed at least ten days sooner.

E200. A method of preparing CAR T cells for the treatment of a patient comprising:
a) collecting cells from a patient by apheresis;
b) performing DLD on the cells obtained in step a) to separate leukocytes from other cells and particles, and to transfer the leukocytes into a medium that supports their growth and that has, or is supplemented with, a T cell activator;
c) separating T cells from the medium of step b) into medium that contains a vector for genetically engineering the T cells to produce chimeric antigen receptors (CARs) on their surface;
d) performing DLD to separate T cells from reagents and to transfer the cells into a medium for administration to a patient.

E201. The method of E200, wherein cells are not frozen until they are transferred into a pharmaceutical composition for administration to a patient.

E202. The method of E200, wherein cells are not frozen at any step.

E203. The method of any one of E200-202, wherein, compared to a procedure in which cells are isolated or concentrated by a method other than DLD, the process is completed at least three days sooner.

E204. The method of any one of E200-202, wherein, compared to a procedure in which cells are isolated or concentrated by a method other than DLD, the process is completed at least five days sooner.

E205. The method of any one of E200-202, wherein, compared to a procedure in which cells are isolated or concentrated by a method other than DLD, the process is completed at least ten days sooner.

E206. The method of any one of E180-205, wherein in step b) a product is obtained in which the ratio of platelets to leukocytes is at least 50% lower than the ratio obtained using centrifugation or elutriation instead of DLD.

E207. The method of any one of E180-205, wherein the yield of T cells exhibiting the desired CAR T phenotype is at least 10% greater than identical cells isolated by Ficoll centrifugation and not subjected to DLD.

E208. The method of any one of E180-205, wherein the yield of T cells exhibiting the desired CAR T phenotype is at least 20% greater than identical cells isolated by Ficoll centrifugation and not subjected to DLD.

E209. The method of any one of E180-208, wherein the time necessary to produce a sufficient number of T cells for the treatment of a patient is at least 5% shorter than when the same method is carried out using Ficoll centrifugation rather than DLD to isolate cells from apheresis starting material.

E210. The method of any one of E180-209, wherein the time necessary to produce a sufficient number of T cells for the treatment of a patient is at least 10% shorter than when the same method is carried out using Ficoll centrifugation rather than DLD to isolate cells from apheresis starting material.

E211. The method of any one of E180-209, wherein, when cells prepared by said method are administered to a patient, they exhibit at least 10% less senescence than cells that have been processed from an apheresis composition using centrifugation or elutriation instead of DLD.

E212. The method of any one of E180-209, wherein, when cells prepared by said method are administered to a patient, they exhibit increased efficacy when compared to cells that have been processed from an apheresis composition using centrifugation or elutriation instead of DLD.

E213. A method for treating a patient for a disease or condition comprising administering to said patient a therapeutically effective amount of cells prepared by the method of any one of E180-209.

E214. The method of E213, wherein said disease or condition is cancer.

E215. A method of producing therapeutically active cells, comprising:
a) obtaining a sample composition from a patient comprising said cells;
b) performing DLD on the sample to produce a composition enriched in therapeutically active cells, wherein DLD is performed on a microfluidic device comprising:

i) at least one channel extending from a sample inlet to one or more fluid outlets, wherein the channel is bounded by a first wall and a second wall opposite from the first wall;

ii) an array of obstacles arranged in rows in the channel, each subsequent row of obstacles being shifted laterally with respect to a previous row, and wherein said obstacles are disposed in a manner such that, when the crude fluid composition is applied to an inlet of the device and fluidically passed through the channel, the therapeutically active cells in the composition flow to one or more collection outlets where an enriched product is collected, and wherein cells and materials smaller than the therapeutically active cells flow to one more waste outlets that are separate from the collection outlets;

c) optionally genetically engineering the therapeutically active cells in the enriched product obtained in step b);

d) optionally culturing the therapeutically active cells to expand their number;

e) transferring the therapeutically active cells into a pharmaceutical composition for administration to a patient.

E216. The method of E215, wherein the therapeutically active cells are stem cells.

E217. The method of E216, wherein the stem cells are found in the circulation and the sample composition is prepared by apheresis.

E218. The method of E217, wherein at least 70% of platelets are removed from the enriched product of step b).

E219. The method of E217, wherein at least 90% of platelets are removed from the enriched product of step b).

E220. The method of any one of E215-219, wherein all isolation steps and concentration steps are carried out using DLD.

E221. The method of any one of E215-220, wherein cells are not frozen until they are transferred into a pharmaceutical composition for administration to a patient.

E222. The method of any one of E215-220, wherein cells are not frozen at any step.

E223. The method of any one of E215-222, wherein, compared to a procedure in which cells are isolated or concentrated by a method other than DLD, the process is completed at least one day sooner.

E224. The method of any one of E215-222, wherein, compared to a procedure in which cells are isolated or concentrated by a method other than DLD, the process is completed at least three days sooner.

E225. The method of any one of E215-222, wherein, compared to a procedure in which cells are isolated or concentrated by a method other than DLD, the process is completed at least five days sooner.

E226. The method of any one of E215-222, wherein the yield of therapeutically active cells obtained from the sample composition is at least 25% higher than the number obtained by a procedure in which cells are isolated or concentrated by a method other than DLD.

E227. The method of any one of E215-222, wherein, compared to a procedure in which cells are isolated or concentrated by a method other than DLD, the process is completed at least three days sooner.

E228. The method of any one of E215-222, wherein, compared to a procedure in which cells are isolated or concentrated by a method other than DLD, the process is completed at least five days sooner.

E229. The method of any one of E215-222, wherein the time necessary to produce a sufficient number of therapeutically active cells for the treatment of a patient is at least 5% shorter than when the same method is carried out using Ficoll centrifugation rather than DLD to isolate cells from the sample composition.

E230. The method of any one of E215-222, wherein the time necessary to produce a sufficient number of therapeutically active cells for the treatment of a patient is at least 10% shorter than when the same method is carried out using Ficoll centrifugation rather than DLD to isolate cells from the sample composition.

E231. The method of any one of E215-230, wherein, when the therapeutically active cells prepared by said method are administered to a patient, they exhibit at least 10% less senescence than cells that have been processed from an apheresis composition using centrifugation or elutriation instead of DLD.

E232. The method of any one of E215-230, wherein, when the therapeutically active cells prepared by said method are administered to a patient, they exhibit increased efficacy when compared to cells that have been processed from the sample composition using centrifugation or elutriation instead of DLD.

E233. A method for treating a patient for a disease or condition, comprising administering to said patient a therapeutically effective amount of the therapeutically active cells prepared by the method of any one of E215-230.

E234. The method of E233, wherein said the therapeutically active cells are stem cells and the disease or condition is a genetic disease.

E235. A method of engineering a population of target cells, comprising:
a) isolating the target cells from a crude fluid composition wherein isolation is carried out on a microfluidic device, using one or more procedures which separate target cells from other cells in the crude fluid composition based on differences in size and wherein the isolation produces a composition enriched in target cells;
b) genetically engineering the target cells obtained from step a) to have a desired phenotype;
wherein target cells are not centrifuged or elutriated prior to being genetically engineered.

E236. The method of E235, wherein said target cells are leukocytes or stem cells.

E237. The method of E235, wherein said target cells are T cells.

E238. The method of any one of E235-237, wherein said crude fluid composition is blood or an apheresis preparation obtained from a patient.

E239. The method of E238, wherein isolation of target cells takes place under conditions such that the composition enriched in target cells has a total number of platelets that is at least 70% lower than in the apheresis preparation.

E240. The method of E239, wherein the total number of platelets in the composition enriched in target cells is at least 90% lower than in the apheresis preparation.

E241. The method of E240, wherein the ratio of platelets to target cells is at least 50% lower than in the apheresis preparation.

E242. The method of E238, wherein said target cells are T cells that, after isolation are expanded in cell culture.

E243. The method of E242, wherein the number of T cells obtained after 14 days in culture is at least two times higher than in a procedure in which T cells are isolated by a process including a centrifugation step.

E244. The method of E242, wherein the number of T cells obtained after 14 days in culture is at least four times higher than in a procedure in which T cells are isolated by a process including a centrifugation step.

E245. The method of E244, wherein the percentage of memory T cells in culture relative to the total number of T cells is at least 10% higher than in a procedure in which T cells are isolated by a process including a centrifugation step.

E246. The method of E244, wherein the percentage of memory T cells in culture relative to the total number of T cells is at least 20% higher than in a procedure in which T cells are isolated by a process including a centrifugation step.

E247. The method of any one of E235-246, wherein, when cells in the composition enriched in target cells are transformed with a vector to express a recombinant phenotype, the yield of target cells exhibiting the desired phenotype is at least 20% greater than for identical cells isolated by centrifugation.

E248. The method of any one of E238-247, wherein no more than one hour elapses from the time that apheresis sample collection is completed until the time that separation using the microfluidic device is performed.

E249. The method of any one of E238-247, wherein no more than four hours elapse from the time the obtaining of the apheresis sample from the patient is completed until the isolation of target cells is completed.

E250. The method of any one of E238-247, wherein no more than four hours elapse from the time the obtaining of the apheresis sample from the patient is completed until cells are genetically engineered.

E251. A method of producing CAR T cells, comprising:
 a) obtaining a crude fluid composition from a patient by apheresis, wherein said sample composition comprises T cells;
 b) isolating the T cells from the crude fluid composition, wherein isolation is carried out on a microfluidic device using one or more procedures which separate T cells from platelets and other cells in the crude fluid composition based on differences in size and wherein the isolation produces a composition enriched in T cells and depleted in platelets;
 c) genetically engineering the T cells obtained from step a) to produce chimeric antigen receptors (CARs) on their surface, and wherein the T cells are not centrifuged or elutriated at any step prior to being genetically engineered;
 d) culturing the genetically engineered T cells to expand their number;
 e) collecting the cultured cells produced in step d).

E252. The method of E251, wherein, in step e), T cells are collected by being transferred into a pharmaceutical composition for administration to a patient.

E253. The method of E251 or E252, wherein cells are not frozen before being collected.

E254. The method of any one of E251-253, wherein at least 90% of platelets are removed in step b).

E255. The method of any one of E251-254, wherein prior to, or during culturing, cells are exposed to a T cell activator or a carrier.

E256. The method of E255, wherein neither said activator nor said carrier are bound to a magnetic bead or particle.

E257. The method of any one of E251-256, wherein, compared to a procedure in which cells are isolated or concentrated by a method not involving the use of a microfluidic device, the CAR T cells are available for administration to a patient at least one day earlier.

E258. The method of any one of E251-256, wherein, compared to a procedure in which cells are isolated or concentrated by a method not involving the use of a microfluidic device, the CAR T cells are available for administration to a patient at least three days earlier.

E259. The method of any one of E251-258, wherein, in step d), the number of CAR T cells obtained after 14 days in culture is at least two times higher than the number produced by cells obtained using Ficoll centrifugation.

E260. The method of any one of E251-258, wherein, in step d), the number of CAR T cells obtained after 14 days in culture is at least four times higher than the number produced by the same procedure performed using Ficoll centrifugation.

E261. The method of any one of E251-260, wherein, T cells and CAR T cells are never frozen before being administered to a patient.

E262. A method of preparing CAR T cells for the treatment of a patient comprising:
 a) obtaining a crude fluid composition from the patient by apheresis, wherein said composition comprises T cells;
 b) isolating the T cells from the crude fluid composition, wherein isolation is carried out on a microfluidic device using one or more procedures which separate T cells from platelets and other cells in the crude fluid composition based on differences in size and wherein the isolation produces a composition enriched in T cells and depleted in platelets;
 c) genetically engineering the T cells obtained from step a) to produce chimeric antigen receptors (CARs) on their surface, and wherein the T cells are not centrifuged or elutriated at any step prior to being genetically engineered;
 d) culturing the genetically engineered T cells to expand their number;
 e) separating T cells on a microfluidic device using one or more procedures which separate T cells from reagents based on differences in size.

E263. The method of E262, wherein cells are not frozen until they are transferred into a pharmaceutical composition for administration to a patient.

E264. The method of E262, wherein cells are not frozen at any step.

E265. The method of any one of E262-264, wherein, compared to a procedure in which cells are isolated or concentrated by a method that does not use a microfluidic device, the process is completed at least three days sooner.

E266. The method of any one of E262-265, wherein, compared to a procedure in which cells are isolated or concentrated by a method not involving the use of a microfluidic device, the CAR T cells are available for administration to a patient at least one day earlier.

E267. The method of any one of E262-265, wherein, compared to a procedure in which cells are isolated or concentrated by a method not involving the use of a microfluidic device, the CAR T cells are available for administration to a patient at least three days earlier.

E268. The method of any one of E262-267, wherein in step b) a product composition is obtained in which the ratio of platelets to leukocytes is at least 50% lower than the ratio obtained using centrifugation or elutriation.

E269. The method of any one of E262-268, wherein the time necessary to produce a sufficient number of CAR T cells for the treatment of a patient is at least 5% shorter than when the same method is carried out using cells isolated by Ficoll centrifugation.

E270. The method of any one of E262-269, wherein the time necessary to produce a sufficient number of CAR T cells for the treatment of a patient is at least 10% shorter than when the same method is carried out using Ficoll centrifugation to isolate cells from apheresis starting material.

E271. The method of any one of E262-270, wherein, when cells prepared by said method are administered to a patient, they exhibit at least 10% less senescence than cells that have been processed from an apheresis composition using centrifugation or elutriation.

E272. A method for treating a patient for a disease or condition comprising administering to said patient a therapeutically effective amount of cells prepared by the method of any one of E235-271.

E273. The method of E272, wherein said disease or condition is cancer.

EXAMPLES

The following examples are intended to illustrate, but not limit the invention.

Example 1

This study focuses on apheresis samples, which are integral to CAR-T-cell manufacture. The inherent variability associated with donor health, disease status and prior chemotherapy all impact the quality of the leukapheresis collection, and likely the efficacy of various steps in the manufacturing protocols (Levine, et al., *Mol. Therapy: Meth. Clin. Dev.* 4:92-101 (2017)). To stress test the automated DLD leukocyte enrichment, residual leukocytes (LRS chamber fractions) were collected from plateletpheresis donations which generally have near normal erythrocyte counts, 10-20-fold higher lymphocytes and monocytes and almost no granulocytes. They also have ~10-fold higher platelet counts, as compared to normal peripheral blood.

12 donors were processed and yields were compared of major blood cell types and processivity by DLD versus Ficoll-Hypaque density gradient centrifugation, a "gold standard." 4 of these donors were also assessed for "T-cell expansion capacity" over a 15-day period. Each donor sample was processed by both DLD, and Ficoll, and for the 4 donors studied for T-cell expansion capacity the sample was processed using direct magnetic extraction.

Materials and Methods

Microchip Design and Fabrication:

The DLD array used in this study consisted of a single-zone, mirrored, diamond post design (see D'Silva, J., "Throughout Microfluidic Capture of Rare Cells from Large Volumes of Blood;" A Dissertation Presented to the Faculty of Princeton University in Candidacy for the Degree of Doctor of Philosophy (2016)). There were 14 parallel arrays per chip resulting in a 14-lane DLD device (FIG. 1D). The device was designed with a 16 μm gap between posts and a ¹/₄₂ tilt, resulting in a critical diameter of ~4 μm. The plastic DLD device was generated using a process called soft-embossing. First, a silicon (Si) master for the plastic DLD microchip was made using standard photolithographic and deep reactive ion etching techniques (Princeton University, PRISM). The features on the silicon master were then transferred to a soft elastomeric mold (Edge Embossing, Medford, Mass.) by casting and curing the elastomer over the Si features. The elastomer was peeled off to create a reusable, negative imprint of the silicon master. A plastic blank sheet was placed between the elastomer molds, and then using a combination of pressure and temperature, the plastic was extruded into the features (wells) of the soft-elastomer negative mold, replicating the positive features and depth of the original silicon master. The soft tool was then peeled off from the plastic device, producing a flat piece of plastic surface-embossed to a depth ~100 μm with a pattern of flow channels and trenches around an array of microposts (FIG. 1D, inset). Ports were created for fluidic access to the Input and Output ends of the microchip. After cleaning by sonication, the device was lidded with a heat-sensitive, hydrophilic adhesive (ARFlow Adhesives Research, Glen Rock, Pa.). The overall chip was 40×75 mm, and 1 mm thick—smaller than the size of a credit card.

DLD Microchip Operation:

The microfluidic device was assembled inside an optically transparent and pressure resistant manifold with fluidic connections. Fluids were driven through the DLD microchip using a constant pneumatic pressure controller (MFCS-EZ, Fluigent, Lowell, Mass.). Two separate pressure controls were used, one for buffer and one for sample. The flow path for the buffer line included tubing connecting a buffer reservoir (60 mL syringe), an in-line degasser (Biotech DEGASi, Minneapolis, Minn.) and the buffer inlet port of the manifold. The flow path for the sample included tubing connecting a sample reservoir (20 mL syringe), a 20 μm PureFlow nylon filter of 25 mm diameter (Clear Solutions, Inc. San Clemente, Calif.) to retain aggregates larger than the microchips nominal gap size (16 μm), and the sample inlet port on the manifold. The outlet ports of the manifold were connected by tubing to collection reservoirs for the waste and product fractions.

The microchips, filter and tubing were primed and blocked for 15 min with running buffer before the sample was loaded. The DLD setup was primed by loading running buffer into the buffer reservoir (60 mL syringe) and then pressurizing; fluid then passed through the tubing and into the manifold "Buffer in" port (FIG. 1). Air in the manifold port was vented via another port on that inlet, and then that port was sealed. The buffer was then driven through the microchip and out both the product and waste outlets, evacuating all air in the micropost array. At the same time, buffer was back flushed up through the "Sample IN" port on the manifold and through the in-line filter, flushing any air. This priming step took ~5 min of hands-on time, and removed all air from the microchip, manifold and tubing. Following the prime step, buffer continued to flush the setup for an additional 15 minutes to block all the interior surfaces; this step was automated and did not require hands-on time.

Following the block step, the system was depressurized, and sample was loaded into the sample container (20 mL syringe). The sample (see below) was diluted 1-part sample to 4 parts running buffer (0.2×) prior to loading on the DLD. The buffer source was re-pressurized first, then the sample source, resulting in both buffer and sample entering their respective ports on the manifold and microchip and flowing through the microchip in parallel (see separation mode, FIG. 1 Ai). Once the sample was loaded and at running pressure, the system automatically processed the entire sample volume. Both product and waste fractions were collected in pre-weighed sterile conical 50 mL tubes and weighed after the collection to determine the volumes collected.

Buffer Systems.

Three different EDTA free buffer formulations were tested on the DLD: 0.5% F127 (Pluronic F-127, Sigma Aldrich, St.

Louis, Mo.) in phosphate-buffered saline 16662038 Ca$^{++}$/Mg$^{++}$ free) (Quality biological, Gaithersburg, Md.), 1% Bovine Serum Albumin (BSA) (Affymetrix, Santa Clara, Calif.) in phosphate-buffered saline [Ca$^{++}$/Mg$^{++}$ free], and an isotonic Elutriation Buffer (EB) composed of 50% Plasmalyte A (Baxter, Deerfield, Ill.) and 50% of a mixture containing 1.0% BSA (Affymetrix, Santa Clara, Calif.) 1.0 mM N-Acetyl-Cysteine, 2% Dextrose and 0.45% NaCl (all from Sigma-Aldrich, St. Louis, Mo.). The buffers were prepared fresh each day, and were sterile-filtered through a 0.2 µm filter flask prior to use on the DLD. All samples in the expansion group were processed using the isotonic elutriation buffer to best align with current CAR-T-cell manufacturing approaches, even though better DLD performance has been established with the addition of poloxamer (Johnson, et al., *Cancer Cell Res.* 27:38-58 (2017)).

Biological Samples.

Leucoreduction System (LRS) chamber samples from plateletpheresis donations of normal screened donors using a Trima system (Terumo, Tokyo, Japan) were obtained from the local blood bank. Cell counts were done at the time of collection by the blood bank. Counts were verified in our lab, using a Beckman Coulter AcT2 Diff2 clinical blood analyzer, and ranged between 76-313.3×10$^3$ WBC/µL and 0.8-4.87×10$^6$ platelets/µL. All samples were kept overnight at room temperature on an orbital shaker (Biocotek, China), and then processed the following day (~24 hours later) to mimic overnight shipment. Each donor sample was processed by both DLD, and Ficoll, and for the 4 donors used for T-cell expansion and immunophenotypic studies the sample was also processed using direct magnetic extraction.

Ficoll-Hypaque.

Peripheral blood mononuclear cells (PBMCs) were obtained by diluting the LRS sample to 0.5× in RPMI (Sigma-Aldrich. St Louis, Mo.), layered on top of an equal volume of Ficoll-Hypaque (GE, Pittsburgh, Pa.) in a 50 mL conical tube, and centrifuged for 35 min with a free-swinging rotor, and no brake, at 400×g. After centrifugation, the top layer was discarded and the interface PBMC fraction transferred to a new 50 mL tube and brought up to 20 mL of RPMI. PBMCs were washed by centrifugation for 10 min at 400×g, the supernatant discarded and the pellet resuspended with 20 mL of RPMI and washed again at 200×g for 10 min. The supernatant was removed and the pellet resuspended in full media containing RPMI-1640+10% Fetal Bovine Serum (FBS) (Sigma-Aldrich, St. Louis, Mo.) plus penicillin 100 units/mL and streptomycin 100 µg/mL antibiotics (Thermo-Fisher, Waltham, Mass.).

Cell Isolation, Counting, and Immunofluorescence Staining.

Prior to and after isolation using the methods described above, the cell counts of the resulting products were determined using a blood cell analyzer (Beckman-Coulter AcT2 Diff2). Once in culture, and after activation, cell counts were determined using the Scepter™ 2.0 hand-held cell counter (Millipore, Billerica, Mass.) and by absolute counting using flow cytometry. Cells from the input, product and waste fractions were then loaded onto poly-lysine-coated slides for 10 min and then fixed for 15 min in 4% p-formaldehyde+ 0.5% Triton X-100 in PBS, before washing 3 times in PBS by centrifugation. Slides were incubated with the conjugated primary antibodies CD41-A647 and CD41-FITC (both from BioLegend San Diego, Calif.) for 60 min in the dark and washed three times with PBS before mounting in slow-fade mounting media containing the DNA stain DAPI (Thermo-Fisher, Waltham, Mass.). Slides were viewed with an Etaluma™ Lumascope 620 fluorescence inverted microscope (Carlsbad, Calif.). Antibodies (mAb) conjugated to fluorochromes were obtained from BioLegend (San Diego, Calif.): CD25-PE, CD25-APC, CD95-FITC, CD45RA-BV605, CD45RO-PECy7, CD197/CCR7 PE, CD279-PE, CD28 PE-Cy5, CD45-PerCP, CD3-FITC, CD3-BV421, CD4-AF700, CD8-APC-AF780, CD61-FITC, CD41-FITC, CD45-Alexa647. Viability of the WBCs obtained by DLD and PBMCs purified by Ficoll-Hypaque was determined by Trypan blue exclusion.

Activation and Magnetic Separation.

For T-cell stimulations in expansion group, DLD, Ficoll and LRS product were diluted to 1×10$^7$ T cells/mL then activated with washed and equilibrated anti-CD3/CD28 conjugated magnetic beads (5.0 µm) (Thermo-Fisher, Waltham, Mass.) at a ratio of 3.2:1 beads per cell for 60 min, and then the activated T cells were separated by a magnetic depletion for 5 min. Unbound cells were removed, and the bead-bound cells were cultured further in full media (below). In the direct magnet protocol, 0.5 mL of LRS sample (same donor as was processed via DLD or Ficoll) was incubated with immunomagnetic CD3/CD28 beads for one hour. The mixture was then placed against a magnet for 5 minutes to capture the T cells. The magnetic bead-bound cells (activated cells) were removed and then diluted to 0.5×10$^6$/mL as above for culture in full media.

After three days in culture, recombinant human IL-2 (BioLegend, San Diego, Calif.) was added at 200 IU/mL to wells. Following cell culture for up to 15 days, beads were removed from cells and cells counted at each time point. To remove beads, the cells in the well were resuspended by passing the cells through a 5-mL pipette for 10 times. Next, the cell suspension was passed throughout a 1 mL pipette 40 times followed by vigorous pipetting using a 200 µL tip for 1 min. Then the cell suspension was placed on the side of a magnet for 5 min and the nonmagnetic fraction was transferred to a fresh tube and counted. The number of cells in the culture wells was determined using a Scepter hand-held cell counter and by flow cytometry.

Cell Culture and Cell Activation.

For each of the T-cell preparations put into cell culture, in addition to the stimulated cells described above, unstimulated cells (controls) were adjusted to 0.5×10$^6$/mL in complete media (RPMI+10% FBS+antibiotics) and plated in 6-well plates (Corning, N.Y.) and cultured at 37° C., 5% CO2 in a humidified incubator. Individual wells, for each condition, unstimulated, and stimulated with and stimulated without IL2, were dedicated to each donor at each time point to eliminate any possibility of disruption in expansion due to sampling and the de-beading activity required for reliable counts, particularly at Day 3.

Flow Cytometry.

No-wash absolute counting by flow cytometry was used for CD3+ cell counts at all time points, Initial day 0 counts used TruCount tubes (BD Biosciences, San Jose, Calif.) to accurately determine the number of cells recovered and counted. Subsequent days used 25,000 123 beads (Affymetrix, Santa Clara, Calif.) which were indexed against TruCount tubes as an internal control. 100 µL of a cell suspension was stained with the CD3 FITC, CD25 PE and CD45 PerCP of conjugated antibodies for 30 min in the dark in either TruCount tubes or with addition of 25,000 123 beads (Affymetrix, Santa Clara, Calif.). The cells were then diluted to 2504 of PBS with a final DRAQ5™ DNA dye (Thermo-Fisher, Waltham, Mass.) concentration of 1.0 mM. Next, the stained cells were fixed with an additional 250 µL 1.2% p-formaldehyde in PBS overnight prior to acquisition. For absolute count cytometry, a minimum of 25,000 events or 2500 bead events were acquired on a BD FACSCalibur (BD Biosciences, San Jose, Calif.) using a fluorescence threshold (CD45 PerCP). Phenotypic analysis was also performed at all time points, using a 7-color activation/anergy panel consisting of CD3, CD45RA, CD95, CD279, CD25, CD4, and CD8. At day 15 the panel was modified to create a 9-color panel focused on T central memory cells which added CD45RO PE-Cy7, CD28 PE-Cy5 and substituted CD197/CCR7 PE for CD279/PD1 PE. For multicolor staining, 100 µl of a cell suspension was stained as above, and resuspended in 750 µL PBS and washed by centrifugation at 400×g and then resuspending in 250 µL 1.2% p-formaldehyde and fixed overnight prior to acquiring 20,000 events using forward scatter threshold on a four laser BD FACSAria II. (BD Biosciences, San Jose, Calif.). All data analysis was performed using Flowlogic Software (Inivai, Melbourne, Australia).

Results

DLD Microchip and Ficoll Processing of Apheresis Products

The DLD and Ficoll separation methods were used to process 12 LRS samples obtained from 12 separate normal donors. Of those 12 samples received and processed, 11 samples clustered around a mean of $148.7 \times 10^3/\mu L$ WBC and $2.52 \times 10^6/\mu L$ platelet counts respectively (FIG. 2A, 2B). The $12^{th}$ sample, with $313.3 \times 10^3/\mu L$ WBC and $4.87 \times 10^6/\mu L$ platelet counts can be seen in the scatter plot as a red triangle, (FIG. 2A). This sample was sufficiently aggregated at the time of processing that it rapidly clogged the 20 µm prefilter and thus did not fully enter the DLD. Microscopic examination of the input sample showed that this sample was full of platelet-WBC aggregates ranging in size from 25-50 µm with multiple aggregates observed as large as 250 µm in diameter (FIG. 2C, 2D). Further, both WBC and platelet counts were greater than 3 standard deviations above the mean WBC and platelet count. Using the quartile method, this sample was classified as a mild outlier; using the Grubbs test for outliers and an alpha level of 0.05, this sample was also classified as an outlier.[20] As a result, this donor was excluded from the study based on extremely high WBC and platelet counts and being too badly agglutinated and damaged.

A representative image of the input material (LRS product diluted to 0.2×) is shown in (FIG. 2A). Typical micrographs of DLD (FIG. 2E) and Ficoll (FIG. 2C) cell products from the same input donor, with significantly lower background platelet levels (CD41-FITC in green) found in the DLD compared to Ficoll. Also shown are the respective cell products, as collected in tubes (FIG. 2 G, H). DLD processing automated the process of removing the WBCs from the RBCs and platelets, generating one tube for product and one for waste, while the Ficoll sample still requires further manual processing to pipet the PMBC layer at the operationally-defined interface of the plasma layer above and Ficoll layer below (FIG. 2H); plus, an additional minimum of two centrifugal washes are required to remove most of the contaminating platelets.

The recovery of WBC, and RBC and platelet depletions of the 11 samples are summarized in Table 2. Mean cell recoveries of PBMC from DLD were ~80%, 17% higher than Ficoll (63%), and, after accounting for the number of CD3 cells in both the DLD and magnetic samples, the DLD product was 36% higher than Direct Magnet (44%). Mean platelet depletion via DLD (83%) was superior to both Ficoll (56.5%) and direct magnet (77%). Mean erythrocyte depletion in these 24-hour old samples was 97% for both DLD and Ficoll, and 94% for the direct magnet approach. The average viability of cells obtained by DLD was 96% compared to Ficoll which were 97%.

The average total time taken to process equivalent aliquots of a single sample in a 50 mL conical tube via the Ficoll technique was timed at ~90 minutes, with approximately 30 minutes of skilled hands-on time required. Timed runs using our single microchip layer breadboard system processed in much shorter time, 50 minutes and required 25 minutes of hands on time, with approximately 20 minutes being due solely to assembly of fluidics components because of the prototypic nature of the otherwise intervention free device.

Cell Expansion and Characterization

Following DLD or Ficoll enrichment, cells were activated using CD3/CD28 magnetic beads for 60 minutes at a target of 3.2 beads per CD3+ cell, separated and then counted prior to plating. Due to limited access to a flow cytometer, and concerns regarding potential bead interference in product cell counts, we estimated the T cell count by counting both the input and non-magnetic fraction and getting the number of T cells bound to the magnet by subtraction, using an assumption of a 90% efficient magnetic separation (based on manufacturer reported efficiencies). Accurate T-cell counts were determined post-plating into culture using absolute counts by flow cytometry and by coulter counts x % CD3 positive cells; these counts established that the original magnetic CD3+ cell depletion process was only 44% efficient (Table 2). This meant that original calculations pertaining to a target of 3.2 beads per CD3+ cell were in fact on average 2.3 for both the DLD and Ficoll fractions (fewer beads per T-cell than targeted), and a 5:1 ratio in the direct magnet fraction (significantly more beads per T-cell than targeted), potentially causing the direct magnet fraction to have even higher fold expansion compared to both the DLD and Ficoll arms.

Flow cytometric characterization of the cultures was performed at each time point to assess consistency of cell activation. Changes in CD25 expression of CD3+ cells, as measured on Day 8, for Ficoll, DLD and direct magnet (FIG. 3). IL-2 Receptor positive (CD25) CD3 cells are shown in Blue (CD4+ plots) and Red (CD8+ plots). DLD prepared cells show more consistent phenotypic expression across the 4 donors for CD25, an indicator of response to CD3/CD28 stimulation, as compared to both Ficoll and direct magnet preparations. DLD prepared CD3+ cells had an average 73% response to co-stimulation compared to Ficoll at 51% (both stimulated at 2.3 beads/cell), while the direct magnet fraction, stimulated at a higher 5:1 ratio, had only a 54% response.

Figure 9:
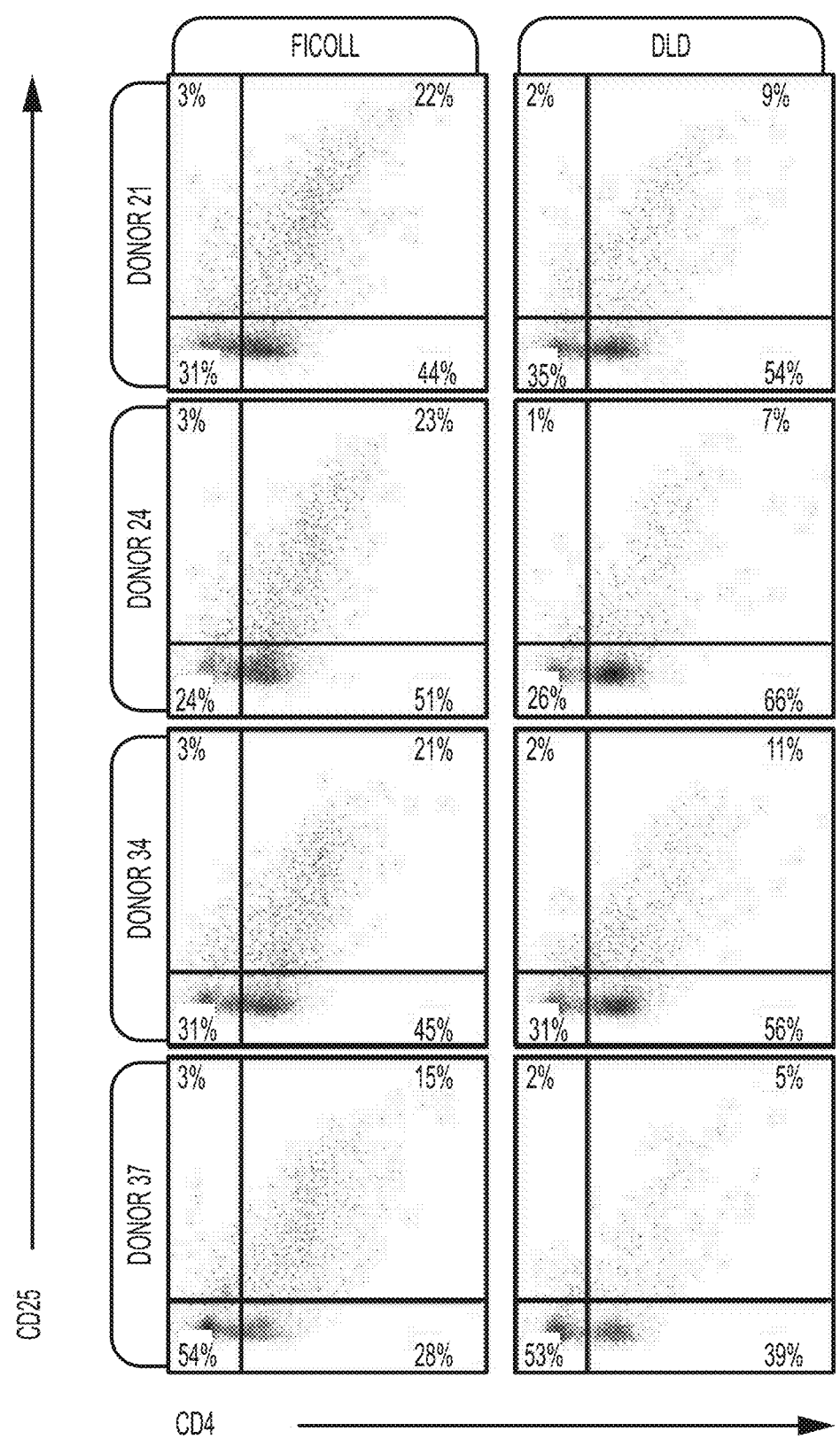
FIG. 9.
Figure 10:
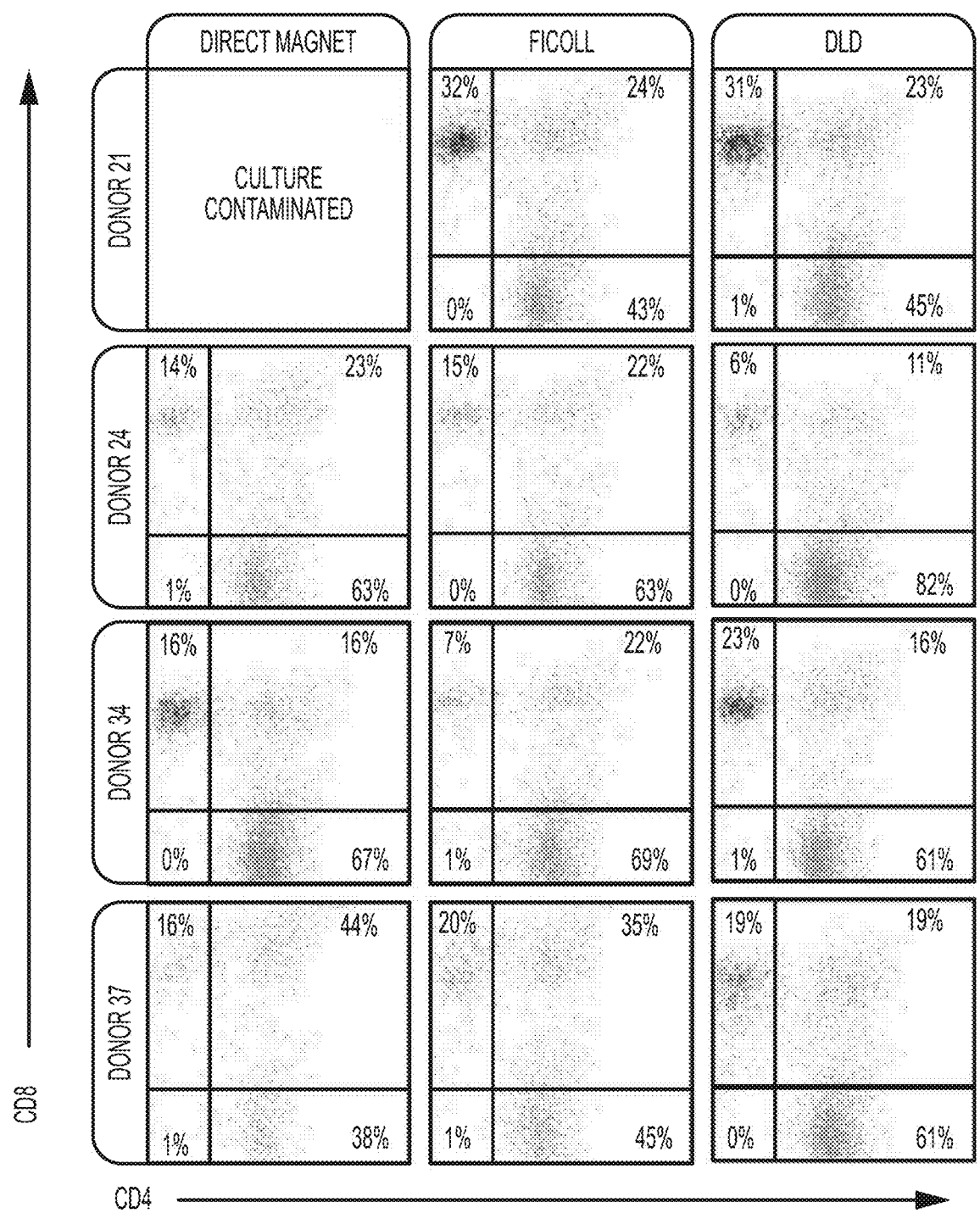
FIG. 10: This is a supplemental figure on the allocation of IL-2 expanded central memory T cells by major subsets. In the original figures: CD8 (Green), CD4 (Blue), CD4+CD8+ (Red) Central memory cells were sequentially gated: CD3+, CD45RO+CCR7+, CD28+CD95+. Relative abundance of CD4 subset driven by IL2 is evident.
Figure 11:
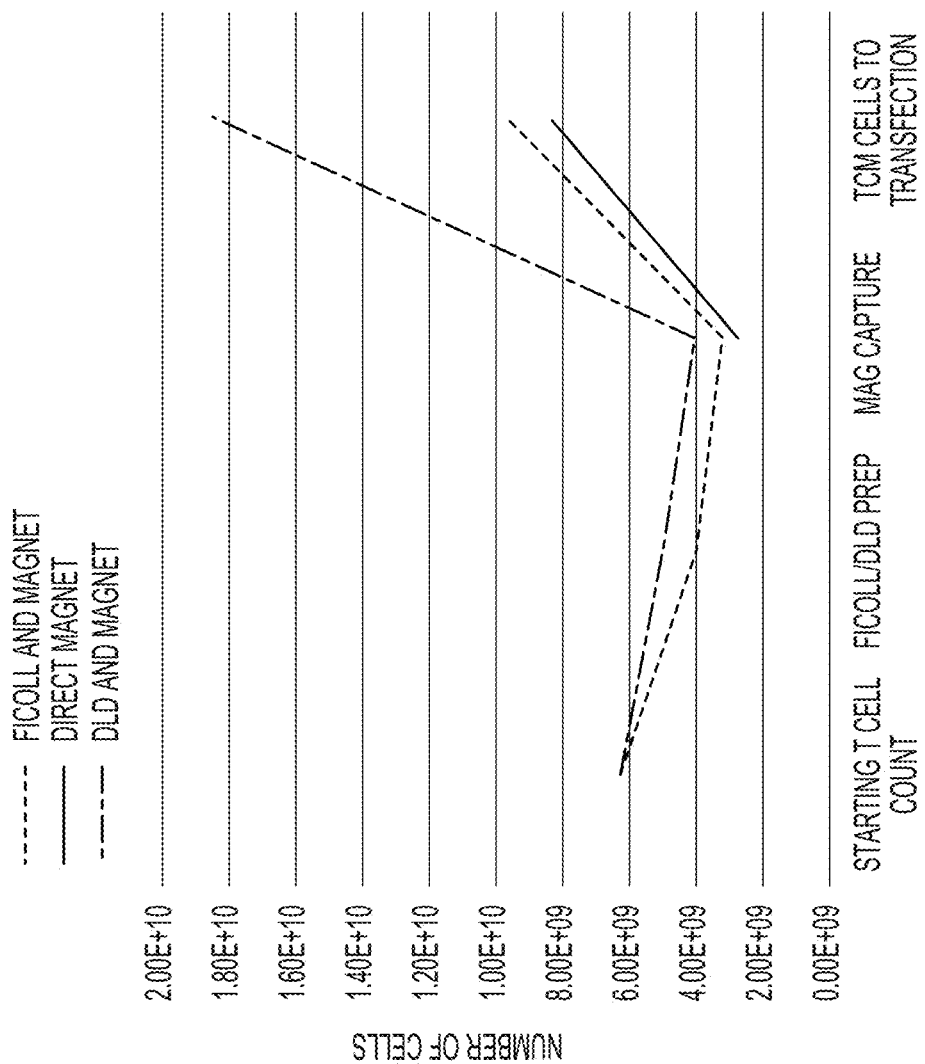
FIG. 11.
Figure 12:
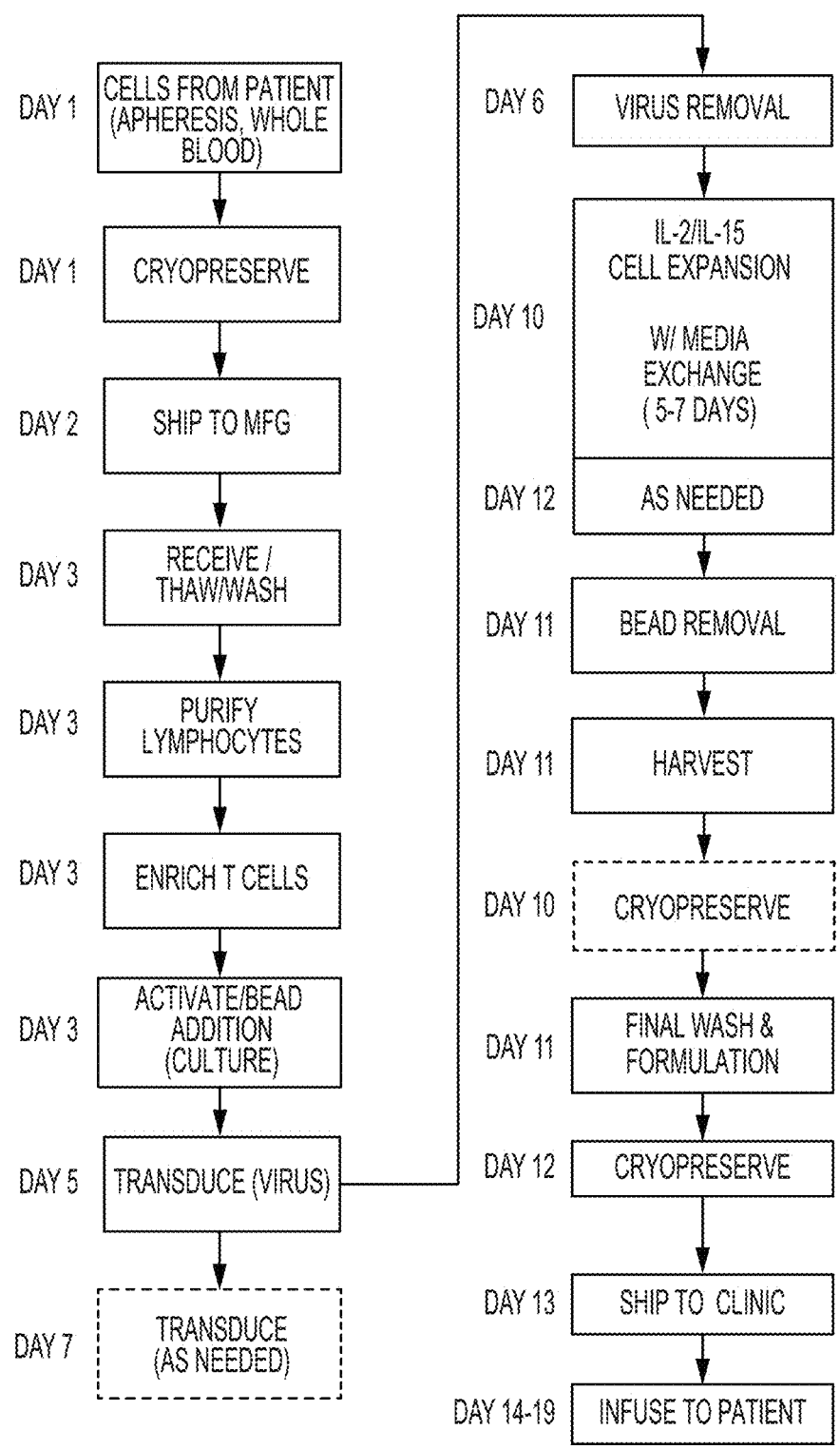
FIG. 12.
Figure 13:
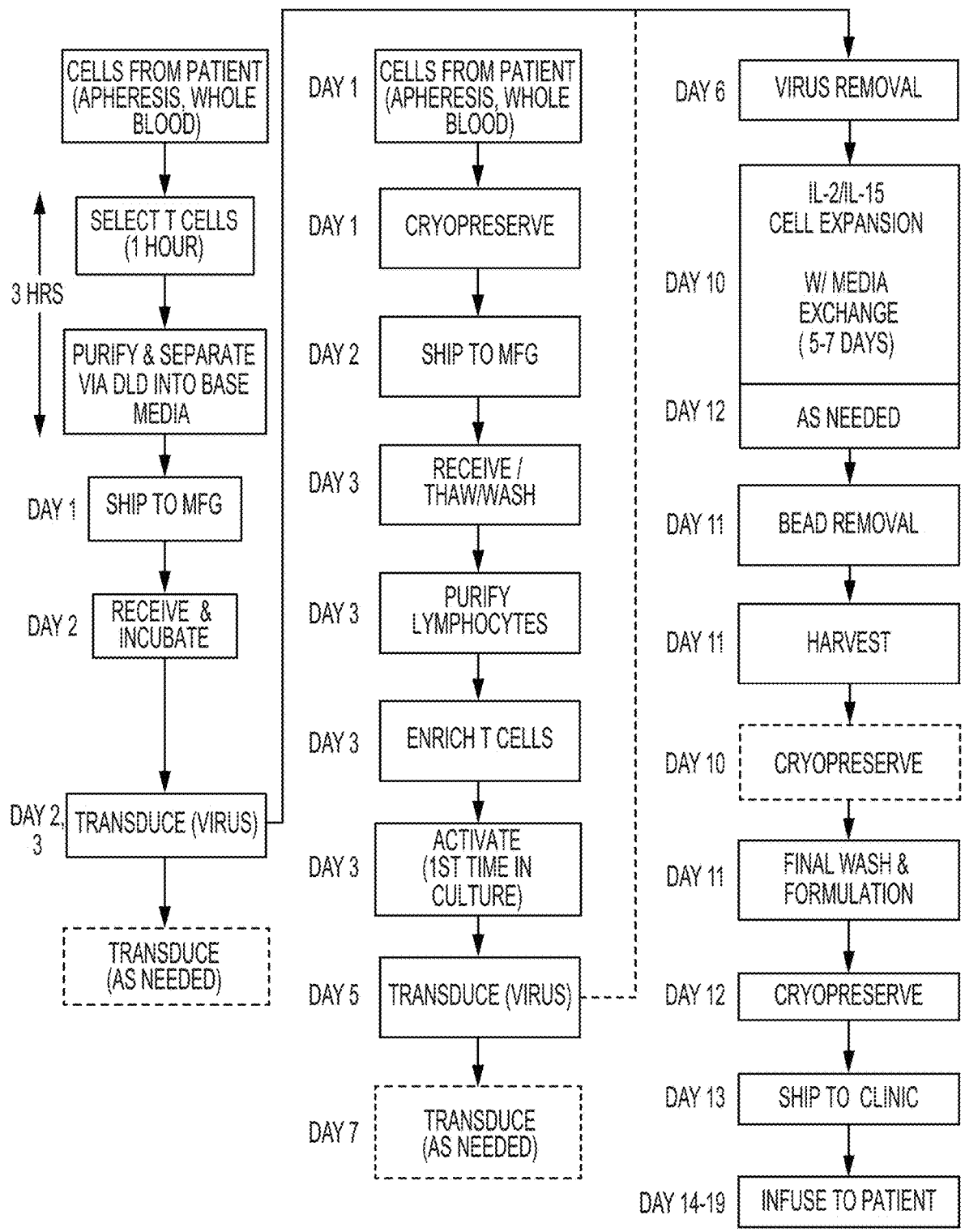
FIG. 13.
Figure 14:
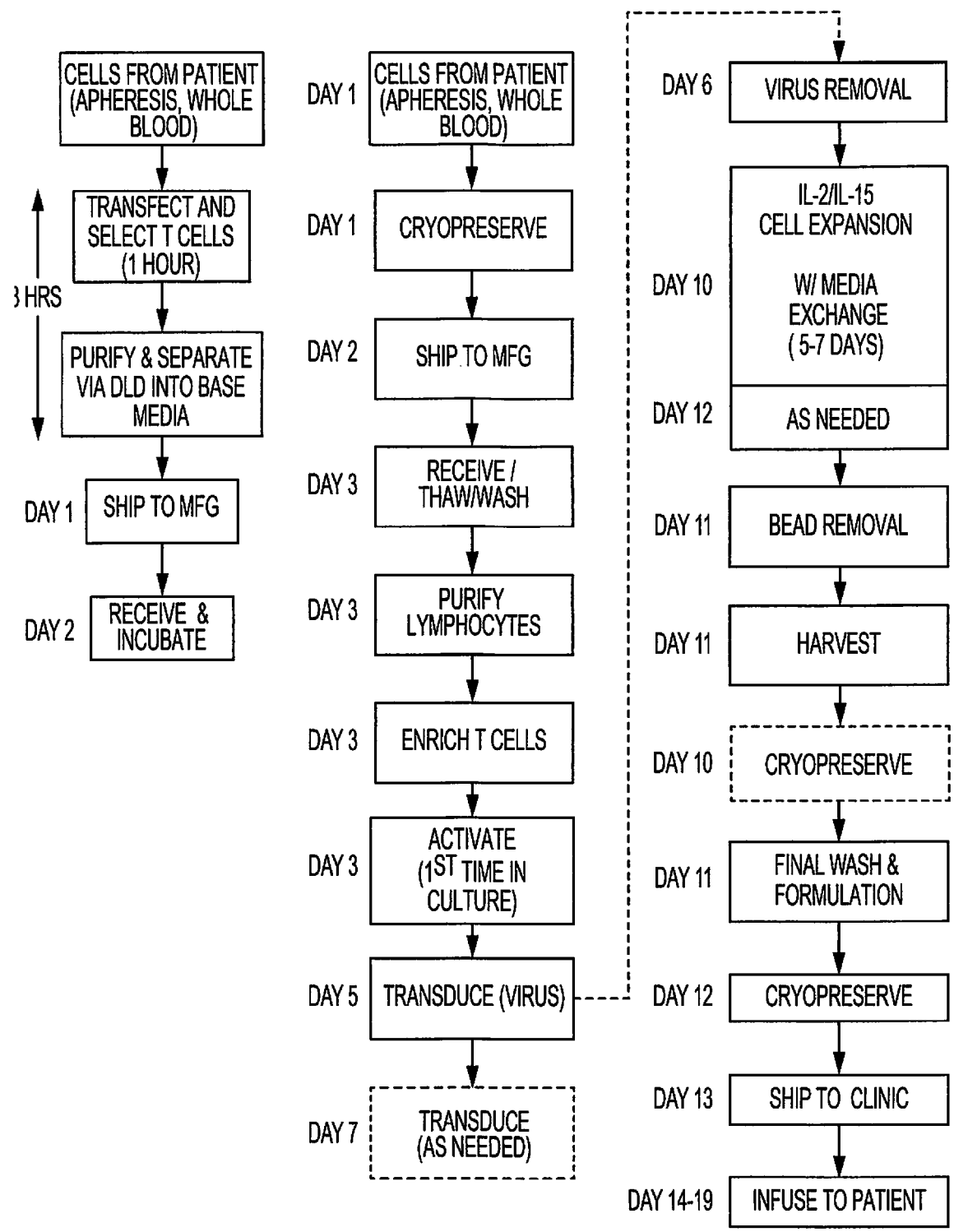
FIG. 14.

Unstimulated controls for Ficoll and DLD show a marked difference, with DLD prepared cells remaining CD25 negative in culture compared to Ficoll (FIG. 9). Interestingly, Donor 37 in the direct magnet fraction did not respond by day 8, but did expand at later time points (also shown in (FIG. 5A)) indicating a potentially delayed response of some samples to the direct magnetic approach.

Figure 4:
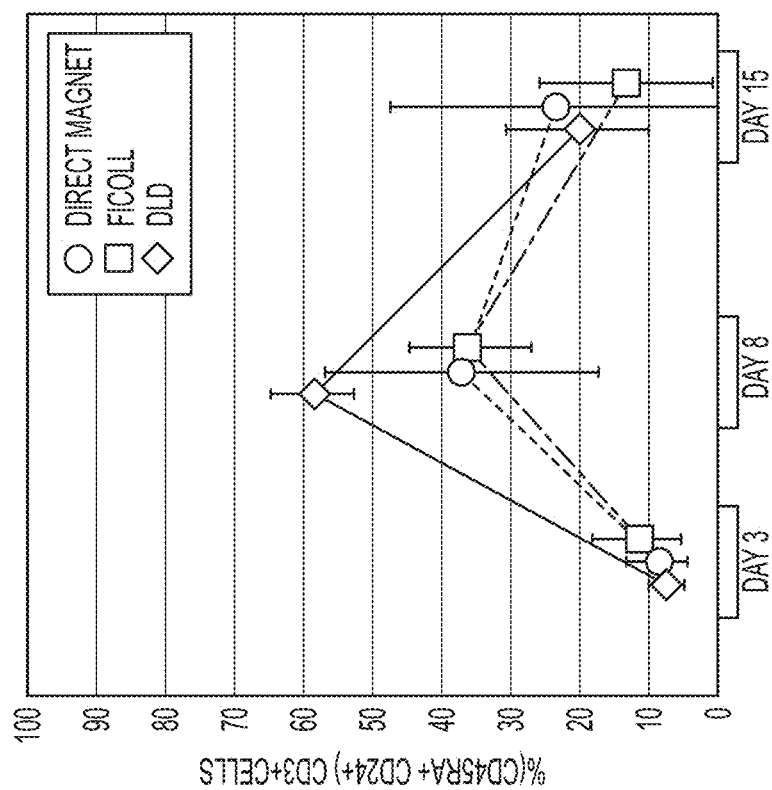
FIG. 4.

In addition to evaluating CD25, conversion to a memory cell phenotype was tracked using percentage of CD3+ cells that were CD45RA− and CD25+. The results shown in FIG. 4 indicate a greater percentage of the cultured cells, as generated via DLD, were responsive to co-stimulation compared to cells processed by Ficoll and direct magnetics. Further, the percent of CD3 cells that were CD25− CD45RA− was lowest in the DLD fraction at 12% as compared to 33 and 29% for Ficoll and Direct Magnet respectively, indicating a more complete conversion towards the CD25+ CD45RA− population with the DLD CD3 cells.

The standard deviation of the CD45RA−CD25+ population at day 8 for DLD was 10.1% as compared to 24.8% for Ficoll and 53.4% for Direct Magnet.

Figure 5A:
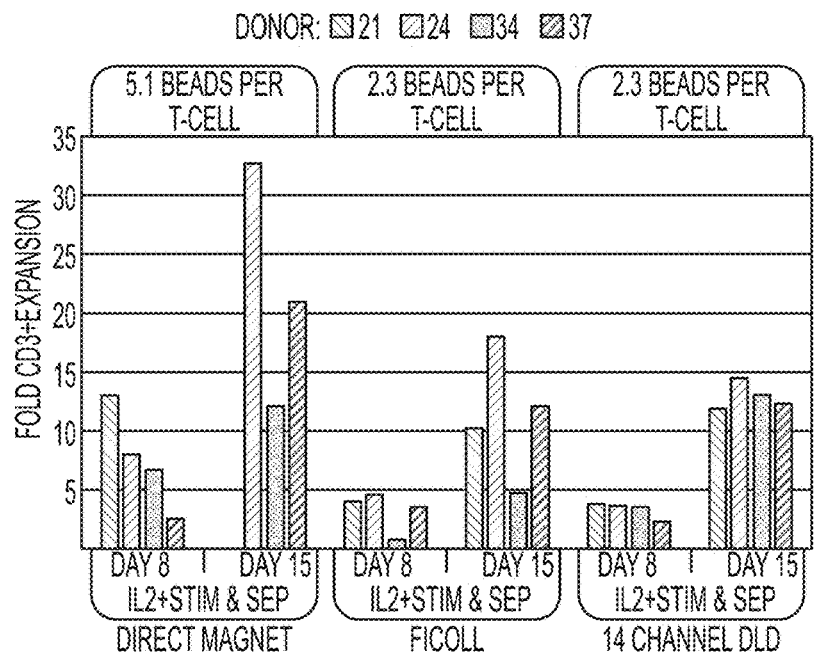
FIGS. 5A-5C: These figures concern the Fold Expansion of CD3 cells ($\times 10^6$) from DLD, Ficoll and Direct Magnet. Aliquots of DLD product and Ficoll cells were incubated with CD3/CD28 beads following Thermo-Fisher CTS protocol using a T cell density of $1 \times 10^7$ T cells/mL. A ratio of ~2.5 Beads/T cell and for the Direct Magnet using ~5.0 Beads/T cell was used, cells and beads were incubated on a rotary mixer for 60 min prior to magnetic separation. Either stimulated or unstimulated (unseparated PMBC) cells were diluted in complete media (RPMI-1640+10% FBS+antibiotics without IL-2) to $0.5 \times 10^6$/mL and were plated in time point specific reactions to avoid any disturbance of the cultures at intermediate time points. On Day 3, 200 IU of IL-2/mL was added to the stimulated and separated arm per manufacturer's recommendation. Cell counts were determined on Day 3, 8, 15 after de-beading using manufacturers protocol (pipetting) by Coulter count (Scepter) and verified by bead based absolute counting using flow cytometry on a BD FACSCalibur using a no-wash approach with a fluorescence threshold on CD45 and staining with CD3− FITC, CD45-PerCP and using the DNA stain DRAQ5 to ensure effective discrimination of doublets and any cells with beads still attached. Correlation between counting methods was acceptable with a slope of 0.95, R2=0.944. Media was added to the cultures to maintain cell densities in an acceptable range ($<3.0 \times 10^6$/mL) on Days 6, and 9. Day 15 data point for the donor 21 was lost due to contamination. Averages or % CV's shown in horizontal bars as indicated (FIG. 5A).

The fold expansion of the individual cultures was determined at day 3, day 8 and day 15; that data is shown in FIG. 5A. The plot shows the expansion of each donor sample, across each method. While the direct magnet approach appears to show higher expansion, the counts are likely significantly affected by the different bead:cell ratios (and corresponding differences in plating density). Regardless, the 4 donors show significant variability in the fold expansion. In addition, the day 15 culture for the direct magnet arm donor #21 became contaminated and had to be discarded, despite having antibiotics present. It is not possible to know if the day 8 expansion data for donor #21 were influenced by the contaminant.

Figure 5B:
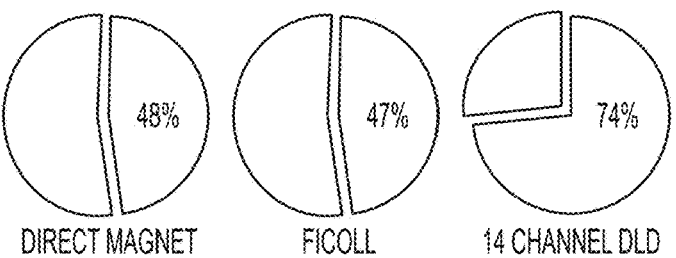
Figure 5C:
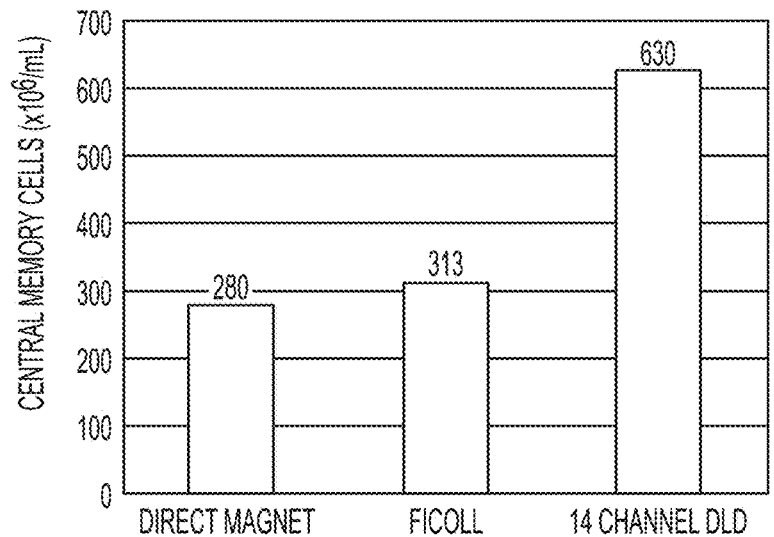

Comparisons between the Ficoll and DLD are valid and much more direct: these cells were plated at the same density and stimulated at the same bead:cell ratio. While the average fold expansion of the DLD cells is not significantly higher than that of the Ficoll cells, the consistency of expansion across the set of 4 donors, and at all days surveyed, is striking. Further the percent of cells in culture that are a central memory phenotype is on average 74% for the DLD arm, contrasted to 47% and 48% respectively for the Ficoll and Direct Magnet arms. Multiplying fold expansion in 5A by percent yield (table 1) and percent memory (FIG. 5B) shows that, despite the sub optimal comparison with bead:cell ratios, that on average twice as many memory cells were produced from the DLD arm as compared to either Ficoll or Direct Magnet arms.

Figures 6A, 6B:
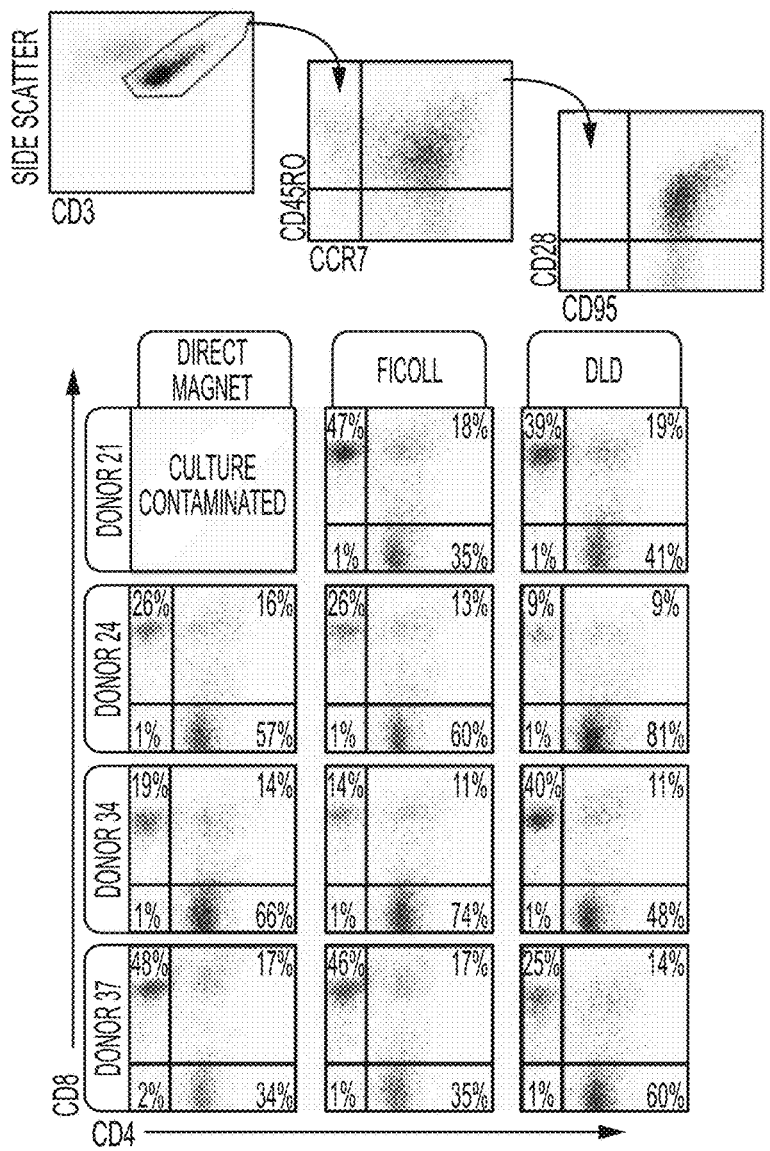
FIG. 6A-6B.
Figure 7:
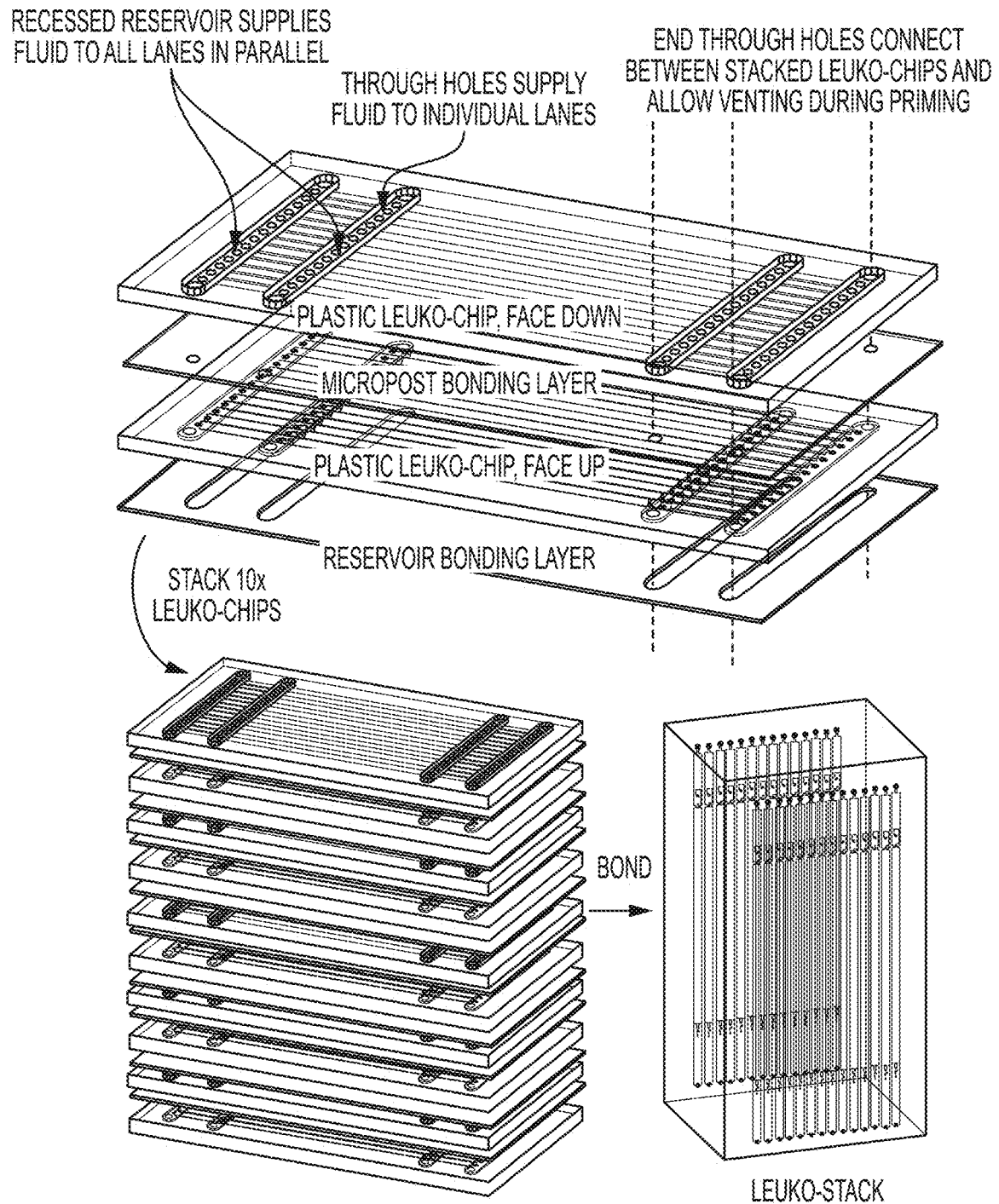
FIG. 7.
Figure 8A:
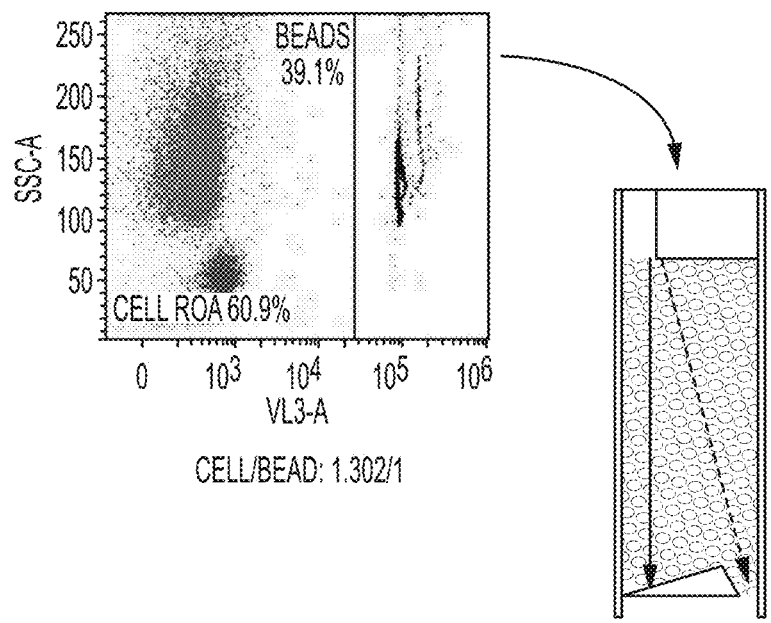
FIGS. 8A-8C: These are supplemental figures showing the concentration of WBC via DLD.
Figure 8B:
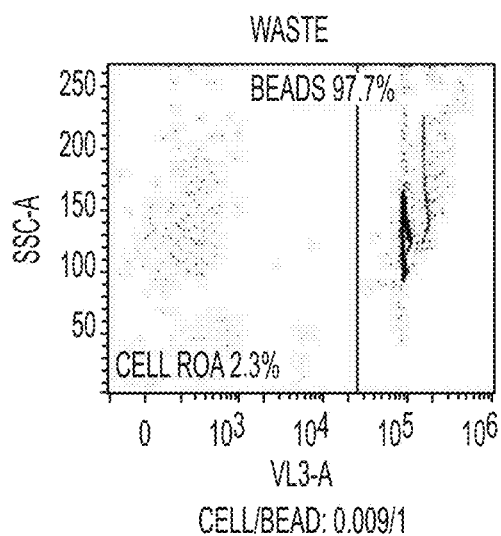
Figure 8C:
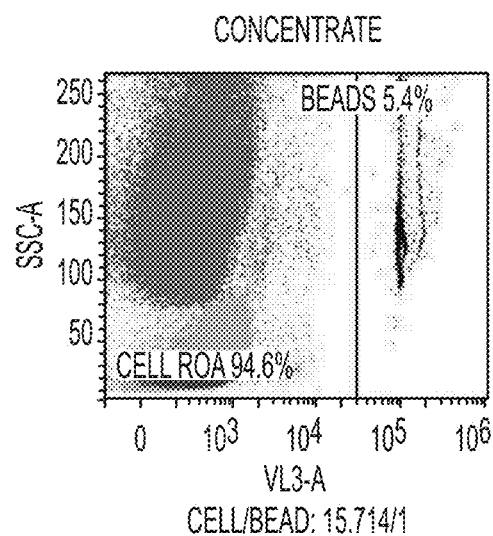

FIG. 6 shows the phenotypic approach to identifying memory cells used in this study, which is designed to eliminate any issues with shed antigens such as CD62L (Mahnke, et al., *Eur. J. of Immunol.* 43:2797-2809 (2013)). Central memory cells are sequentially gated and then back-gated to show the CD3+ T cells are positive for CD45R0+, CD95+, CD28+ and CD197/CCR7+ against all other CD3+ cells in the culture. Using an arbitrary greater than 50% of the culture as being a central memory phenotype as a conversion metric, the DLD arm showed 100% (4/4) donors achieving central memory conversion with an average of 74% of cells being of memory phenotype, with coefficient of variation across donors of 13%. In contrast, the Ficoll arm showed 50% (2/4) converting with an average of 47% memory cells, and a 29% variation. The direct magnet arm achieved 33% (1/3) conversion with an average of 48% memory cells and an associated 79% variation.

TABLE 2

Comparison of DLD, Ficoll and Direct Magnetic Enrichment

|  | WBC Recovery | RBC Depletion | Platelet Depletion |
|---|---|---|---|
| DLD (n = 11) | | | |
| Average | 79.6% | 96.9% | 83.1% |
| STDEV | 13.4% | 1.1% | 12.3% |
| Range | 46.5-93.7% | 95.5-98.6% | 60.5-100.0% |
| Median | 80.1% | 97.0% | 87.6% |
| Ficoll (n = 11) | | | |
| Average | 63.5% | 97.1% | 56.5% |
| STDEV | 16.3% | 1.7% | 22.8% |
| Range | 22.4-83.7% | 94.1-99.9% | 67.0-92.1% |
| Median | 65.6% | 97.0% | 52.3% |

TABLE 2-continued

Comparison of DLD, Ficoll and Direct Magnetic Enrichment

|  | WBC Recovery | RBC Depletion | Platelet Depletion |
|---|---|---|---|
| Direct Magnet (CD3 positive) (n = 4) | | | |
| Average | 44.0% | 94.1% | 77.6% |
| STDEV | 5.8% | 3.3% | 10.4% |
| Range | 36.8-50.7% | 90.1-97.6% | 25.0-99.1% |
| Median | 65.6% | 94.5% | 76.0% |

Example 2: Platelet Add Back Experiment

Rationale

Previously, it has been found that WBC derived from the DLD isolation and purification are healthy and responsive to activation by CD3/CD28 antibodies and differentiate towards their Tcm (T central memory) phenotype (Campos-Gonzalez, et al., SLAS, Jan. 23, 2018, published online doi.org/10.1177/2472630317751214). Additionally, in the presence of IL-2 Tcm cells expand and proliferate accordingly and similarly to cells derived from other methods, like Ficoll.

A key feature of the DLD cell purification is the efficient removal of red blood cells and platelets to provide a highly purified white blood cells (WBC) product. In comparison, Ficoll-derived white blood cells (PBMC's) show more contaminating red blood cells and platelets depending on the sample quality. On average the platelet "contamination" in the Ficoll-derived cells is 44% has a range of about 22% of variability whereas the DLD cells exhibit only a 17% platelet contamination with variability of +/−12%.

Because of the striking differences in the platelet depletion in DLD-processed Apheresis blood when compared to the Ficoll-separated Apheresis blood, an investigation was made of whether the addition of autologous platelets to the DLD-purified white blood cells affects the proliferation and Tcm production over a period of time.

Experimental Details

Two different Leukoreduction System-apheresis ("LRS-apheresis") samples were collected from a local blood bank either as controls or in 2.0 mM EDTA. All four samples were processed identically by two different methods in parallel: DLD processing and Ficoll gradient centrifugation. The original platelet:WBC ratios provided by the blood bank were annotated and confirmed by coulter counter determinations.

3.0 ml of each LRS blood were processed by DLD according to our previously described protocol by diluting the blood to 0.2× with 1.0% BSA/5.0 mM EDTA in PBS. Samples were run with a 1.0% BSA/PBS buffer under standard pressure and condition using an individual DLD-14 lane chip for each sample. Product and waste were collected, and the cellularity was measured using a coulter counter.

3.0 ml of each LRS blood product from the two different donors and conditions (collected in 2.0 mM EDTA or control) were diluted 1:1 with 3.0 ml of Phosphate-buffered saline (minus Calcium and Magnesium) and layered on top of 6.0 ml of Ficoll-Paque in a 50 ml conical tube. The peripheral mononuclear cells of PBMC's were obtained by centrifugation for 35 min at 400×g with no brake. The top layer, or plasma-rich fraction, was removed and transferred to another tube and diluted 1:1 with PBS/1.0% BSA. The PBMC were washed with an excess of PBS by centrifugation, once at 400×g for 10 min and the second time at 200×g for 10 min. Both supernatants were transferred to new 50 ml conical tubes and diluted 1:1 with PBS/1.0% BSA. The diluted plasma-rich fraction and the two supernatants were centrifuged at 1,200×g for 15 min, the supernatants discarded, and the pellets resuspended in PBS/1.0% BSA, combined and centrifuged once more at 1,200×g for 15 min. Supernatant was discarded and the pellet- or platelet fraction-resuspended in 1.0 ml of PBS/1.0% BSA by gentle pipetting. The platelets were measured using the coulter counter. The corresponding platelets were added back to the DLD-derived WBC at the desired ratios and incubated for 1 h before activation with CD3/CD28 magnetic beads (Thermo Fisher).

After activation, the cells were placed in complete RPMI media+10% FBS+antibiotics and cultured over set times in a humidified incubator at 37° C. and 5% CO2. Cell aliquots were analyzed at days 3, 7, and 14 by multi-color flow cytometry using the combination of antibodies indicated in the figures. Cell culture aliquots were obtained at the different days and the cells were de-beaded as previously described before preparation for flow cytometry. Also, cell proliferation was measured by using a Scepter manual cell counter. We then compared the differences between the Ficoll-derived cells with those obtained from the DLD processing under control conditions and when platelets—at different ratios—were added back to the DLD-cells. The parameters we used were the number of cells at the different time points and the number of Tcm cells according to their phenotype by flow cytometry.

The scheme below illustrates the overall experimental design followed during this experiment with steps proceeding from top to bottom.

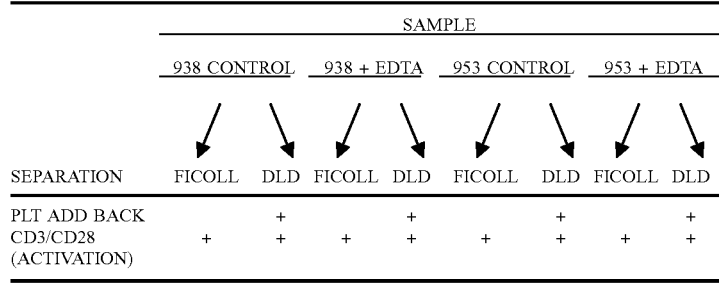

RESULTS AND CONCLUSIONS

Figure 19B:
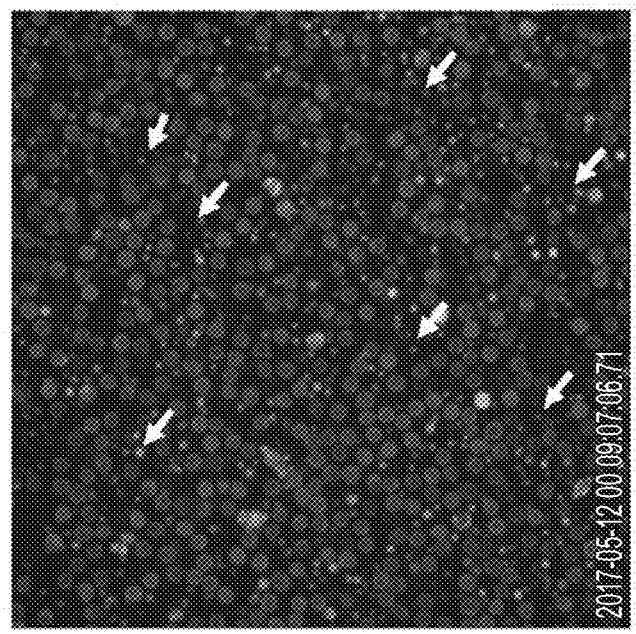
FIGS. 19A and 19B: These figures show the platelets remaining in an apheresis sample processed using DLD (FIG. 19A) and the platelets remaining in an apheresis sample processed using Ficoll centrifugation (FIG. 19B). The platelets are the smaller, brighter cells (some of which are shown by arrows) and leukocytes are the larger darker cells. It can be seen that the relative number of platelets is substantially lower in cells processed by DLD.
Figure 19A:
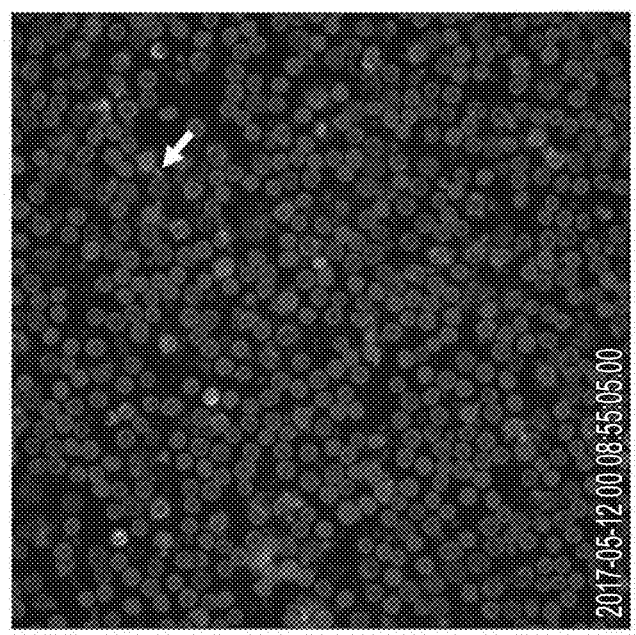
Figure 20:
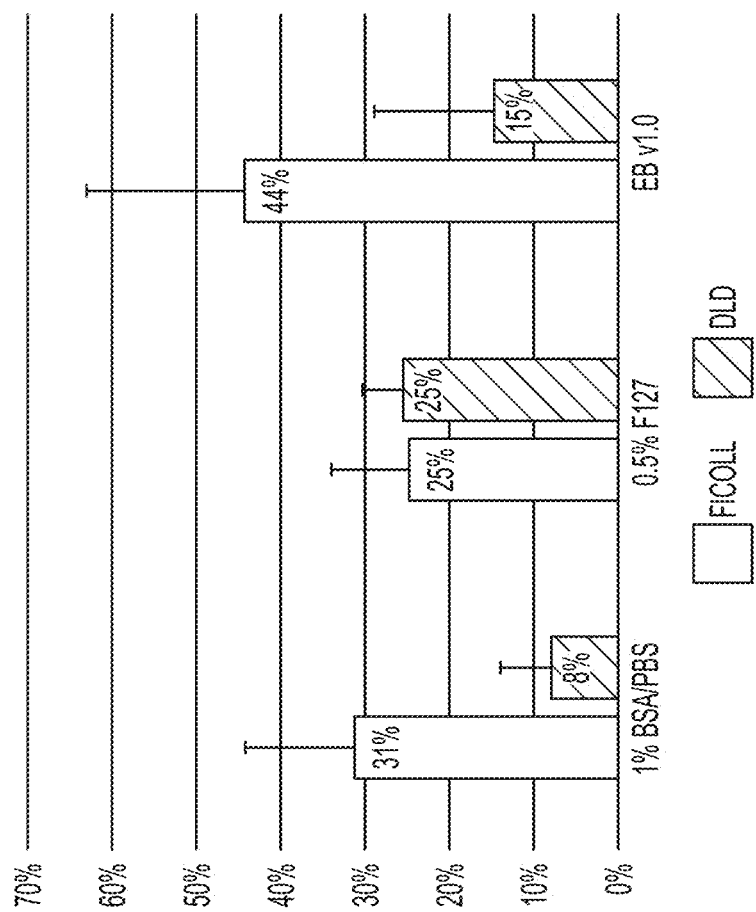
FIG. 20.
Figure 21:
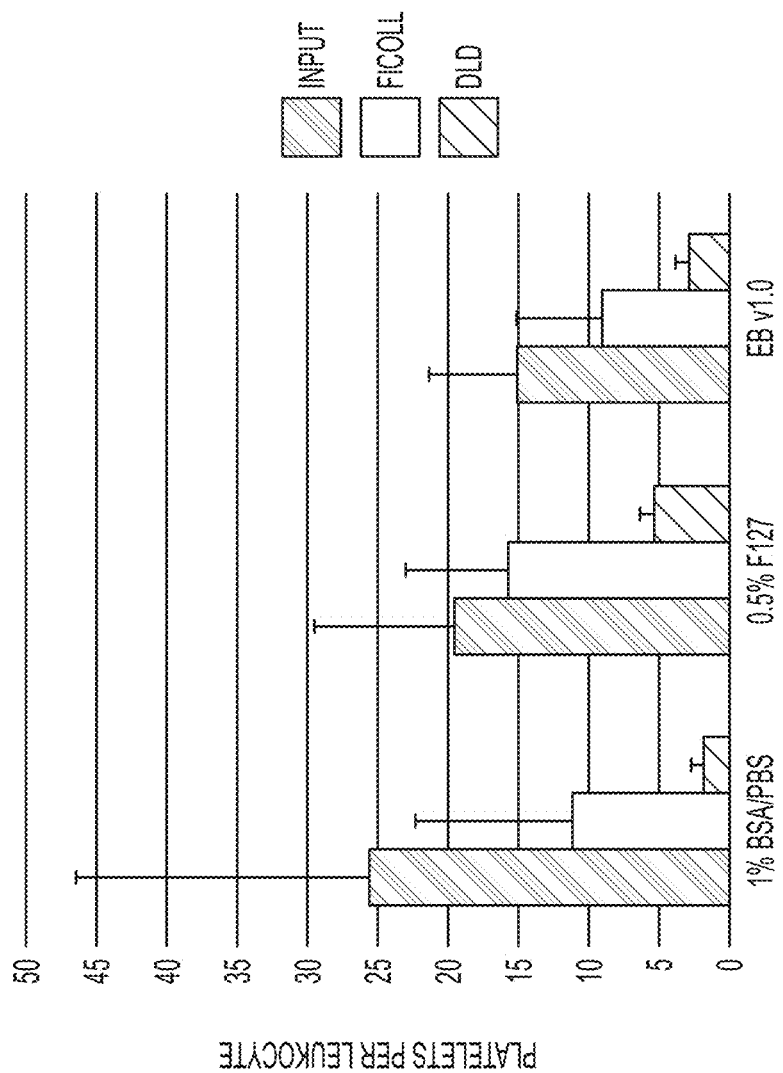
FIG. 21.
Figure 22:
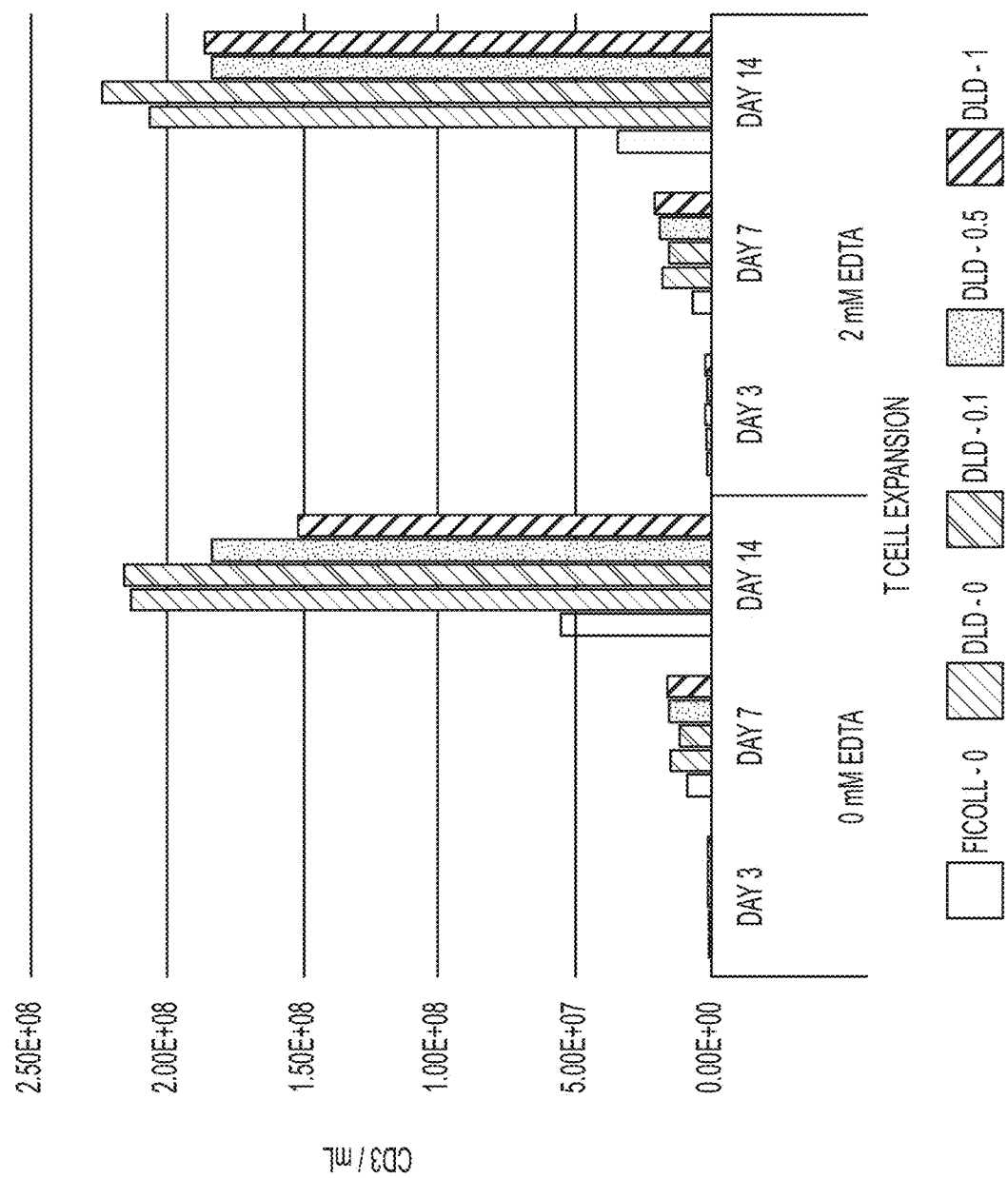
FIG. 22.
Figure 23:
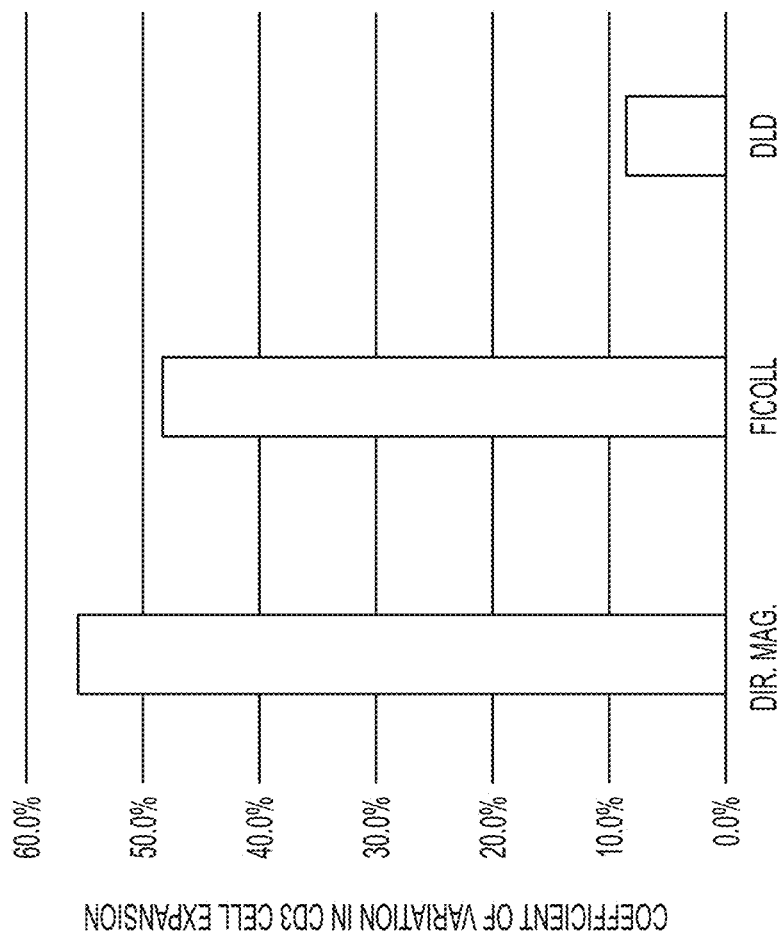
FIG. 23.
Figure 24:
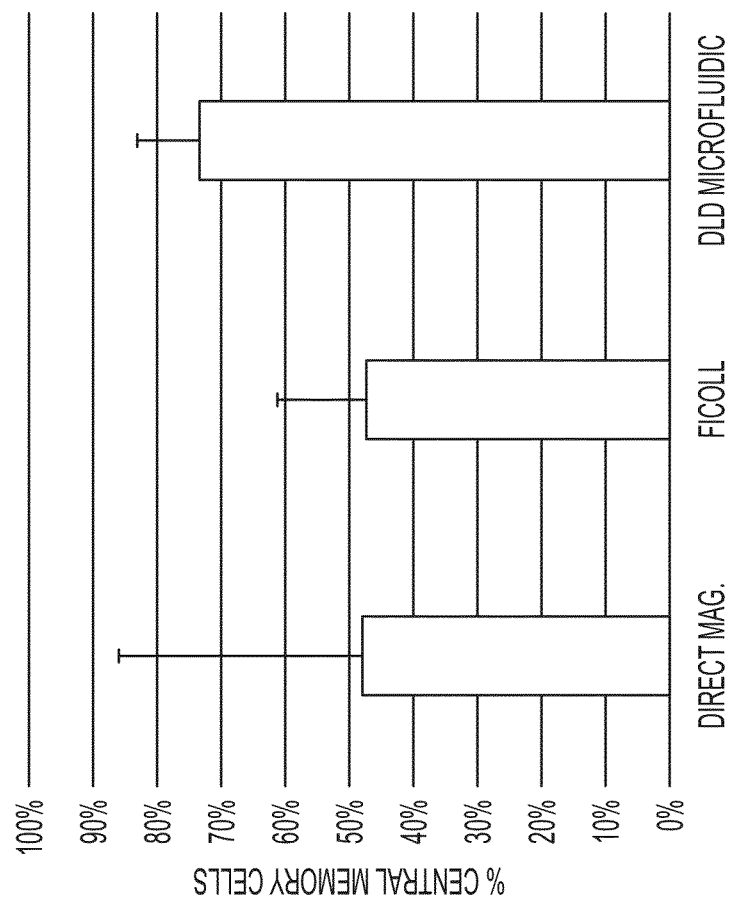
FIG. 24.
Figure 25:
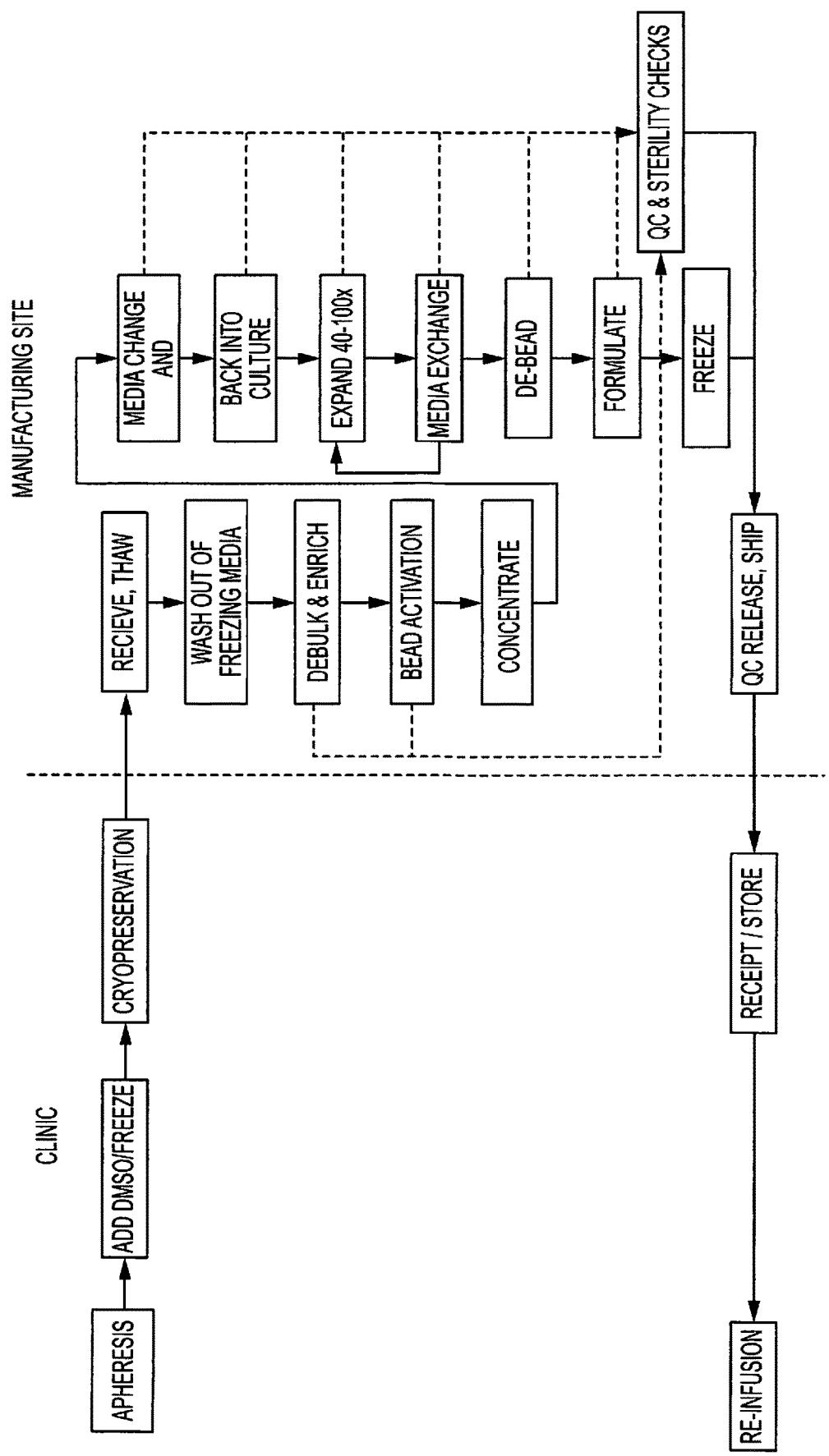
FIGS. 25-32 are all included to illustrate concepts and do not concern any experiments actually performed. The figures illustrate the basic workflow typically involved in obtaining cells from a patient which are then processed and used therapeutically, typically to treat the same patient from which the cells were obtained. The figures, for the most part, refer specifically to the making of CAR T cells but it will be understood that the processes can be applied generally to the making of leukocytes and other cells for therapeutic purposes. In the case of many such processes, including those for CAR T cells, the cells collected from patients are recombinantly engineered to express genes of therapeutic interest. Any type of such engineering may be a part of the illustrated processes. The figures divide steps into those that are performed at a clinic and those that are performed at a separate site, which for the purposes of illustration has been termed a "manufacturing site.
Figure 26:
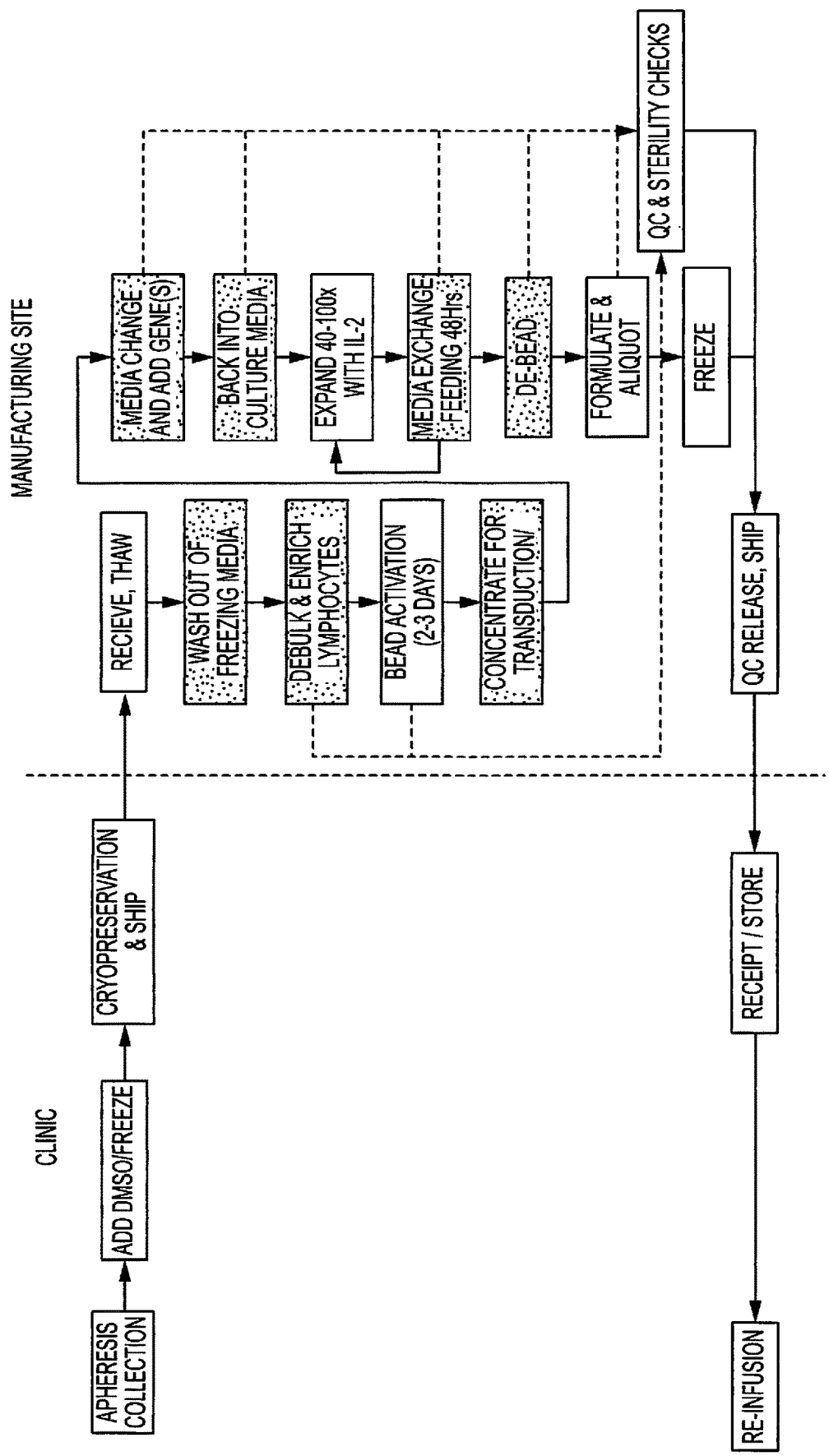
Figure 27:
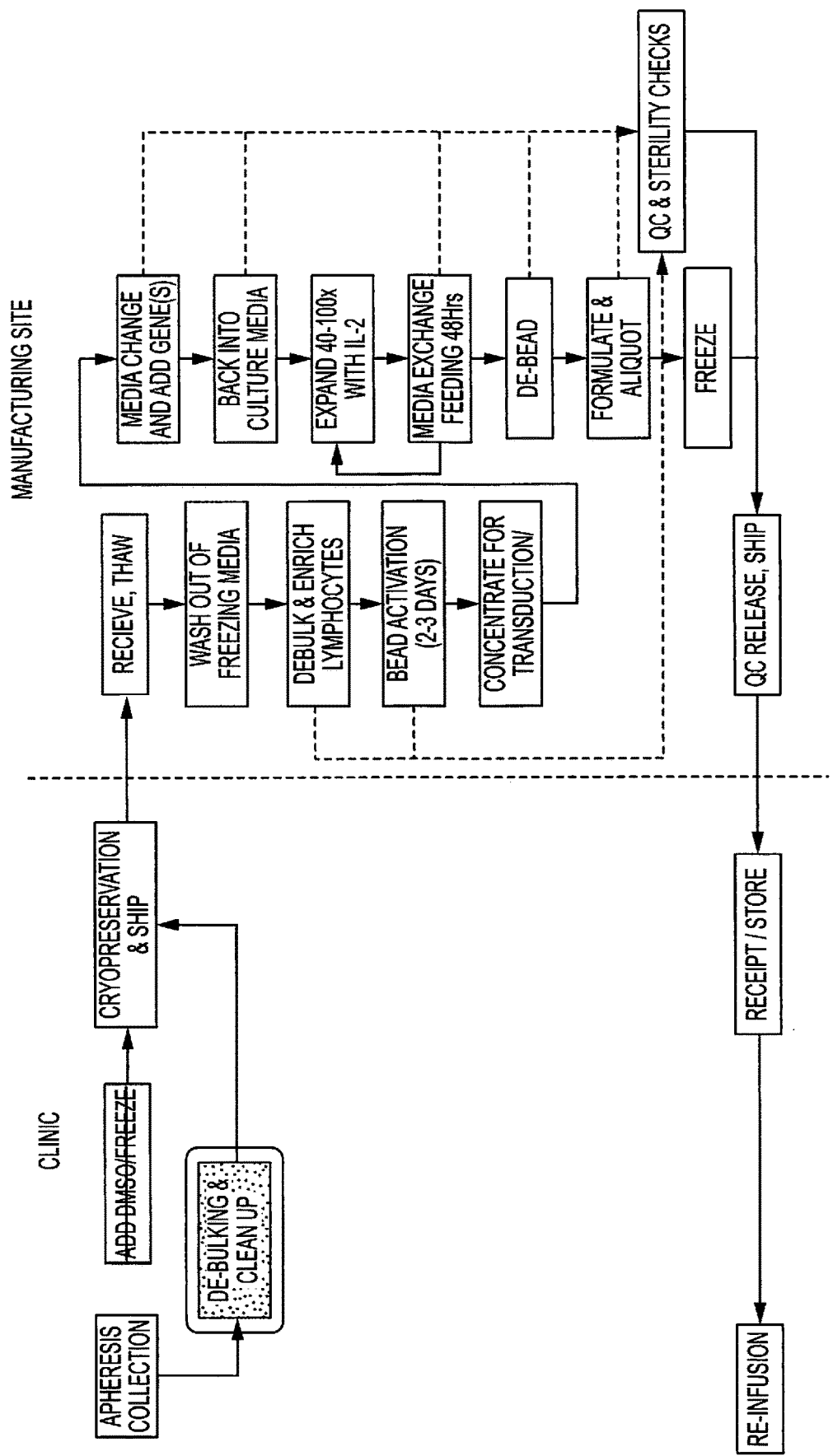
Figure 28:
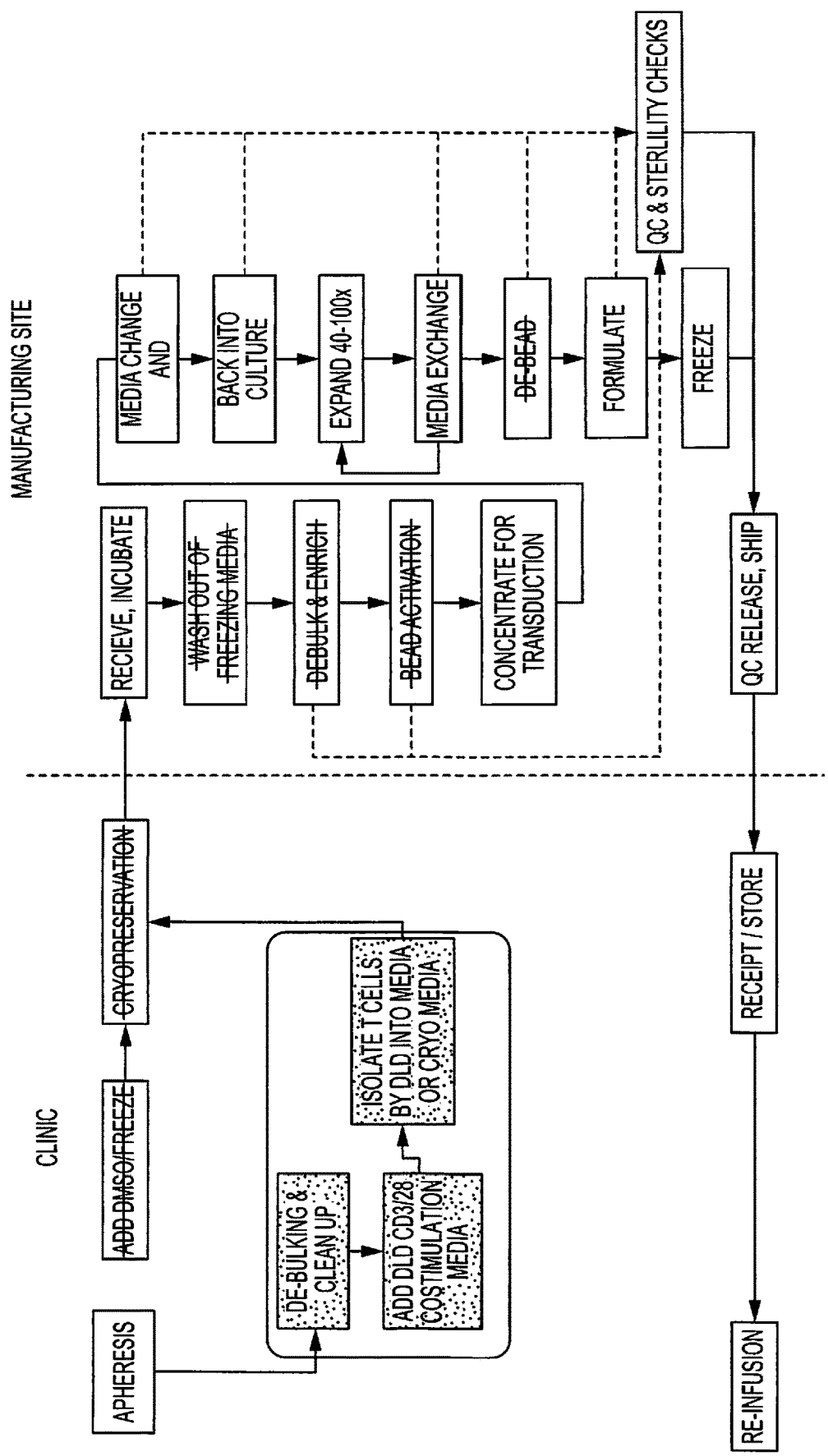
Figure 29:
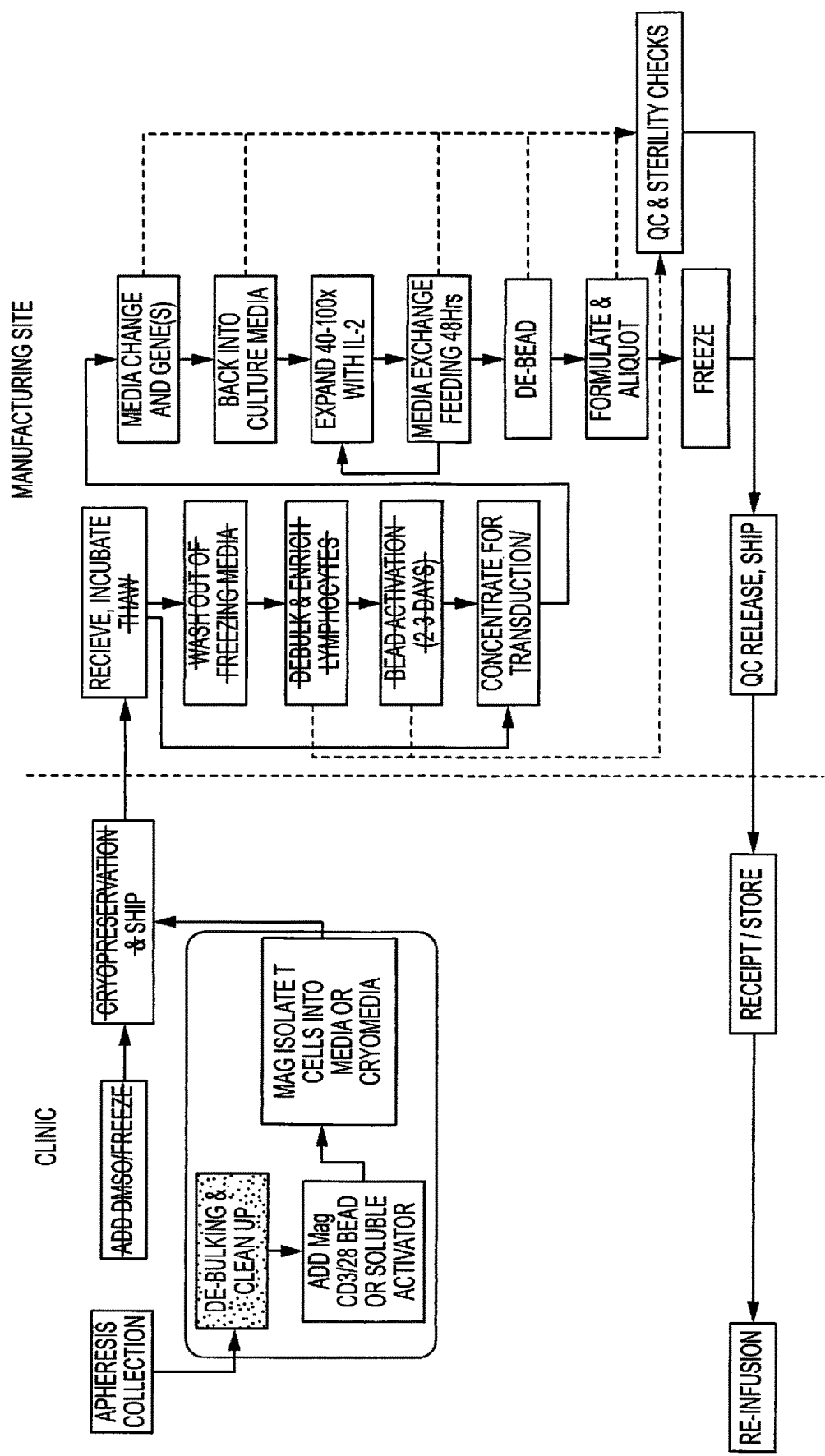
Figure 30:
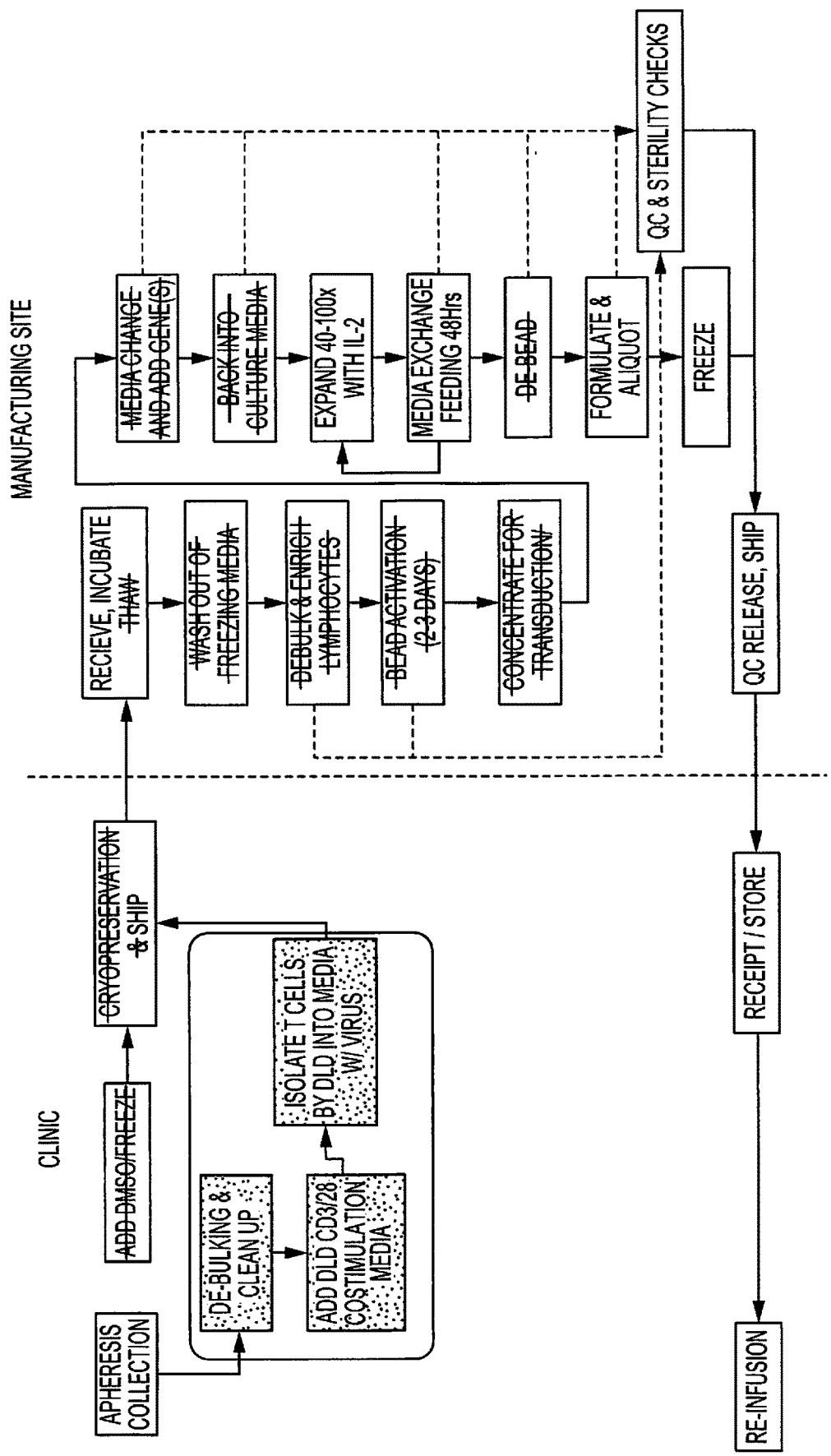
Figure 31:
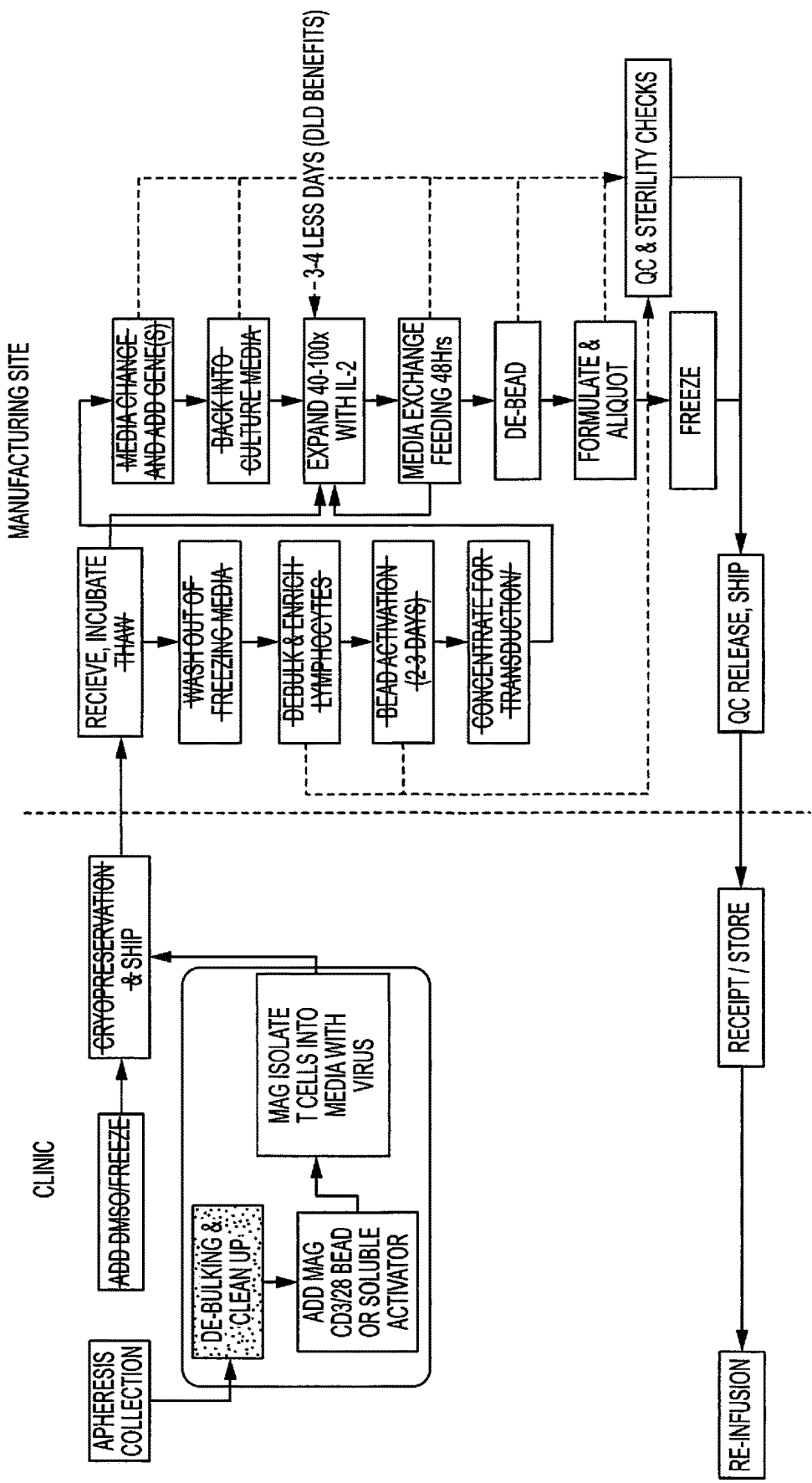
Figure 32:
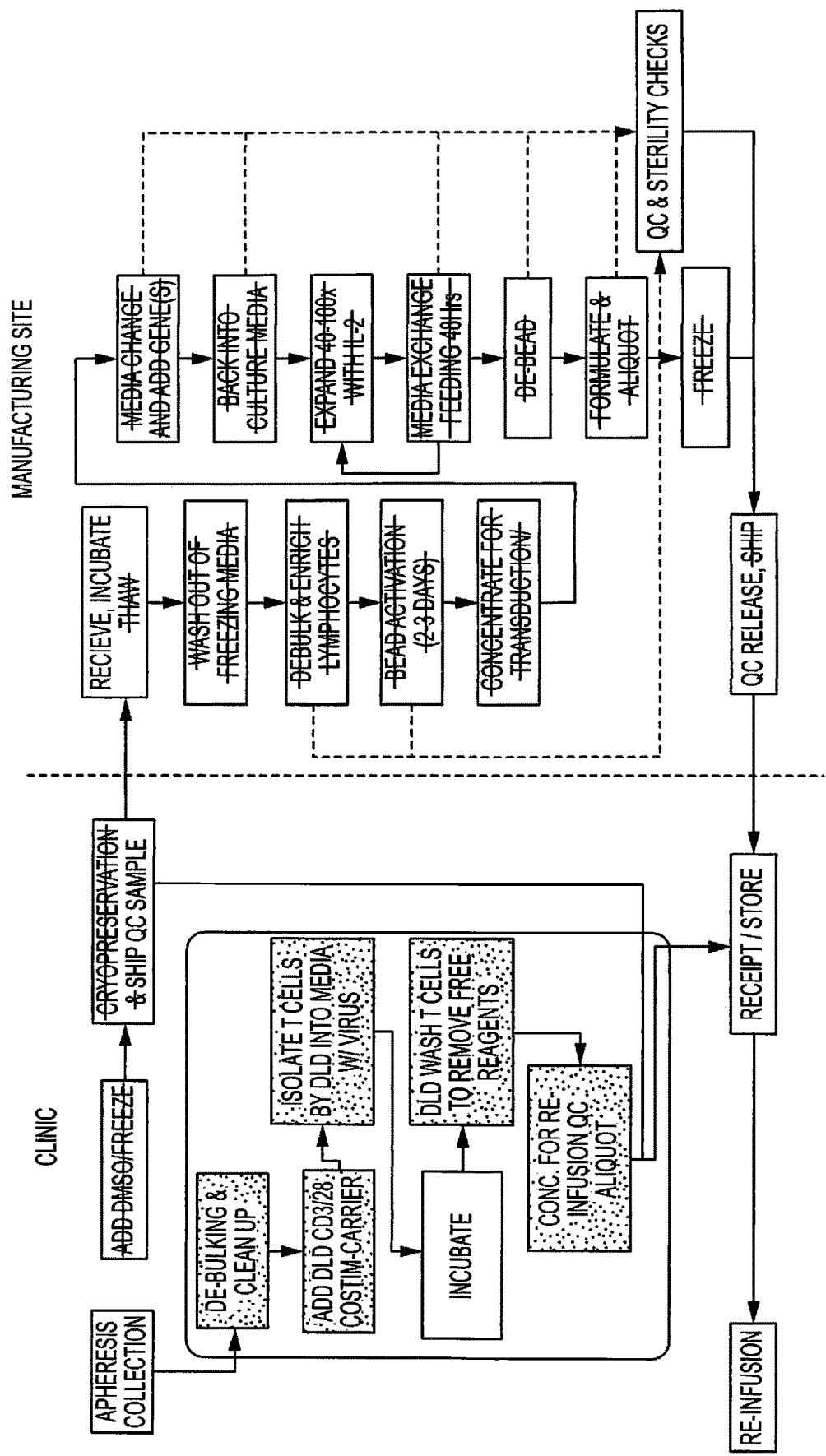

White blood cells obtained using DLD consistently showed less platelets than white blood cells obtained using Ficoll (see FIGS. 19-21). The results also demonstrate a clearly superior expansion of T cells derived from the DLD as compared to their counterparts from Ficoll (FIG. 22). Furthermore, the addition of platelets back to the DLD-isolated cells reduced their ability to expand to the same levels as the platelet-free DLD cells (FIG. 22). These results support the hypothesis that the more efficient platelet-reduction during DLD processing of blood products produces white blood cells more responsive to activation by CD3/CD28 and expansion by IL-2.

REFERENCES

1. Vonderheide, R. H., and June, C. H. Engineering T-cells for Cancer: Our Synthetic Future. *Immunol. Rev.* 2014, 257, 7-13.
2. Fousek, K., and Ahmed, N. The Evolution of T-cell Therapies for Solid Malignancies. *Clin. Cancer Res.* 2015, 21, 3384-3392.
3. Wang, X and Riviere, I. Clinical Manufacturing of CAR-T-cells: Foundation of a Promising Therapy. *Mol. Ther. Oncolytics* 2016, 3, 16015.
4. Sadelain, M., Rivière, I. and Riddell, S. Therapeutic T-cell engineering. *Nature,* 2017, 545, 423-431.
5. National Cell Manufacturing Consortium. Achieving Large-Scale, Cost-Effective, Reproducible Manufacturing of High Quality Cells. A Technology Roadmap to 2025. February 2016.
6. Levine, B. L., Miskin, J., Wonnacott, K., et al. Global Manufacturing of CAR T-cell Therapy. *Mol. Therapy: Meth. Clin. Dev.* 2017, 4, 92-101.
7. Couzin-Frankel, J. Supply of Promising T-cell Therapy is Strained. *Science* 2017, 356, 1112.
8. Johnson, L. A., and June, C. H. Driving Gene-engineered T-cell Immunotherapy of Cancer. *Cell Res.* 2017, 27, 38-58.
9. Hokland, P., and Heron, I. The Isopaque-Ficoll Method Re-evaluated: Selective Loss of Autologous Rosette-forming Lymphocytes During Isolation of Mononuclear Cells from Human Peripheral Blood. *Scand. J. Immunol.* 1980, 11, 353-356.
10. Stroncek, D. F., Fellowes, V., Pham, C., et al. Counter-flow Elutriation of Clinical Peripheral Blood Mononuclear Cell Concentrates for the Production of Dendritic and T-cell Therapies. *J. Transl. Med.* 2014, 12, 241.
11. Powell Jr, D. J., Brennan, A. L., Zheng, Z., et al. Efficient Clinical-scale Enrichment of Lymphocytes for Use in Adoptive Immunotherapy Using a Modified Counterflow Centrifugal Elutriation Program. *Cytotherapy* 2009, 11, 923-935.
12. TerumoBCT. ELUTRA Cell Separation System. Manufacturer recommendations for the Enrichment of Lymphocytes from Apheresis Residues.
13. C. E. Chiche-Lapierre, C. E., Tramalloni, D, Chaput, N. et al. Comparative Analysis of Sepax S-100, COBE 2991, and Manual DMSO Removal Techniques From Cryopreserved Hematopoietic Stem Cell Apheresis Product *Cytotherapy* 2016 18, 6:S47.
14. Huang, L, Cox, E, Austin, R. Continuous particle separation through deterministic lateral displacement, *Science* 2004, 304:987-990.
15. Davis, J. A., Inglis, D. W., et al. Deterministic Hydrodynamics: Taking Blood Apart. *Proc. Natl. Acad. Sci. USA* 2006, 103, 14779-14784.
16. Inglis, D. W., Davis, J. A., Austin, R. H. Critical particle Size for Fractionation by Deterministic Lateral Displacement. *Lab Chip* 2006, 6, 655-658. 17. Chen, Y, D'Silva, J. Austin, R et al. Microfluidic chemical processing with on-chip washing by deterministic lateral displacement arrays with separator walls. *Biomicrofluidics.* 2015 9(5): 054105.

18. Shilun, F. Skelley, A., Anwer, A. G., et al. Maximizing Particle Concentration in Deterministic Lateral Displacement Arrays. *Biomicrofluidics* 2017, 11, 024121.
19. D'Silva, J. Throughout Microfluidic Capture of Rare Cells from Large Volumes of Blood. A Dissertation Presented to the Faculty of Princeton University in Candidacy for the Degree of Doctor of Philosophy. 2016.
20. NIST/SEMATECH e-Handbook of Statistical Methods, 2017, www.itl.nist.gov/div898/handbook/August
21. Mahnke, Y. D., Brodie, T. M., Sallusto, F., et al. The Who's Who of T-cell Differentiation: Human Memory T-cell Subsets. *Eur. J. of Immunol.* 2013, 43, 2797-2809.
22. Civin, C. I., Ward, T., Skelley, A. M., et al. Automated Leukocyte Processing by Microfluidic Deterministic Lateral Displacement. *Cytometry A.* 2016, 89, 1073-1083.
23. Trickett, A., and Kwan, Y. L. T-cell Stimulation and Expansion Using Anti-CD3/CD28 Beads. *J. Immunol. Meth.* 2003, 275, 251-255.
24. Marktkamcham, S., Onlamoon, N., Wang, S., et al. The Effects of Anti-CD3/CD28 Coated Beads and IL-2 on Expanded T-cell for Immunotherapy. *Adv. Clin. Exp. Med.* 2016, 25, 821-828.
25. Li, Y., and Kurlander, R. J. Comparison of Anti-CD3 and Anti-CD28-coated Beads with Soluble Anti-CD3 for Expanding Human T-cells: Differing Impact on CD8 T-cell Phenotype and Responsiveness. *J. Transl. Med.* 2010, 8, 104-118.
26. Agrawal S., Ganguly, S., Hjian, P., et al. PDGF Upregulates CLEC-2 to Induce T Regulatory Cells. *Oncotarget.* 2015, 6, 28621-28632.
27. Zhu, L., Huang, Z., Stålesen, R. et al. Platelets Provoke Distinct Dynamics of Immune Response by Differentially Regulating $CD4^+$ T-cell Proliferation. *J. Throm. Haem.* 2014, 12, 1156-1165.
28. Koesdjojo, M., Lee, Z., Dosier, C., et al. DLD Microfluidic Purification and Characterization of Intact and Viable Circulating Tumor Cells in Peripheral Blood. *AACR Annual Meeting* 2016, Abstract #3956.
29. Loutherback, K. "Microfluidic Devices for High Throughput Cell Sorting and Chemical Treatment," A Dissertation Presented to the Faculty of Princeton University 2011.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A method for preparing cells for treating a patient with cancer, comprising the steps:
   a) purifying T cells from an apheresis sample from said patient, wherein the sample comprises leukocytes and platelets, wherein the leukocytes comprise T cells and wherein the T cells are purified by:
      i) performing a size based separation using a microfluidic device to produce an enriched product in which, compared to the sample, the ratio of platelets to T cells has been reduced by at least 70%; and wherein the microfluidic device comprises:
         at least one channel extending from a sample inlet to one or more fluid outlets, wherein the channel is bounded by a first wall and a second wall opposite from the first wall;
         an array of obstacles disposed in the channel in a manner such that, when the sample is applied to an inlet of the device and fluidically passed through the channel, T cells flow to one or more collection outlets to form an enriched product, and platelets flow to one more waste outlets that are separate from the collection outlets;
      ii) in addition to the size based separation, performing an affinity based separation by binding T cells to a carrier that binds to T cells with specificity, and then separating the carrier-bound T cells from cells not bound to carrier;
   b) after the purification of step a), activating and expanding the T cells to produce a composition in which the percentage of T cells that are central memory T cells has increased compared to the percentage of T cells that are central memory T cells in the sample; and in which the percentage of T cells that are central memory T-cells is greater than in a method in which the sample is not purified by a size based separation using a microfluidic device to reduce the ratio of platelets to T-cells prior to activation and expansion;
   c) after the purification of step a), genetically engineering activated T cells to comprise modified cell surface receptors of therapeutic benefit in the treatment of said patient's cancer;
wherein the T cells in the sample are not centrifuged during the method.

2. The method of claim 1, wherein the carrier of paragraph a)ii) is magnetized.

3. The method of claim 1, wherein, after the cells are prepared, they are administered to said patient.

4. The method of claim 1, wherein in paragraph c), the modified cell surface receptors of therapeutic benefit are chimeric antigen receptors (CARs).

5. The method of claim 1, wherein the percentage of central memory T cells relative to the total number of T cells produced in the method is at least 20% higher than in a method in which centrifugation is used in step a)i) instead of a size based separation on said microfluidic device.

6. The method of claim 1, wherein the sample is a leukapheresis sample.

7. The method of claim 6, wherein the carrier of paragraph a)ii) is magnetized.

8. The method of claim 6, wherein, in paragraph c), the modified cell surface receptors of therapeutic benefit are chimeric antigen receptors (CARs).

9. The method of claim 6, wherein the percentage of central memory T cells relative to the total number of T cells produced in the method is at least 20% higher than in a method in which centrifugation is used in step a)i) instead of a size based separation on said microfluidic device.

10. The method of claim 6, wherein the platelets in the enriched product of paragraph a)ii) are depleted by at least 80% compared to the sample and/or there are no more than 5 platelets per leukocyte in the enriched product.

11. A method for treating a patient with cancer, comprising administering to said patient a therapeutic composition comprising genetically engineered T cells, wherein the genetically engineered T cells have been prepared by a method comprising:
   a) purifying T cells from an apheresis or leukapheresis sample prepared from said patient, wherein the sample comprises leukocytes and platelets, wherein the leukocytes comprise T cells and the T cells are purified by:
      i) performing a size based separation using a microfluidic device to produce an enriched product in which, compared to the apheresis or leukapheresis sample, the ratio of platelets to T cells has been reduced by at least 50%; and wherein the microfluidic device comprises:
- at least one channel extending from a sample inlet to one or more fluid outlets, wherein the channel is bounded by a first wall and a second wall opposite from the first wall;
- an array of obstacles disposed in the channel in a manner such that, when the sample is applied to an inlet of the device and fluidically passed through the channel, T cells flow to one or more collection outlets to form an enriched product, and platelets flow to one more waste outlets that are separate from the collection outlets;

ii) in addition to the size based separation, performing an affinity based separation by binding T cells to a carrier that binds to T cells with specificity, and then separating the carrier-bound T cells from cells not bound to carrier;

b) after the purification of step a), activating and expanding the T cells to produce a composition in which the percentage of T cells that are central memory T cells has increased compared to the percentage of T cells that are central memory T cells in the sample; and in which the percentage of T cells that are central memory T-cells is greater than in a method in which the sample is not purified by a size based separation using a microfluidic device to reduce the ratio of platelets to T-cells prior to activation and expansion;

c) after the purification of step a), genetically engineering activated T cells to comprise modified cell surface receptors of therapeutic benefit in the treatment of said patient's cancer;

wherein the T cells are not centrifuged during the method.

12. The method of claim 11, wherein the carrier of paragraph a)ii) is magnetized.

13. The method of claim 11, wherein in paragraph c), the modified cell surface receptors of therapeutic benefit are chimeric antigen receptors (CARs).

14. The method of claim 11, wherein the enriched product produced in paragraph a)i) has a ratio of platelets to leukocytes that is at least 70% lower than in said apheresis or leukapheresis sample.

15. The method of claim 11, wherein the platelets in the enriched product of paragraph a)i) are depleted by at least 80% compared to the sample and/or there are no more than 5 platelets per leukocyte in the enriched product.

16. The method of claim 11, wherein the percentage of central memory T cells relative to the total number of T cells produced in the method is at least 20% higher than in a method in which centrifugation is used in step a)i) instead of a size based separation on said microfluidic device.

17. The method of claim 11, wherein the T cells are not frozen prior to being genetically engineered.

18. The method of claim 11, wherein the T cells are not activated or bound to a carrier prior to size based separation of paragraph a)i).

19. The method of claim 18, wherein the T cells are not frozen prior to being genetically engineered.

20. The method of claim 18, wherein:
aa) the platelets in the enriched product of paragraph ai) are depleted by at least 80% compared to the sample and/or there are no more than 5 platelets per leukocyte in the enriched product;
bb) in paragraph c) of the method, the modified cell surface receptors of therapeutic benefit are chimeric antigen receptors (CARs).

21. The method of claim 20, wherein the percentage of central memory T cells relative to the total number of T cells produced in the method is at least 20% higher than in a method in which centrifugation is used in step a)i) instead of a size based separation on said microfluidic device.

22. A method for preparing a therapeutic composition comprising genetically engineered T cells, comprising:
a) purifying T cells from an apheresis sample prepared from a patient, wherein the sample comprises leukocytes and platelets, wherein the leukocytes comprise T cells and the T cells are purified by:
i) performing a size based separation using a microfluidic device configured to separate cells by deterministic lateral displacement to produce an enriched product in which, compared to the apheresis sample, the ratio of platelets to T cells has been reduced by at least 70%;
ii) in addition to the size based separation, performing an affinity based separation by binding T cells to a carrier that binds to T cells with specificity, and then separating the carrier-bound T cells from cells not bound to carrier;
b) after the purification of step a), activating and expanding the T cells to produce a composition in which the percentage of T cells that are central memory T cells has increased compared to the percentage of T cells that are central memory T cells in the sample;
c) genetically engineering the activated T cells to comprise modified cell surface receptors;

wherein the percentage of central memory T cells relative to the total number of T cells produced in the method is at least 20% higher than in a method in which centrifugation is used in step a)i) instead of a size based separation on said microfluidic device.

23. The method of claim 22, wherein the sample is a leukapheresis sample.

24. The method of claim 22, wherein the carrier of paragraph a)ii) is magnetized.

25. The method of claim 22, wherein, after the cells are prepared, they are administered to said patient.

26. The method of claim 22, wherein in paragraph c), the modified cell surface receptors of therapeutic benefit are chimeric antigen receptors (CARs).

27. The method of claim 22, wherein the platelets in the enriched product of paragraph a)i) are depleted by at least 80% compared to the sample and/or there are no more than 5 platelets per leukocyte in the enriched product.

* * * * *